United States Patent
Robert et al.

(10) Patent No.: US 10,457,665 B2
(45) Date of Patent: Oct. 29, 2019

(54) 1,4-DI-(4-METHYLTHIOPHENYL)-3-PHTALOYLAZETIDINE-2-ONE AND THE DERIVATIVES THEREOF

(71) Applicants: Universite De Nantes, Nantes (FR); Universite de Bourgogne, Dijon (FR); Institut National de la Sante et de la Recherche Medicale (INSERM), Paris (FR)

(72) Inventors: Jean-Michel Robert, Nantes (FR); Stéphanie Troy-Fioramonti, Dijon (FR); Laurent Demizieux, Dijon (FR); Pascal DeGrace, Dijon (FR)

(73) Assignees: Universite De Nantes (FR); Universite de Bourgogne (FR); Institut National de la Sante et de la Recherche Medicale (INSERM) (FR)

( * ) Notice: Subject to any disclaimer, the term of this patent is extended or adjusted under 35 U.S.C. 154(b) by 0 days.

(21) Appl. No.: 15/762,878

(22) PCT Filed: Sep. 23, 2016

(86) PCT No.: PCT/EP2016/072735
§ 371 (c)(1),
(2) Date: Mar. 23, 2018

(87) PCT Pub. No.: WO2017/050990
PCT Pub. Date: Mar. 30, 2017

(65) Prior Publication Data
US 2018/0265498 A1    Sep. 20, 2018

(30) Foreign Application Priority Data
Sep. 25, 2015   (FR) ..................... 15 59067

(51) Int. Cl.
*C07D 403/04*    (2006.01)
*C07D 205/085*    (2006.01)
*A61P 3/00*    (2006.01)

(52) U.S. Cl.
CPC .............. *C07D 403/04* (2013.01); *A61P 3/00* (2018.01); *C07D 205/085* (2013.01)

(58) Field of Classification Search
CPC .................................................. C07D 403/04
See application file for complete search history.

(56) References Cited

U.S. PATENT DOCUMENTS

2006/0069080 A1    3/2006    Veltri
2008/0274947 A1    11/2008    Jaehne et al.

FOREIGN PATENT DOCUMENTS

WO    2007059871 A1    5/2007
WO    2008039829 A2    4/2008

OTHER PUBLICATIONS

Vippagunta et al. (2001).*
Wolff et al. (1997).*
Banker et al. (1997).*
Schaich, C.L. et al., "Acute and chronic systemic CB1 cannabinoid receptor blockade improves blood pressure regulation and metabolic profile in hypertensive (mRen2)27 rats", Physiological Reports, Jun. 30, 2014, vol. 2, No. 8, E12108.
Slavic, S. et al., "Cannabinoid receptor 1 inhibition improves cardiac function and remodelling after myocardial infarction and in experimental metabolic syndrome", Published online May 1, 2013, vol. 91, pp. 811-823.
Song, D. et al "Acute cannabinoid receptor type 1 (CB1R) modulation influences insulin sensitivity by an effect outside the central nervous system in mice", Diabetologia, Published online Feb. 22, 2011, vol. 54, pp. 1181-1189.
Tam, J. et al., "Peripheral Cannabinoid-1 Receptor Inverse Agonism Reduces Obesity by Reversing Leptin Resistance", Cell Metabolism, Aug. 8, 2012, vol. 16, pp. 167-179.
Tam, J. et al., "Peripheral CB1 cannabinoid receptor blockade improves cardiometabolic risk in mouse models of obesity", The Journal of Clinical Investigation, Aug. 2010, vol. 120, No. 8, pp. 2953-2966.
Tam, J. et al., "The cannabinoid CB1 receptor regulates bone formation by modulating adrenergic signaling", The FASEB Journal, Jan. 2008, vol. 22, pp. 285-294.
Teixeira-Clerc, F. et al., "CB1 cannabinoid receptor antagonism: a new stratergy for the treatment of liver fibrosis", Nature Medicine, Jun. 2006, vol. 12, No. 6, pp. 671-676.
Tripodi, F. et al., "Synthesis and Biological Evaluation of 1,4-Diaryl-2-azetidinones as Specific Anticancer Agents: Activation of Adenosine Monophosphate Activated Protein Kinase and Induction of Apoptosis", Journal of Medicinal Chemistry, Feb. 13, 2012, vol. 55, pp. 2112-2124.
Wang, H. et al., "Jekyll and Hyde: Two Faces of Cannabinoid Signaling in Male and Female Fertility", Endocrine Review, Aug. 2006, vol. 27, No. 5, pp. 427-448.

(Continued)

Primary Examiner — Paul V Ward
(74) Attorney, Agent, or Firm — Lerner, David, Littenberg, Krumholz & Mentlik, LLP

(57) ABSTRACT

The present invention relates to a compound with formula (I) or a salt and/or a pharmaceutically acceptable solvate thereof, the method for preparing same as well as the uses thereof, in particular the therapeutic use thereof, mainly in the treatment of diseases associated with a hyperactivity of the endocannabinoid system.

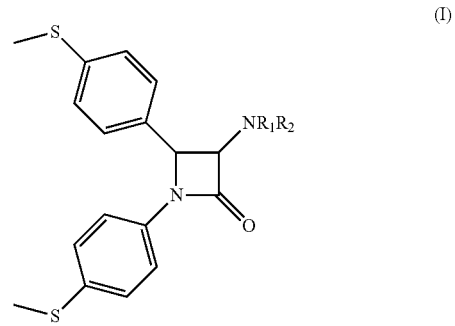

(I)

17 Claims, 21 Drawing Sheets
Specification includes a Sequence Listing.

(56) References Cited

OTHER PUBLICATIONS

Wasserman, E. et al., "CB1 cannabinoid receptors mediate endochondral skeletal growth attenuation by 9-tetrahydrocannabinol", Annals of the New York Academy of Sciences, 2015, vol. 1335, pp. 110-119.
Demonstration of Two New Endocannibinoid System Functions in Hepatic Physiopathology: CB2 receptor and CB1 profibrogenic steatogenic properties:, Dec. 15, 2008, Doctorial Thesis of Vanessa Deaveaux, University Paris Est, Life Sciences and Health, pp. 1-241 (English Abstract of Thesis).
"Systéme endocannabinoïde et cannabinoïdes exogénes", Cannabis: What effects on behavior and health?, National Institute of Health and Medical Research (Inserm), 2001, (Abstract Only).
Amoaka et al., "Relationship between seminal plasma levels of anandamide congeners palmitoylethanolamide and oleoylethanolamide and semen quality", Fertility and Sterility, Nov. 2014, vol. 102, No. 5, pp. 1260-1267.
Beaumont, H. et al., "Effect of 9-tetrahydrocannabinol, a cannabinoid receptor agonist, on the triggering of transient lower oesophageal sphincter relaxations in dogs and humans", British Journal of Pharamcology, vol. 156, pp. 153-162.
Blüher et al., "Dysregulation of the Peripheral and Adipose Tissue Endocannabinoid System in Human Abdominal Obesity", Diabetes, Nov. 2006, vol. 55, No. 11, pp. 3053-3060.
Buckley, N.E., et al., "Expression of the CB1 and CB2 Receptor Messenger RNAS During Embryonic in the Development In The Rat", Neuroscience, 1998, vol. 82, No. 4, pp. 1131-1149.
Cota, D., et al., "The endogenous cannabinoid system effects energy balance via central orexigenic drive and peripheral lipogenesis", J. Clin, Invest. Apr. 15, 2003, vol. 112, pp. 423-431.
Côté, M., et al., "Circulation endocannabinoid levels, abdominal adiposity and related cardiometabolic risk factors in obese men", International Journal of Obesity, Jan. 2007, vol. 31, pp. 692-699.
Das, S.K. et al., "Cannabinoid ligand-receptor signaling in the mouse uterus", Proc. Natl. Acad. Sci USA, May 1995, vol. 92, No. 10, pp. 4332-4336.
Després, Jean-Pierre, et al., "Abdominal obesity and metabolic syndrome", Nature, vol. 444, Dec. 14, 2006, pp. 881-887.
Di Carlo, G., et al., "Cannabinoids for gastrointestinal diseases: potential therapeutic applications", Expert Opinion on Investigational Drugs, published online Mar. 2, 2005, vol. 12, No. 1, pp. 39-49.
Di Marzo, V., "Targeting the endocannabinoid system: to enhance or reduce?", Nature Reviews Drug Discovery, May 2008, vol. 7, pp. 438-455.
Di Marzo, V., et al., "Endocannabinoid control of food intake and energy balance", Nature Neuroscience, May 2005, vol. 8, No. 5, pp. 585-589.
Di Marzo, V., et al., "The role of endocannabinoids in the regulation of gastric emptying: alterations in mice fed a high-fat diet", British Journal of Pharmacology, Jan. 2008, vol. 153, pp. 1272-1280.
Ducobu, J., "The endocannabinoid system and the regulation of the metabolism", Article De Synthese, Rev Med Brux, vol. 26, pp. 159-164 (Abstract Only).
Eckardt, K., et al., "Cannabinoid type 1 receptors in human skeletol muscle cells participate in the negative crosstalk between fat and muscle", Diabetologia, Published Online Dec. 17, 2008, vol. 52, pp. 664-674.
Gye, M.C. et al., "Postnatal changes in the calcium binding proteins of mouse testis", Archives of Andrology, Journal of Reproductive Systems, Published online Jul. 9, 2009, vol. 46, No. 1, pp. 51-57.
Hoehe, M.R., et al., "Genetic and Physical Mapping of the Human Cannabinoid Receptor Gene to Chromosome 6q14-q15", The New Biologist, Sep. 1991, vol. 3, No. 9, pp. 880-885.
Hongwu Wang et al., "Identification of Novel Cannabinoid CB1 Receptor Antagonists by Using Virtual Screening with a Pharmacophore Model", Journal of Medicinal Chemistry, Apr. 1, 2008, vol. 51, No. 8, pp. 2439-2446, XP055232708.

Iannotti, F.A., et al., "The endocannabinoid 2-AG control skeletal muscle cell differentiation via CB1 receptor-dependent inhibition of Kv7 channels", Proc. Natl. Acad. Sci. USA, Jun. 2014, vol. 117, pp. 2472-2481.
International Search Report for Application No. PCT/EP2016/072735 dated Nov. 30, 2016.
Izzo, A.A., et al., "Cannabinoid CB1-receptor mediated regulation of gastrointestinal motility in mice in a model of intestinal inflammation", British Journal of Pharmacology, Jul. 18, 2001, vol. 134, No. 3, pp. 563-570.0.
Izzo, A.A., et al., "Cannabinoids and the gut: New developments and emerging concepts", Pharmacology & Therapeutics, Elsevier, 2010, vol. 126, pp. 21-38.
Izzo, A.A., et al., "Inhibitory effect of cannabinoid agonists on gastric emptying in the rat", Naunyn-Schmiedeberg's Arch Pharamacol, Published online Jul. 13, 1999, vol. 360, pp. 221-223.
Jarrahpour, A., et al. "Diastereoselective synthesis of potent antimalarial cis-β-lactam agents through a [2+2] cycloaddition of chiral imines with a chiral ketene", European Journal of Medicinal Chemistry, Sep. 28, 2014, vol. 87, pp. 364-371.
Jensen, M.D., "What is the Potential Role of Cannabinoid-1 Receptor Blockade in Glucose and Lipid Management?", The American Journal of Medicine, Sep. 2007, vol. 120, No. 9A, pp. S25-S32.
Jeong, Won-Il et al., "Paracrine Activation of Hepatic CB1 Receptors by Stellate Cell-Derived Endocannabinoids Mediates Alcoholic Fatty Liver", Cell Metabolism, Article, Mar. 2008, vol. 7, pp. 227-235.
Jourdan et al., "Antagonism of Peripheral Hepatic Cannabinoid Receptor-1 Improves Liver Lipid Metabolism in Mice: Evidence From Cultured Explants", Hepatology, vol. 55, No. 3, pp. 790-799.
Jourdan et al., "CB1 Antagonism Exerts Specific Molecular Effects on Visceral and Subcutaneous Fat and Reverses Liver Steatosis in Diet-Induced Obese Mice", Diabetes, Apr. 2010, vol. 59, pp. 926-934.
Jourdan et al., "Overactive cannabinoid 1 receptor in podocytes drives type 2 diabetic nephropathy", Proc. Natl. Acad. Sci. USA, Nov. 14, 2014, vol. 111, No. 5, pp. E5420-E5428.
Lafontan, M. et al., "Effects of CB1 antagonist on the control of metabolic functions in obese type 2 diabetic patients", Diabetes & Metabolism, Science Direct, Feb. 5, 2007, vol. 33, pp. 85-95.
Lecru, L., et al., "Cannabinoid receptor 1 is a major mediator of renal fibrosis", Kidney International, 2015, vol. 88, pp. 72-84.
Lehmann, A., et al., "Cannabinoid Receptor Agonism Inhibits Transient Lower Esophageal Sphincter Relaxations and Reflux in Dogs", Gastroenterology, Mar. 14, 2002, vol. 123, No. 4, pp. 1129-1134.
Liu, J. et al., "Hepatic Cannabinoid Receptor-1 Mediates Diet-Induced Insulin Resistance via Inhibition of Insulin Signaling and Clearance in Mice", Gastroenterology, Jan. 24, 2012, vol. 142, pp. 1218-1228.
Liu, J. et al., "Lipopolysaccharide Induces Anandamide Synthesis in Macrophages via CD14/MAPK/Phosphoinositide 3-Kinase/NF-kB Independently of Platelet-activating Factor*", The Journal of Biological Chemistry, Nov. 7, 2003, vol. 278, No. 5, pp. 45034-45039.
Maccarrone, M. et al., "Endocannabinoid signaling at the periphery: 50 years after THC", Trends Pharmacol Sci., May 2015, vol. 36, No. 5, pp. 277-296.
Massa, F. et al., "The endogenous cannabinoid system protects against colonic inflammation", The Journal of Clinical Investigation, Apr. 2004, vol. 113, No. 8, pp. 1202-1209.
Matias, I. et al., "Regulation, Function, and Dysregulation of Endocannabinoids in Models of Adipose and β-Pancreatic Cells and in Obesity and Hyperglycemia", The Journal of Clinical Endocrinology & Metabolism, Aug. 2006, vol. 91, No. 8, pp. 3171-3180.
Mehta, P.D. et al., "2-Azetidinone—A new profile of various pharmacological activities", European Journal of Medicinal Chemistry, Sep. 27, 2010, vol. 45, pp. 5541-5560.
Montecucco, F. et al., "At the heart of the matter: the endocannabinoid system in cardiovascular function and dysfunction", Trends in Pharmacological Sciences, Jun. 2012, vol. 33, No. 6.

(56) References Cited

OTHER PUBLICATIONS

Nogueiras, R. et al., "Peripheral, but Not Central, CB1 Antagonism Provides Food Intake-, pgs Independent Metabolic Benefits in Diet-Induced Obese Rats", Diabetes, Nov. 2008, vol. 57, pp. 2977-2991.

O'Boyle, N.M. et al., "Synthesis, evaluation and structural studies of antiproliferative tubulin-targeting azetidin-2-ones", Bioorganic & Medicinal Chemistry, Feb. 17, 2011, vol. 19, pp. 2306-2325.

O'Boyle, N.M. et al., "β-Lactam Estrogen Receptor Antagonists and a Dual-Targeting Estrogen Receptor/Tubulin Ligand", Journal of Medicinal Chemistry, Nov. 4, 2014, vol. 57, pp. 9370-9382.

Osei-Hyiaman, D. et al., "Endocannabinoid activation at hepatic CB1 receptors stimulates fatty acid synthesis and contributes to diet-induced obesity", The Journal of Clinical Investigation, May 2005, vol. 115, No. 5, pp. 1298-1305.

Osei-Hyiaman, D. et al., "Hepatic CB1 receptor is required for development of diet-induced steatosis, dyslipidemia, and insulin and leptin resistance in mice", The Journal of Clinical Investigation, Sep. 2008, vol. 118, No. 9, pp. 3160-3169.

Pacher, P. et al., "Modulating the endocannabinoid system in human health and disease: success and failures", FEBS J., May 2013, vol. 280, No. 9, pp. 1918-1943.

Pertwee, R.G., "Cannabinoid receptors and pain", Progess in Neurobiology, vol. 63, pp. 569-611.

Rajesh, M., "Cannabinoid 1 Receptor Promotes Cardiac Dysfunction, Oxidative Stress, Inflammation, and Fibrosis in Diabetic Cardiomyopathy", Diabetes, Mar. 2012, vol. 61, pp. 716-727.

Ravient Trillou, C. et al., "Anti-obesity effect of SR141716, a CB1 receptor antagonist, in diet-induced obese mice", Am J Physiol Integr Comp Physiol, Oct. 24, 2002, vol. 284, No. 2, pp. R345-R353.

Rinaldi-Carmona, M. et al., "Characterization of Two Cloned Human CB1 Cannabinoid Receptor Isoforms", The Journal of Pharmacology and Experimental Therapeutics, Nov. 10, 1995, vol. 278, No. 2, pp. 871-878.

* cited by examiner

1,4-DI-(4-METHYLTHIOPHENYL)-3-PHTALOYLAZETIDINE-2-ONE AND THE DERIVATIVES THEREOF

CROSS REFERENCE TO RELATED APPLICATIONS

The present application is a national phase entry under 35 U.S.C. § 371 of International Application No. PCT/EP2016/072735 filed Sep. 23, 2016, published in French, which claims priority from French Patent Application No. 1559067 filed Sep. 25, 2015, all of which are incorporated herein by reference.

INTRODUCTION

The present invention relates to the compound 1,4-di-(4-methylthiophenyl)-3-phthaloylazetidine-2-one and its derivatives, their synthesis process and their uses, in particular their therapeutic use, especially in the treatment of pathologies associated with hyperactivity of the endocannabinoid system, as well as their use for purely aesthetic purposes, especially for enabling weight loss.

The endocannabinoid system (ECS) is a complex system which comprises the cannabinoid receptors, their endogenous ligands (i.e., the endocannabinoids AEA and 2-AG, more commonly known as anandamide and 2-arachidonoylglycerol, respectively) and numerous metabolic enzymes that catalyse endocannabinoid formation and degradation. It is now well-accepted that endocannabinoids are produced "on demand" from membrane lipid precursors, and that their biological effects are relayed more particularly by two G-protein-coupled receptors possessing seven transmembrane domains, namely the CB1 and/or CB2 receptors.

The latter are present in many organs and tissues of the human body: indeed, in addition to the brain and the immune system, where their expression is predominant, the CB1 and CB2 receptors have been identified in, inter alia, intestine (Di Carlo et al., 2003), bladder (Pertwee, 2001), adipose tissue (Cota et al., 2003), liver (Osei-Hyiaman et al., 2005), testis (Gye et al., 2001), uterus (Das et al., 1995), retina (Buckley et al., 1998), vascular endothelium (Liu et al., 2003), and muscle.

By virtue of their vast presence in tissue, these receptors are involved in the regulation of many biological functions, but also in a wide variety of physiopathological processes. Dysregulation of the endocannabinoid system resulting from altered expression of the endocannabinoid CB1 and/or CB2 receptors or of enzymes that metabolize endocannabinoids and/or that are involved in the endocannabinoid synthesis pathways have indeed been observed in a myriad of pathologies. Among these, obesity and associated metabolic disorders, diabetes and its complications, liver, kidney and cardiovascular disease, osteoporosis, cancer and fertility problems are associated with hyperactivity of the endocannabinoid system, while inflammatory bowel disease and mental and neurodegenerative illnesses are associated with underactivity of said system (Di Marzo, 2008; Izzo et al., 2010; Pacher et al., 2013; Maccarone et al., 2015).

In the case of obesity, it has been clearly established that hyperactivation of the endocannabinoid system leads to stimulation of the appetite, and thus promotes weight gain, while altering metabolic parameters such as blood insulin, insulin resistance, blood glucose, blood lipids, etc. (Ravinet Trillou C. et al., 2003; Di Marzo and Matias, 2005; Despres and Lemieux, 2006).

Various therapeutic strategies aimed at correcting this endocannabinoid system dysregulation, by acting directly on the mediators of this system, namely the CB1 and/or CB2 receptors, have consequently been developed and extensively described in the scientific literature.

It has been shown, for example, that activation of the endocannabinoid system using CB1 receptor agonists makes it possible to induce transient relaxation of the oesophagus, and thus to treat gastro-oesophageal reflux (Beaumont et al., 2009; Lehman et al., 2002), and also to improve the symptoms associated with intestinal diseases such as irritable bowel syndrome or gastric ulcers, while acting especially on gastrointestinal motility and inflammation (Izzo et al., 2001; Izzo et al., 1999; Massa et al., 2004).

The use of compounds which antagonize the action of the CB1 receptor, such as rimonabant, have been shown effective in the treatment of obesity and of metabolic syndrome, by acting not only centrally on food intake, but also peripherally on hyperinsulinaemia, insulin resistance, hyperglycaemia and dyslipidaemia, thus making it possible also to reduce the associated cardiovascular risks (Ravinet Trillou C. et al., 2003; Tam et al., 2010; Tam et al., 2012).

Beneficial effects of an antagonistic action directed against the CB1 receptor has also been observed within the context of diabetes and its complications (nephropathies, tubulopathies) (Jourdan et al., 2014), and of the development of fibrosis, in particular liver fibrosis and renal fibrosis (Teixeira-Clerc et al., 2006).

Agonists and antagonists of the cannabinoid receptors, in particular of the CB1 receptors, are thus of major therapeutic interest in diseases involving dysregulation of the endocannabinoid system.

Nevertheless, significant side effects have been observed following the extended use of these molecules, in particular when they cross the blood-brain barrier. Among these molecules, rimonabant, initially intended to treat obesity, had to be withdrawn from the market in 2008 because of the depressogenic psychiatric effects caused by its action on central CB1 receptors.

There is thus a need to develop novel CB1 receptor inhibitors, which diffuse little or not at all in the central nervous system, in order to limit, or even to completely abolish, these deleterious psychotropic effects.

The present invention proposes to satisfy this need using novel compounds acting on the peripheral CB1 receptors.

The Inventors have indeed surprisingly discovered that the compound 1,4-di-(4-methylthiophenyl)-3-phthaloylazetidine-2-one and its structural analogues have physicochemical features that give them a pharmacokinetic profile that induces a preferential inverse agonist activity on the peripheral CB1 receptors. The experimental data disclosed hereinafter further shows that these molecules exert beneficial effects not only on carbohydrate and lipid metabolism, on glucose tolerance, insulin sensitivity and body mass in obese mice, but also on gastrointestinal motility, and this with no liver toxicity. These novel compounds thus open the way to novel therapeutic strategies not only for obesity-related metabolic disorders and defects in gastrointestinal motor function, but also for all diseases associated with hyperactivity of the endocannabinoid system involving preferentially the CB1 receptors.

Consequently, the present invention proposes a selective inverse agonist of peripheral CB1 receptors of formula (I) as defined below relating to 1,4-di-(4-methylthiophenyl)-3-phthaloylazetidine-2-one and to its derivatives, its synthesis process, and its applications, especially therapeutic and non-therapeutic.

DETAILED DESCRIPTION OF THE INVENTION

The present invention thus first relates to a compound of the following general formula (I):

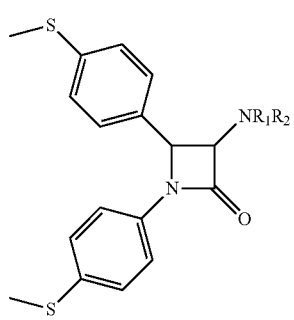

(I)

wherein:
- $R_1$ and $R_2$, which can be identical or different, represent a hydrogen atom or a $COR_3$, $SO_2R_4$ or $CONR_5R_6$ group; or form together with the nitrogen atom that bears them a 5- or 6-member heterocycle comprising at least one additional heteroatom, C=O group, aryl group or heteroaryl group;
- $R_3$, $R_4$, $R_5$ and $R_6$ independently represent a hydrogen atom, or an aryl or heteroaryl group, said group being optionally substituted by one or more groups selected from a halogen atom, $OR_7$, $NR_8R_9$, $SR_{10}$, $S(O)R_{11}$, $SO_2R_{12}$, $SO_2NR_{13}R_{14}$, $OCOR_{15}$, $NR_{16}COR_{17}$, $NR_{18}C(O)OR_{19}$, $CO_2R_{20}$, $CONR_{21}R_{22}$, $OCO_2R_{23}$, $OCONR_{24}R_{25}$, $COR_{26}$, nitro ($NO_2$), cyano (CN), oxo (=O) and $CF_3$; and
- $R_7$ to $R_{26}$ independently represent a hydrogen atom or a ($C_1$-$C_6$)alkyl, aryl or aryl-($C_1$-$C_6$)alkyl group, or a pharmaceutically acceptable salt and/or solvate thereof.

The stereoisomers of the compounds of general formula (I) also form part of the present invention, especially the trans diastereoisomer, as well as their mixtures.

Within the meaning of the present invention, "stereoisomer" refers to a geometric isomer (or configurational isomer) or an optical isomer.

Geometric isomers result from the different position of the substituents on a double bond or a ring which can thus have a Z or E configuration, also called cis or trans.

Optical isomers result in particular from the different position in space of the substituents on a carbon atom comprising four different substituents. This carbon atom thus constitutes a chiral or asymmetric centre. Optical isomers include diastereoisomers and enantiomers. Optical isomers that are mirror images of each other but are non-superposable are called "enantiomers". Optical isomers that are not superposable mirror images of each other are called "diastereoisomers".

A mixture containing equal amounts of two individual enantiomer forms of opposite chirality is called a "racemic mixture".

The tautomers of the compounds of general formula (I) also form part of the present invention.

Within the meaning of the present invention, "tautomer" refers to a constitutional isomer of the compound obtained by prototropy, i.e., by migration of a hydrogen atom and change in the location of a double bond. The different tautomers of a compound are generally interconvertible and present in equilibrium in solution, in proportions which can vary according to the solvent used, the temperature or the pH.

In the present invention, "pharmaceutically acceptable" is intended to mean that which is useful in the preparation of a pharmaceutical composition that is generally safe, non-toxic and neither biologically nor otherwise undesirable and that is acceptable for veterinary as well as human pharmaceutical use.

By "pharmaceutically acceptable salt" of a compound is meant a salt that is pharmaceutically acceptable, as defined herein, and that has the desired pharmacological activity of the parent compound.

The pharmaceutically acceptable salts include in particular:

(1) pharmaceutically acceptable acid addition salts formed with pharmaceutically acceptable inorganic acids such as hydrochloric acid, hydrobromic acid, sulphuric acid, nitric acid, phosphoric acid and the like; or formed with pharmaceutically acceptable organic acids such as acetic acid, benzenesulphonic acid, benzoic acid, camphosulphonic acid, citric acid, ethanesulphonic acid, fumaric acid, glucoheptonic acid, gluconic acid, glutamic acid, glycolic acid, hydroxynaphthoic acid, 2-hydroxyethanesulphonic acid, lactic acid, maleic acid, malic acid, mandelic acid, methanesulphonic acid, muconic acid, 2-naphthalenesulphonic acid, propionic acid, salicylic acid, succinic acid, dibenzoyl-L-tartaric acid, tartaric acid, p-toluenesulphonic acid, trimethylacetic acid, trifluoroacetic acid and the like, and (2) the pharmaceutically acceptable base addition salts formed when an acidic proton present in the parent compound is either replaced by a metal ion, for example an alkali metal ion, an alkaline-earth metal ion or an aluminium ion; or coordinated with a pharmaceutically acceptable organic base such as diethanolamine, ethanolamine, N-methylglucamine, triethanolamine, tromethamine and the like; or with a pharmaceutically acceptable inorganic base such as aluminium hydroxide, calcium hydroxide, potassium hydroxide, sodium carbonate, sodium hydroxide and the like.

It can be a sodium salt when the compound comprises an acid function.

These salts can be synthesized from the compounds of the invention containing a basic or acidic moiety and the corresponding acids or bases according to conventional chemical methods.

The pharmaceutically acceptable solvates of the compounds of the present invention include conventional solvates such as those formed during the last preparation step of the compounds of the invention due to the presence of solvents. By way of example, mention may be made of the solvates due to the presence of water (hydrates) or of ethanol.

The term "halogen" refers to fluorine, chlorine, bromine or iodine.

Within the meaning of the present invention, "($C_1$-$C_6$) alkyl" group refers to a linear or branched, saturated hydrocarbon chain comprising 1 to 6, especially 1 to 4, carbon atoms. By way of example, mention may be made of the following groups: methyl, ethyl, propyl, isopropyl, butyl, isobutyl, sec-butyl, tert-butyl, pentyl or hexyl.

Within the meaning of the present invention, "aryl" refers to an aromatic hydrocarbon group, preferably comprising from 6 to 10 carbon atoms, and comprising one or more fused rings, such as a phenyl or naphthyl group, for example. Advantageously, it is phenyl.

Within the meaning of the present invention, "aryl-($C_1$-$C_6$)alkyl" refers to an aryl group as defined above, attached to the rest of the molecule via a ($C_1$-$C_6$)alkyl chain as defined above. By way of example, mention may be made of the benzyl group.

Within the meaning of the present invention, "heteroaryl" refers to an aryl group as defined above, wherein 1 to 4, in particular 1 or 2, carbon atoms are each independently replaced by a heteroatom selected from N, O and S.

According to a particular embodiment of the invention, $R_1$ and $R_2$ form together with the nitrogen atom which bears them a 5- or 6-member heterocycle comprising at least one, preferably one or two, additional heteroatom, especially one or two nitrogen atom(s) (N), C=O group, aryl group, especially phenyl, or heteroaryl group, especially pyridine.

Preferably, $R_1$ and $R_2$ form together with the nitrogen atom which bears them a heterocycle of following formula (II) or (III):

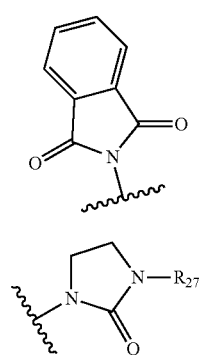

wherein $R_{27}$ represents a hydrogen atom or a $COR_3$ or $SO_2R_4$ group, $R_3$ and $R_4$ being as defined in claim 1, in particular $R_{27}$ represents a hydrogen atom.

According to another particular embodiment of the invention:

$R_1$ and $R_2$, which can be identical or different, represent a hydrogen atom or a $COR_3$, $SO_2R_4$ or $CONR_5R_6$ group; and $R_3$, $R_4$, $R_5$ and $R_6$ independently represent a hydrogen atom, or an aryl, preferably a phenyl, or heteroaryl group, such as a pyridine, said group being optionally substituted by one or more groups selected from a halogen atom, $OR_7$, $NR_8R_9$, $SR_{10}$, $S(O)R_{11}$, $SO_2R_{12}$, $SO_2NR_{13}R_{14}$, $OCOR_{15}$, $NR_{16}COR_{17}$, $NR_{18}C(O)OR_{19}$, $CO_2R_{20}$, $CONR_{21}R_{22}$, $OCO_2R_{23}$, $OCONR_{24}R_{25}$, $COR_{26}$, nitro ($NO_2$), cyano (CN) and $CF_3$, advantageously a halogen atom, $OR_7$, $NR_8R_9$, $SR_{10}$, $S(O)R_{11}$, $SO_2R_{12}$, $OCOR_{15}$, $CO_2R_{20}$, $OCO_2R_{23}$, $COR_{26}$, nitro ($NO_2$), cyano (CN) and $CF_3$, advantageously a halogen atom, $OR_7$, $NR_8R_9$, $SO_2R_{12}$, and $CF_3$; $R_7$ to $R_{26}$ being as defined above.

Preferably:

$R_1$ and $R_2$, which can be identical or different, represent a hydrogen atom or a $COR_3$, $SO_2R_4$ or $CONR_5R_6$ group;

$R_3$, $R_4$ and $R_5$ independently represent an aryl group, preferably a phenyl, optionally substituted by a group selected from a halogen atom, $OR_7$, $NR_8R_9$, $SR_{10}$, $S(O)R_{11}$, $SO_2R_{12}$, $SO_2NR_{13}R_{14}$, $OCOR_{15}$, $NR_{16}COR_{17}$, $NR_{18}C(O)OR_{19}$, $CO_2R_{20}$, $CONR_{21}R_{22}$, $OCO_2R_{23}$, $OCONR_{24}R_{25}$, $COR_{26}$, nitro ($NO_2$), cyano (CN) and $CF_3$, advantageously a halogen atom, $OR_7$, $NR_8R_9$, $SR_{10}$, $S(O)R_{11}$, $SO_2R_{12}$, $OCOR_{15}$, $CO_2R_{20}$, $OCO_2R_{23}$, $COR_{26}$, nitro ($NO_2$), cyano (CN) and $CF_3$, advantageously a halogen atom, $OR_7$, $NR_8R_9$, $SO_2R_{12}$, and $CF_3$, $R_7$ to $R_{26}$ being as defined above; and $R_6$ represents a hydrogen atom.

Preferably, $R_1$ is a hydrogen atom and $R_2$ represents a $COR_3$, $SO_2R_4$ or $CONR_5R_6$ group, with $R_3$, $R_4$, $R_5$ and $R_6$ being as defined above.

According to another preferred embodiment of the invention, $R_1$ is a hydrogen atom and $R_2$ represents a $COR_3$ group, $R_3$ being an aryl, preferably a phenyl, optionally substituted by a group selected from a halogen atom, $OR_7$, $NR_8R_9$, $SR_{10}$, $S(O)R_{11}$, $SO_2R_{12}$, $SO_2NR_{13}R_{14}$, $OCOR_{15}$, $NR_{16}COR_{17}$, $NR_{18}C(O)OR_{19}$, $CO_2R_{20}$, $CONR_{21}R_{22}$, $OCO_2R_{23}$, $OCONR_{24}R_{25}$, $COR_{26}$, nitro ($NO_2$), cyano (CN) and $CF_3$, advantageously a halogen atom, $OR_7$, $NR_8R_9$, $SR_{10}$, $S(O)R_{11}$, $SO_2R_{12}$, $OCOR_{15}$, $CO_2R_{20}$, $OCO_2R_{23}$, $COR_{26}$, nitro ($NO_2$), cyano (CN) and $CF_3$, advantageously a halogen atom, $OR_7$, $NR_8R_9$, $SO_2R_{12}$, and $CF_3$, advantageously a halogen atom, $SO_2CH_3$, and $CF_3$, $R_7$ to $R_{26}$ being as defined above.

According to another particular embodiment of the invention, $R_1$ is a hydrogen atom and $R_2$ represents an $SO_2R_4$ group, $R_4$ being an aryl, preferably a phenyl, optionally substituted by a group selected from a halogen atom, $OR_7$, $NR_8R_9$, $SR_{10}$, $S(O)R_{11}$, $SO_2R_{12}$, $SO_2NR_{13}R_{14}$, $OCOR_{15}$, $NR_{16}COR_{17}$, $NR_{18}C(O)OR_{19}$, $CO_2R_{20}$, $CONR_{21}R_{22}$, $OCO_2R_{23}$, $OCONR_{24}R_{25}$, $COR_{26}$, nitro ($NO_2$), cyano (CN) and $CF_3$, advantageously a halogen atom, $OR_7$, $NR_8R_9$, $SR_{10}$, $S(O)R_{11}$, $SO_2R_{12}$, $OCOR_{15}$, $CO_2R_{20}$, $OCO_2R_{23}$, $COR_{26}$, nitro ($NO_2$), cyano (CN) and $CF_3$, advantageously a halogen atom, $OR_7$, $NR_8R_9$, $SO_2R_{12}$, and $CF_3$, advantageously a halogen atom, $SO_2CH_3$, and $CF_3$, $R_7$ to $R_{26}$ being as defined above.

According to another particular embodiment of the invention, $R_1$ is a hydrogen atom and $R_2$ represents a $CONR_5R_6$ group, $R_6$ being a hydrogen atom and $R_5$ being an aryl, preferably a phenyl, optionally substituted by a group selected from a halogen atom, $OR_7$, $NR_8R_9$, $SR_{10}$, $S(O)R_{11}$, $SO_2R_{12}$, $SO_2NR_{13}R_{14}$, $OCOR_{15}$, $NR_{16}COR_{17}$, $NR_{18}C(O)OR_{19}$, $CO_2R_{20}$, $CONR_{21}R_{22}$, $OCO_2R_{23}$, $OCONR_{24}R_{25}$, $COR_{26}$, nitro ($NO_2$), cyano (CN) and $CF_3$, advantageously a halogen atom, $OR_7$, $NR_8R_9$, $SR_{10}$, $S(O)R_{11}$, $SO_2R_{12}$, $OCOR_{15}$, $CO_2R_{20}$, $OCO_2R_{23}$, $COR_{26}$, nitro ($NO_2$), cyano (CN) and $CF_3$, advantageously a halogen atom, $OR_7$, $NR_8R_9$, $SO_2R_{12}$, and $CF_3$, advantageously a halogen atom, $SO_2CH_3$, and $CF_3$, $R_7$ to $R_{26}$ being as defined above.

The compounds of the present invention can more preferably be selected from compounds IA to IF described hereinafter, and their pharmaceutically acceptable salts and/or solvates:

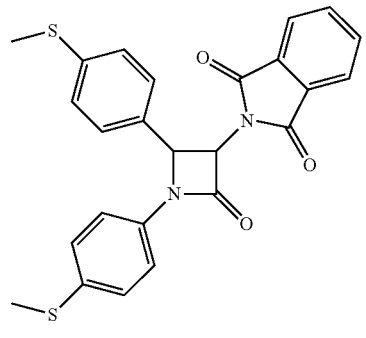 [SMILES: CSc1ccc(C2C(N3C(=O)c4ccccc4C3=O)C(=O)N2c2ccc(SC)cc2)cc1]

Compound (IA)

JM-00.266

Compound (IB)

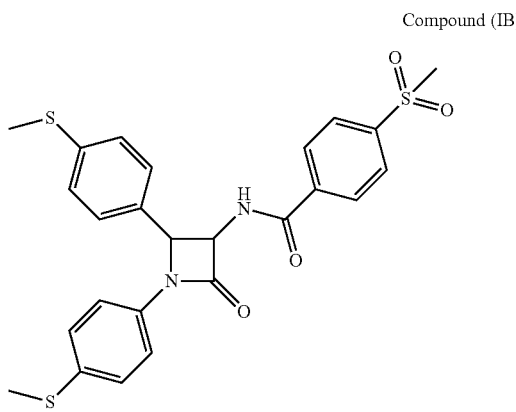

Compound (IC)

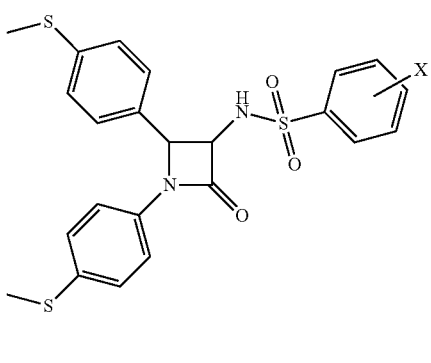

Compound (ID)

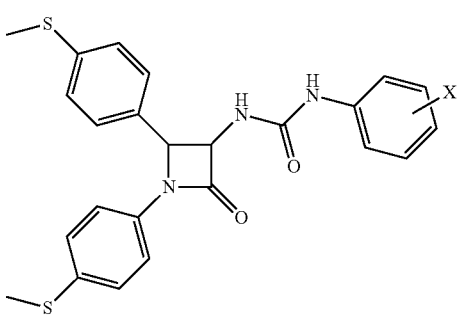

Compound (IE)

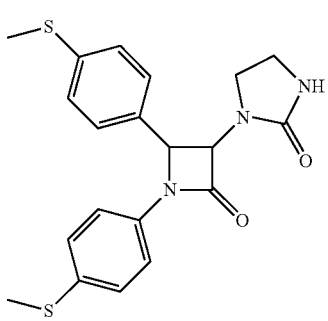

Compound (IF)

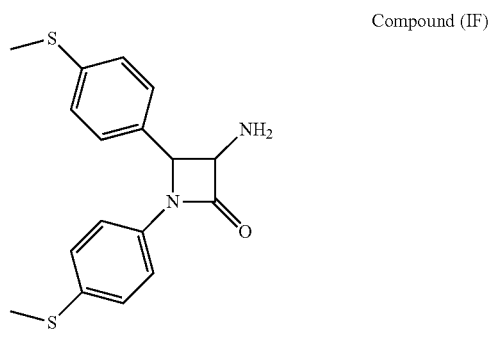

wherein X represents a hydrogen atom, a halogen or CF$_3$.

According to a more particularly preferred embodiment of the invention, the compound of formula (I) according to the invention is the compound of formula (IA):

(IA)

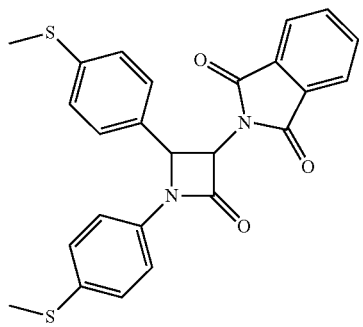

or a pharmaceutically acceptable salt and/or solvate thereof.

The present invention also relates to the processes for preparing the compounds of formula (I) according to the invention.

A process for preparing a compound of formula (I) according to the invention comprises the following steps:

(i) condensation of 4-methylthiobenzaldehyde with 4-methylthioaniline to obtain the compound of following formula (IV):

(IV)

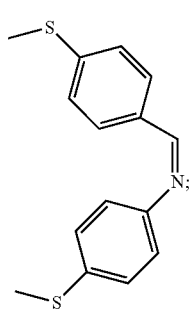

(ii) Staudinger cycloaddition between the compound of formula (IV) obtained and a ketene of following formula (V):

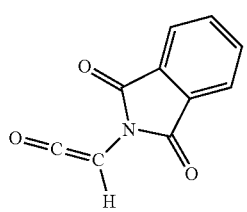

to obtain the compound of following formula (IA):

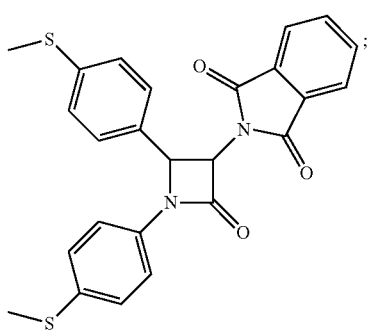

(iii) optionally, deprotection of the phthaloylated amine function of the compound of formula (IA), preferably by action of methylhydrazine, to obtain the compound of following formula (IF):

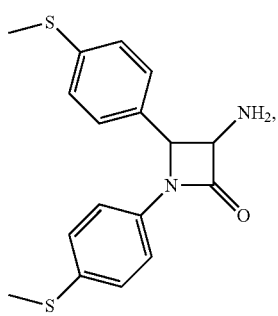

then, optionally, coupling of the compound of formula (IF) thus obtained with a compound of formula $R_1$—X and/or $R_2$—X', wherein $R_1$—X and $R_2$—X' are activated forms, such as acyl chlorides, sulphonyl chlorides and aryl isocyanates, of groups $R_1$ and $R_2$ as defined above; and (iv) collection of the compound obtained in step (ii) or in step (iii).

By way of example of acyl chlorides in step (ii), according to a particular embodiment phthaloylglycinyl chloride can be used.

According to a preferred embodiment, the process of the invention relates to the preparation a compound of formula (IA):

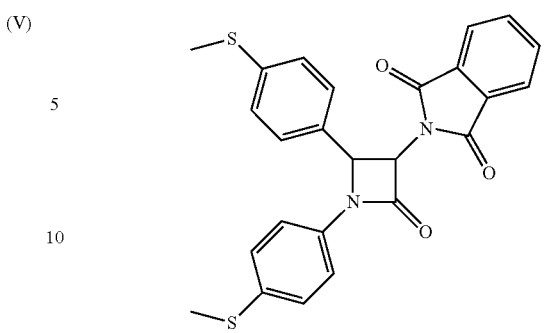

corresponding to a compound of formula (I) wherein $R_1$ and $R_2$ form together with the nitrogen atom which bears them a heterocycle of formula (II).

This process comprises the following steps:

(i) condensation of 4-methylthiobenzaldehyde with 4-methylthioaniline to obtain the compound of following formula (IV):

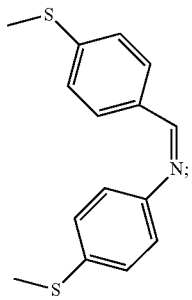

(ii) Staudinger cycloaddition between the compound of formula (IV) obtained in step (i) and a ketene of following formula (V):

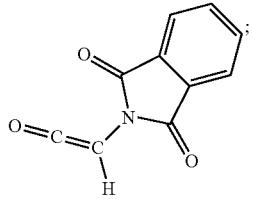

then collection of the compound of formula (IA).

The condensation reaction (intermolecular dehydration) will be carried out advantageously in the presence of a solvent such as toluene, and of a drying agent produced during the reaction, such as anhydrous sodium sulphate.

Staudinger cycloaddition, also called ketene-imine [2+2] cycloaddition, is a chemical reaction known to the person skilled in the art. This reaction can be carried out in dichloroethane (DCE), at room temperature and under inert atmosphere such as under nitrogen or under argon, preferably under nitrogen.

The ketene (V) can advantageously be generated in situ by action of a base such as triethylamine (TEA) on the acid chloride of phthaloylglycine. This acid chloride can be obtained by methods known to the person skilled in the art, especially either externally by action of thionyl chloride on commercial N-phthaloylglycine or directly in the reaction mixture by means of a coupling agent such as phenyl dichlorophosphate, in the presence of a proton acceptor such as triethylamine.

Such a process is illustrated in greater detail in following scheme 1.

This process thus makes it possible to obtain compound (IA) which can serve as starting reagent in the preparation process of the other compounds of formula (I).

The present invention also relates to a process for preparing compounds of formula (I), using as starting product the compound of formula (IA) and comprising the following steps:

(i) condensation of 4-methylthiobenzaldehyde with 4-methylthioaniline to obtain the compound of formula (IV);

(ii) Staudinger cycloaddition between the compound of formula (IV) obtained in step (i) and a ketene of formula (V);

(iii) deprotection of the phthaloylated amine function of the compound of formula (IA) obtained in step (ii), preferably by action of methylhydrazine, to obtain the compound of following formula (IF):

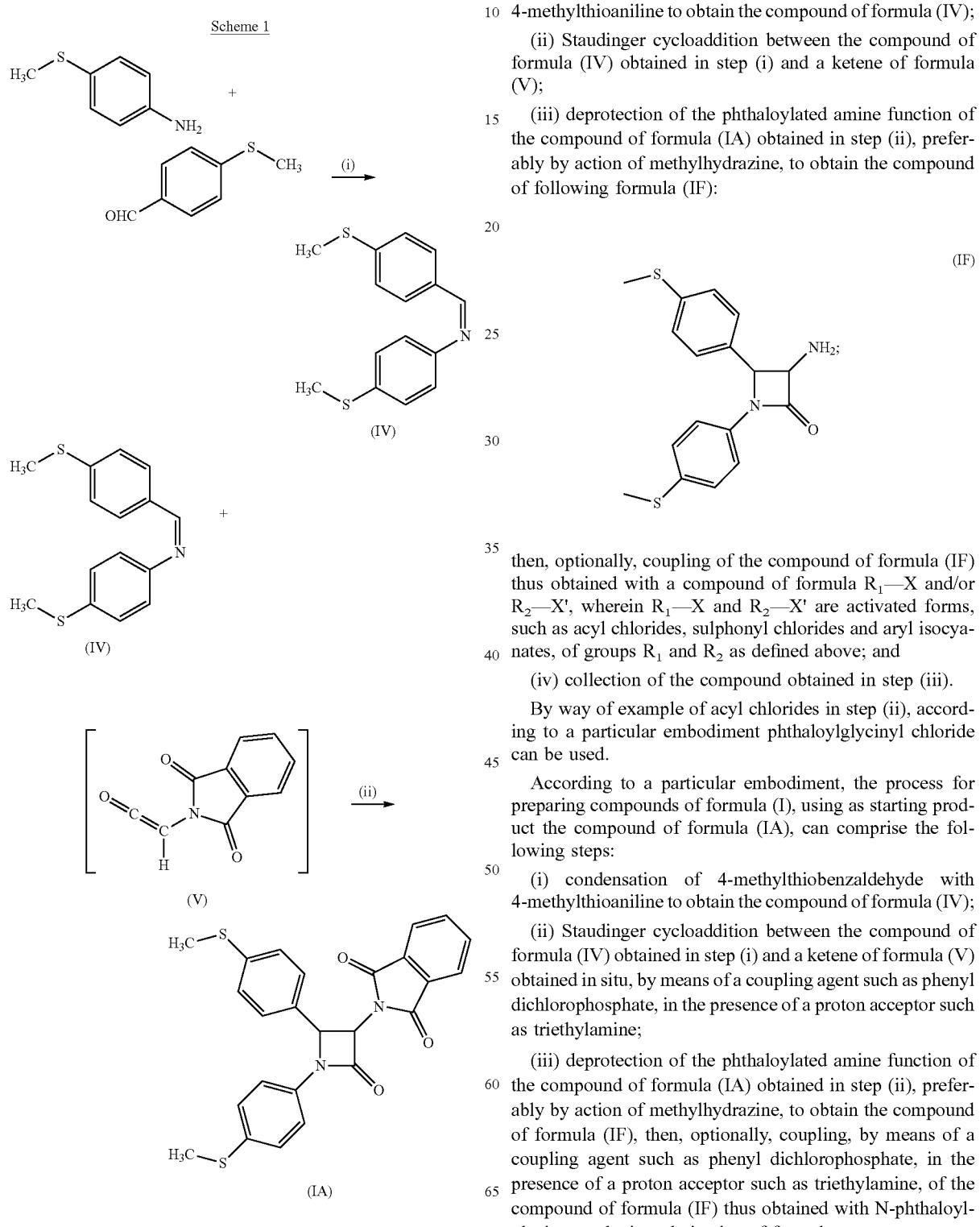

then, optionally, coupling of the compound of formula (IF) thus obtained with a compound of formula $R_1$—X and/or $R_2$—X', wherein $R_1$—X and $R_2$—X' are activated forms, such as acyl chlorides, sulphonyl chlorides and aryl isocyanates, of groups $R_1$ and $R_2$ as defined above; and (iv) collection of the compound obtained in step (iii).

By way of example of acyl chlorides in step (ii), according to a particular embodiment phthaloylglycinyl chloride can be used.

According to a particular embodiment, the process for preparing compounds of formula (I), using as starting product the compound of formula (IA), can comprise the following steps:

(i) condensation of 4-methylthiobenzaldehyde with 4-methylthioaniline to obtain the compound of formula (IV);

(ii) Staudinger cycloaddition between the compound of formula (IV) obtained in step (i) and a ketene of formula (V) obtained in situ, by means of a coupling agent such as phenyl dichlorophosphate, in the presence of a proton acceptor such as triethylamine;

(iii) deprotection of the phthaloylated amine function of the compound of formula (IA) obtained in step (ii), preferably by action of methylhydrazine, to obtain the compound of formula (IF), then, optionally, coupling, by means of a coupling agent such as phenyl dichlorophosphate, in the presence of a proton acceptor such as triethylamine, of the compound of formula (IF) thus obtained with N-phthaloylglycine to obtain a derivative of formula

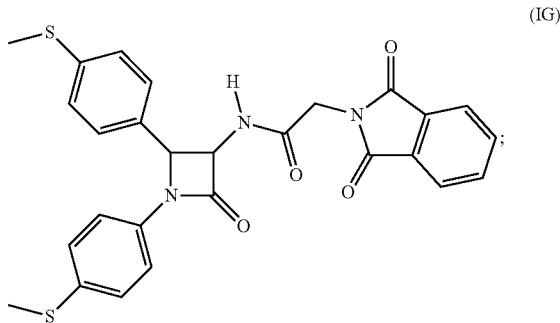 [SMILES: CSc1ccc(C2C(NC(=O)CN3C(=O)c4ccccc4C3=O)C(=O)N2c2ccc(SC)cc2)cc1]

and (iv) collection of the compound obtained in step (ii) or in step (iii).

Thus, another aspect of the invention relates to a derivative/analogue of compound (IA) of formula (IG):

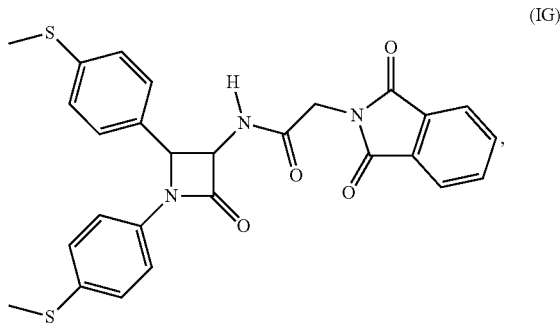 [SMILES: CSc1ccc(C2C(NC(=O)CN3C(=O)c4ccccc4C3=O)C(=O)N2c2ccc(SC)cc2)cc1]

or a pharmaceutically acceptable salt and/or solvate thereof.

The deprotection reaction of the phthaloylated amine function of compound (IA) is a typical reaction, well-known to the person skilled in the art. This deprotection will be carried out advantageously by action of hydrazine hydrate or of methylhydrazine, preferably of methylhydrazine, on compound (IA), preferably in dichloromethane. This reaction makes it possible to obtain compound (IF) corresponding to a compound of formula (I) wherein $R_1$ and $R_2$ each represents a hydrogen atom.

According to a particular embodiment, compound (IF) is collected directly, without the coupling reaction taking place.

According to another particular embodiment, compound (IF) is used subsequently in the process as synthetic intermediate to prepare compounds of formula (I) other than compound (IA).

The present invention thus also relates to compound (IF) as synthetic intermediate of compounds of formula (I) other than compound (IA).

The coupling reaction can be carried out under experimental conditions well-known to the person skilled in the art, advantageously at room temperature in the presence of a solvent such as dichloroethane, and of a base such as triethylamine (TEA).

Within the meaning of the present invention, "activated form" of a chemical group refers to said chemical group modified so as to make it more active with respect to nucleophiles. These activated forms are well-known to the person skilled in the art and can be in particular an acyl chloride, a sulphonyl chloride or an aryl isocyanate. As example of acyl chloride, phthaloylglycinyl chloride can be used in particular.

The above-described processes can be supplemented, if need be, by any standard manipulations described in the literature, known to the skilled person or exemplified in the experimental section, especially by additional functionalization, cyclization and/or protection/deprotection reactions.

One or more additional salification and/or solvation steps can be carried out at the end of these two processes in order to obtain a pharmaceutically acceptable salt and/or solvate of the compound of formula (I).

The salification step can be carried out under conditions well-known to the person skilled in the art, in the presence of a pharmaceutically acceptable acid or base.

When the compound of formula (I) is in a solvated form, this solvation generally takes place in the last step of the process, the solvent of the solvated form being, in this case, the solvent of the reaction mixture.

The compound of formula (I) obtained by one of these two above-mentioned processes can be separated from the reaction mixture by methods well-known to the person skilled in the art, such as by extraction, solvent evaporation or by precipitation and filtration, for example.

The compound of formula (I) can in addition be purified if need be by techniques well-known to the person skilled in the art, such as by recrystallization if the compound is crystalline, by distillation, by column chromatography on silica gel, or by high-performance liquid chromatography (HPLC).

The Inventors have shown the inverse agonist activity of the compounds of the invention against the peripheral endocannabinoid CB1 receptors, and their interest in the treatment or the prevention of diseases associated with hyperactivity of the endocannabinoid system.

Thus, another aspect of the invention relates to the in vitro use of at least one compound of formula (I) as defined above as inverse agonist of the peripheral endocannabinoid CB1 receptors, preferably as selective inverse agonist of said receptors. In other words, the invention relates to a use of at least one compound of formula (I) to reduce or inhibit the activity of the peripheral endocannabinoid CB1 receptors, preferably in a selective manner.

As used herein, "inverse agonist" refers to a compound that interacts with the same receptor as a natural agonist of this receptor but produces the opposite pharmacological effect and reduces, or inhibits, the activity of said receptor, in particular its basal activity. An inverse agonist is capable of binding to a different binding site than the natural agonist, leading to a conformational change in the receptor and thus preventing binding of the natural agonist. In the context of the present invention, the natural agonists are the endocannabinoids.

As used herein, "selective inverse agonist" refers to an inverse agonist as defined above, which preferentially binds to a single receptor type, without affecting, or minimally affecting, other receptors, in particular the related receptors. In the context of the present invention, the compound of formula (I) according to the invention is an inverse agonist acting selectively on the endocannabinoid CB1 receptors, i.e., binding preferentially to said receptors, but binding not at all or very weakly to the endocannabinoid CB2 receptors.

As used herein, the expression "endocannabinoid CB1 receptors" or "CB1 receptors" refers to the G-protein-coupled receptors possessing seven transmembrane domains, in particular pertussis toxin-sensitive Gi/0-coupled and Gq- and Gs-protein-coupled, capable of interacting with endogenous and exogenous cannabinoids and thus of acting mainly on at least one of the three intracellular signalling pathways of adenylate cyclase, the mitogen-activated protein kinase (MAPK) pathway and certain ion channels. CB1 receptor activity can thus be evaluated in vitro by measuring, for example, cAMP concentrations after contacting the cells with a known agonist of said receptors, such as anandamide (AEA), these concentrations decreasing after the binding of this endocannabinoid to the receptors; such a test is described in the examples described hereinafter. In man, the endocannabinoid CB1 receptor is encoded by the Cnr1 gene, which is located on chromosome 6 at 6q14-q15 (Hoehe et al., 1991), and appears in two isoforms: CB1, which is the major, physiologically active isoform of 472 amino acids; and CB1A, which is a shorter isoform (411 amino acids) whose expression is much lower than that of CB1 (from $\frac{1}{10}$ to $\frac{1}{100}$ depending on the tissue expression site) (Rinaldi-Carmona et al., 1996). To date, the CB1 receptor has also been identified in rats, mice, cats, birds, amphibians and fish, and its protein sequence is highly conserved in vertebrates.

The term "peripheral endocannabinoid CB1 receptors" refers to the CB1 receptors as defined above which are not located in the brain, i.e., centrally. This term is consequently used herein in contrast with the so-called central CB1 receptors, and includes, without limitation, the CB1 receptors expressed in adipose tissue, liver, kidney, the gastrointestinal system, bladder, skeletal muscle, cardiovascular tissues, testis, uterus, the immune system, pancreas, retinal cells, endothelial cells, suprarenal glands, lungs, etc.

The invention also relates to a pharmaceutical composition comprising as active ingredient at least one compound of formula (I) according to the invention, and at least one pharmaceutically acceptable excipient.

As used herein, the expression "pharmaceutically acceptable excipient" refers to a pharmaceutical-grade compound which enhances the delivery, the stability or the bioavailability of an active agent, and which can be metabolized and is nontoxic for a subject to whom it is administered. Preferred excipients according to the invention comprise any one of the excipients commonly used in pharmaceutical products, such as microcrystalline cellulose, lactose, starch, and soya powder.

Said compound of formula (I) is preferably present in the composition according to the invention in an amount sufficient to inhibit peripheral CB1 receptor activity, more particularly within the context of a prophylactic or therapeutic treatment of a disease associated with hyperactivity of the endocannabinoid system. The diseases more particularly concerned are described hereinafter.

Preferably, the composition of the invention comprises from 0.01 wt % to 10 wt %, preferably from 0.02 wt % to 5 wt %, more preferably from 0.05 to 1 wt % of the composition of one or more compounds of formula (I) according to the invention.

The composition according to the invention can be in any of the pharmaceutical forms acceptable in the context of the present invention. For example, the composition can be in a form suitable for oral, sublingual, subcutaneous, intramuscular, intravenous, topical, local, intratracheal, intranasal, transdermal or rectal administration. The most preferred form of the pharmaceutical composition is via the oral route and solid, preferably in capsule or tablet form.

The composition according to the invention can further comprise one or more therapeutic agents, for example for preventing or treating a disease associated with hyperactivity of the endocannabinoid system. The person skilled in the art can easily determine the therapeutic agent that can be combined with the compound of formula (I) of the invention, as a function of the disease to be prevented or treated. By way of illustration, when the disease to be prevented or treated is diabetes and its complications, and/or obesity-related metabolic disorders, said agent can be selected from a hypolipidaemic agent, a hypocholesterolaemic agent, an antidiabetic agent, and/or an anti-obesity agent. The hypolipidaemic and hypocholesterolaemic agents according to the invention include, without limitation, fibrates such as alufibrate, beclobrate, bezafibrate, ciprofibrate, clinofibrate, clofibrate, etofibrate, fenofibrate; statins (HMG-CoA reductase inhibitors) such as atorvastatin, fluvastatin sodium, lovastatin, pravastatin, rosuvastatin, simvastatin, or a compound such as acipimox, aluminium nicotinate, azacosterol, cholestyramine, dextrothyroxine, meglutol, niceritrol, nicoclonate, nicotinic acid, beta-sitosterol, and tiadenol. The antidiabetic agents according to the invention include, without limitation, sulphonylureas, biguanidines, alpha-glucosidase inhibitors, thiazolidinediones, meglitinides such as acarbose, acetohexamide, carbutamide, chlorpropamide, glibenclamide, glibornuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, and voglibose.

The therapeutic agent as described above can also be administered in combination with the compound of formula (I) according to the invention simultaneously, separately, or sequentially. When the compound according to the invention and the therapeutic agent are administered separately or sequentially, they can thus be administered in distinct pharmaceutical forms.

Thus, another aspect of the invention relates to a compound of formula (I) according to the invention and a therapeutic agent as described above, as combined preparation for simultaneous, separate, or sequential administration. In other words, the invention relates to a combined use of the compound of formula (I) according to the invention and of a therapeutic agent as described above for simultaneous, separate, or sequential administration.

The invention also relates to the compound of formula (I) or the pharmaceutical composition as defined above, for use as medicinal product. In other words, the invention relates to the use of said compound of formula (I) or of said pharmaceutical composition as medicinal product.

The invention more particularly relates to the compound of formula (I) or the pharmaceutical composition as defined above for use in the prevention or the treatment of diseases associated with hyperactivity of the endocannabinoid system. In other words, the invention relates to the use of said compound of formula (I) or of said pharmaceutical composition to manufacture a medicinal product for preventing or treating diseases associated with hyperactivity of the endocannabinoid system. More precisely, the invention relates to a method for preventing or treating diseases associated with hyperactivity of the endocannabinoid system, comprising a step of administering an effective amount of the compound of formula (I) or of the composition according to the invention to a subject in need thereof.

As used herein, the terms "prevention" (or "to prevent") and "treatment" (or "to treat") mean, generally, obtaining a desired physiological or pharmacological effect as a function of the degree of severity of the symptoms or of the disease of interest. The effect can be prophylactic in terms of partial or complete prevention of the symptoms or disease ("prevention"), or therapeutic in terms of partial or complete relief from the symptoms or disease ("treatment"). The term "prevention" includes the capacity to avoid or delay the onset or the development of symptoms or of a disease before its onset. The term "treatment", in turn, comprises inhibition of the symptoms or of the disease (i.e., stopping its development), and relief from the symptoms or from the disease (i.e., regression leading to improvement). In the context of the present invention, prevention aims to avoid or to delay the onset of hyperactivity of the endocannabinoid system, whereas treatment aims to make said hyperactivity stop and/or regress. It is understood that said treatment or said prevention preferably concerns herein subjects endowed with an endogenous system cannabinoid, namely man and animals.

The effective amount of compound of formula (I) to administer to a subject affected by hyperactivity of the endocannabinoid system can be easily determined by the person skilled in the art. Typically, a therapeutically effective amount of an active agent ranges from about 10 mg per day to about 1000 mg per day, preferably from 10 mg to 100 mg per day.

As used herein, the expression "hyperactivity of the endocannabinoid system" refers to a dysregulation of the endocannabinoid system which is expressed in the affected subject as an overexpression and/or overactivity of the endocannabinoid CB1 and/or CB2 receptors, and/or by an overexpression and/or overactivity of the enzymes which metabolize endocannabinoids, and/or by an abnormally high level of endocannabinoids (e.g., 2AG and/or anandamide) following a dysregulation of their synthesis pathway. Within the context of the present invention, said hyperactivity is preferably mediated by the CB1 receptors, and involves more particularly the peripheral CB1 receptors (in combination or not with the CB2 receptors). This hyperactivity is thus preferentially present in the tissues in which the peripheral CB1 receptors are expressed. The person skilled in the art is capable of identifying the diseases associated with hyperactivity of the endocannabinoid system, preferably mediated by the CB1 receptors.

Preferably, said diseases are selected from obesity and obesity-related metabolic disorders (Di Marzo et al., 2005; Blüher et al., 2006; Côté et al., 2007; insulin resistance (Song et al., 2011; Eckardt et al., 2009), preferably obesity-related metabolic disorders; diabetes, preferably type II, and associated complications (Matias et al., 2006; Jensen, 2006); alcoholic or non-alcoholic hepatic steatosis, (Osei-Hyiamann et al., 2005; Osei-Hyiaman et al., 2008; Jeong et al., 2008); liver fibrosis (Teixeira-Clerc et al., 2006); cirrhosis; renal fibrosis (Lecru et al., 2015); nephropathy (Jourdan et al., 2012); cardiomyopathies (Montecucco and Di Marzo, 2012; Rajesh et al., 2012; Slavic et al., 2013; Schaich et al., 2014; Pacher and Kunos, 2013); gastroparesis (Izzo and Sharkey, 2010); bone and/or cartilage loss linked for example to osteoporosis or periodontitis (Tam et al., 2008); muscle loss, for example following trauma, or of natural (age-related) or genetic origin such as muscular dystrophies (e.g., Duchenne muscular dystrophy, etc.) (Iannotti et al., 2014); and fertility problems linked for example to low sperm motility and/or viability or to defective oocyte implantation (Amoako et al., 2014).

Further preferably, said diseases are selected from obesity and obesity-related metabolic disorders, and gastroparesis. More preferably, said diseases are selected from obesity-related metabolic disorders, and gastroparesis.

Among obesity-related metabolic disorders, mention may be made of, without limitation, insulin resistance, glucose intolerance, dyslipidaemias such as hypertriglyceridaemia and hypercholesterolaemia, prediabetes and hepatic steatosis.

Among diabetes-related complications, mention may be made of, without limitation, eye diseases such as diabetic retinopathies, ocular oedemas and glaucoma, which can lead to vision loss; kidney diseases such as kidney failure, diabetic nephropathy and diabetic glomerulopathy; angiopathies such as micro- and macro-angiopathies, peripheral coronopathies and artheriopathies; hepatic steatosis; cardiovascular diseases; erectile dysfunction; diabetic gastroparesis; neurological diseases such as diabetic neuropathies, autonomic peripheral neuropathies and cardiac neuropathies.

Preferably, the treatment for obesity and/or for obesity-related metabolic disorders can be combined with an anti-obesity agent, with a hypolipidaemic agent, with a hypocholesterolaemic agent, or with an antidiabetic agent, as described above, and/or with a diet for reducing caloric intake, in particular a balanced normocaloric diet, and thus facilitating weight loss at the same time as improving insulin sensitivity, glucose tolerance and lipaemia mediated by the compound of formula (I) according to the invention.

As used herein, the expression "balanced normocaloric diet" refers to a diet whose composition meets the carbohydrate/lipid/protein proportion recommendations of ANSES (50-55%/35-40%/10-30%, respectively). The person skilled in the art will thus be able to adapt the balanced normocaloric diet to use for the subject to be treated as a function of the subject's sex, weight, height, age, and/or state of health.

Thus, according to a preferred embodiment of the invention, in particular for preventing and/or treating obesity and/or obesity-related metabolic disorders, the subject is put on a balanced normocaloric diet.

Further preferably, said subject is put on said balanced normocaloric diet simultaneously with the administration of the compound of formula (I) or of the pharmaceutical composition according to the invention.

According to another preferred embodiment, the administration of the compound of formula (I) or of the pharmaceutical composition according to the invention is carried out before and/or during the subject's meal(s). This embodiment can be optionally combined with a balanced normocaloric diet as described above. As used herein, the expression "before the meal(s)" means that the administration of the compound of formula (I) or of the pharmaceutical composition according to the invention is carried out at most 30 minutes before the meal, preferably at most 15 minutes before the meal and more preferably right before the meal.

According to the experimental data presented below, the person skilled in the art will easily understand that the compound of formula (I) according to the invention can also be used for uniquely aesthetic purposes, especially to promote weight loss.

Thus, in another aspect, the invention relates to a non-therapeutic use of the compound of formula (I) of the invention to promote and/or accelerate weight loss, or to slow and/or reduce weight gain, in a subject.

In other words, the invention relates to a nontherapeutic method for promoting and/or accelerating weight loss, or for slowing and/or reducing weight gain in a subject, said method comprising a step of administering an effective amount of the compound of the invention to said subject.

The use concerned herein has no therapeutic (secondary) effects, i.e., it is a use not for preventing or treating a disease or one of its symptoms, but only for improving a person's aesthetic appearance. Thus, the subject to whom the present nontherapeutic method is applied is preferably a subject not suffering from hyperactivity of the endocannabinoid system, such as obesity, and/or a subject in good health (i.e., healthy individual). According to a particular embodiment, the subject can be overweight for his or her height but not obese.

Within the context of this use, the effective amount of the compound of formula (I) to administer to the subject can be easily determined by the person skilled in the art. Typically, an effective amount ranges from 10 mg per day to about 1000 mg per day, preferably from 10 mg to 100 mg per day.

According to a preferred embodiment, said subject is put on a balanced normocaloric diet.

Preferably, said subject is put on said balanced normocaloric diet simultaneously with the administration of the compound of formula (I) according to the invention.

According to another preferred embodiment, the administration of the compound of formula (I) is carried out before and/or during the subject's meal(s). This embodiment can be optionally combined with a balanced normocaloric diet as described above.

The compound of the invention can also be used in a composition intended to support slimming.

Thus, according to another aspect, the invention relates to a nontherapeutic composition, for promoting and/or accelerating weight loss, or for slowing and/or reducing weight gain, in a subject, said composition comprising at least one compound according to the invention and at least one acceptable excipient.

More precisely, the invention relates to the nontherapeutic use of said composition, to promote and/or accelerate weight loss, or to slow and/or reduce weight gain, in a subject.

In other words, the invention relates to a nontherapeutic method for promoting and/or accelerating weight loss, or for slowing and/or reducing weight gain in a subject, said method comprising a step of administering an effective amount of said composition to said subject.

Said compound of formula (I) is preferably present in this composition in an amount sufficient to promote and/or accelerate weight loss, or to slow and/or reduce weight gain.

Preferably, said composition comprises from 0.01 wt % to 10 wt %, preferably from 0.02 wt % to 5 wt %, more preferably from 0.05 wt % to 1 wt % of the composition of one or more compounds of formula (I) according to the invention.

Said composition can be in any of the forms acceptable for nontherapeutic use as described herein. For example, said composition can be in a form suitable for oral, sublingual, topical or local administration, etc. The most preferred form of said composition is suitable for oral administration.

The nontherapeutic composition according to the invention can be in the form of a powder, a capsule, a lozenge, a tablet, a pill, a beverage, a solution, a concentrate, a syrup, a suspension, a liquid phial, or a dispersion, and other similar forms. Preferably, the food composition according to the invention is in tablet, powder, capsule, pill, and/or beverage form.

As used herein, "acceptable excipient" refers to a compound capable of enhancing the delivery, the stability or the bioavailability of a composition (herein nontherapeutic), and which can be metabolized and is nontoxic for a subject to whom it is administered.

Preferred excipients according to the invention comprise any one of the excipients commonly used in aesthetic, cosmetic or dietetic products, such as microcrystalline cellulose, lactose, starch, and soya powder.

According to a preferred embodiment, said nontherapeutic composition further comprises at least one agent capable of promoting and/or accelerating weight loss, or of slowing and/or reducing weight gain. Said agent, which can be described herein as slimming agent, can be an anti-obesity agent, a hypolipidaemic agent, a hypocholesterolaemic agent, or an antidiabetic agent, such as those described above.

Another aspect of the invention relates to the nontherapeutic use of the slimming composition of the invention to promote and/or accelerate weight loss, or to slow and/or reduce weight gain, in a subject.

In other words, the invention relates to a nontherapeutic method for promoting and/or accelerating weight loss, or for slowing and/or reducing weight gain in a subject, said method comprising a step of administering an effective amount of said composition to said subject.

According to a preferred embodiment, said subject is put on a balanced normocaloric diet.

Preferably, said subject is put on said balanced normocaloric diet simultaneously with the administration of the nontherapeutic composition according to the invention.

According to another preferred embodiment, the administration of the nontherapeutic composition is carried out before and/or during the subject's meal(s). This embodiment can be optionally combined with a balanced normocaloric diet as described above.

The compound of the invention can also be administered in combination with a slimming agent, and/or with a slimming diet, simultaneously, separately, or sequentially. Said agent can be an anti-obesity agent, a hypolipidaemic agent, a hypocholesterolaemic agent, or an antidiabetic agent, whereas the diet can be a low-calorie and/or low-fat diet.

When the compound according to the invention and the slimming agent are administered separately or sequentially, they can thus be administered in distinct forms.

Thus, another aspect of the invention relates to a compound of formula (I) according to the invention and an agent capable of promoting and/or accelerating weight loss, or of slowing and/or reducing weight gain as described above, as combined preparation for simultaneous, separate, or sequential administration. In other words, the invention relates to a combined use of the compound of formula (I) according to the invention and of an agent capable of promoting and/or accelerating weight loss, or of slowing and/or reducing weight gain as described above for simultaneous, separate, or sequential administration.

Another object of the invention is a nontherapeutic method for promoting and/or accelerating weight loss, or for slowing and/or reducing weight gain in a subject, said method comprising administering an effective amount of the compound of formula (I) of the invention to said subject and putting said subject on a balanced normocaloric diet, simultaneously, separately, or sequentially.

Another object of the invention is a nontherapeutic method for promoting and/or accelerating weight loss, or for slowing and/or reducing weight gain in a subject, said method comprising administering, to said subject, an effective amount of the compound of formula (I) according to the invention and a slimming compound as described above, and putting said subject on a balanced normocaloric diet, simultaneously, separately, or sequentially.

The invention is illustrated by the non-limiting examples hereinafter.

EXAMPLES

Figure 1:
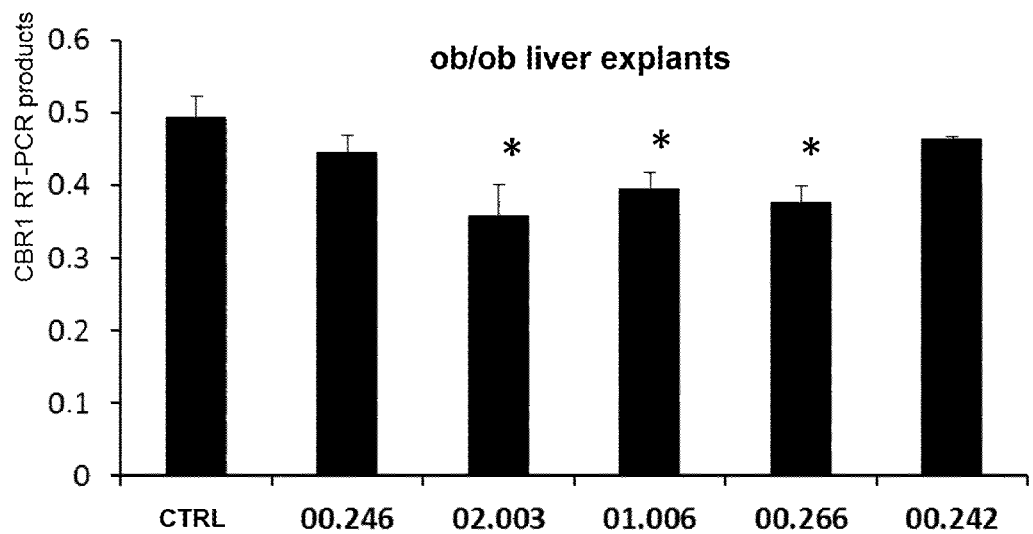
FIG. 1. Expression of CB1 receptors in liver explants of ob/ob mice treated 21 h with molecules JM-00.246, JM-02.003, JM-01.1006, JM-00.266 or JM-00.242.

I. Synthesis of the Compounds According to the Invention
1. Materials

Melting points were determined by means of an Electrothermal IA9300 apparatus, and are reported uncorrected.

1H and 13C NMR spectra were obtained with a Bruker Avance 400 spectrometer (400 MHz). Chemical shifts (δ) are expressed in ppm with tetramethylsilane as internal control. The conventional representations (s=singlet, d=doublet, t=triplet, q=quadruplet, sext=sextuplet, m=multiplet and b=broad) are used for the description of the spectra. Coupling constants are expressed in hertz (Hz).

Mass spectrometry (MS) analysis was carried out on a Waters Acquity UPLC System ZaQ 2000 single quadrupole spectrometer.

Infrared spectra are obtained on a Perkin-Elmer Paragon FTIR 1000 PC apparatus. Only the characteristic absorption bands are shown; wave number values are expressed in cm-1.

Monitoring of the reactions is carried out by thin-layer chromatography (TLC) on silica gel 60F-254 (5735 Merck), and the chromatographic purification columns on silica gel 60 (70-230 Mesh, ASTM, Merck).

All the reagents and solvents used are commercial products.

2. Synthesis of 4-methylthiobenzyl-4-methylthiobenzaldimine (IV)

In 50 mL of toluene, dissolve 5.57 g (36.6 mM) of 4-methylthiobenzaldehyde and 5.0 g (35.92 mM) of 4-methylthioaniline. Add 3 g anhydrous sodium sulphate, and heat to reflux of the solvent, under stirring, for 4 hours. At the end of that time, the solvent is removed with the rotary evaporator under reduced pressure. The collected solid is triturated in 10 mL of isopropyl oxide and the suspension obtained filtered on sintered glass. Thus collect 7.66 g of imine (yield=78%).

Chemical Features:

MP° C.=143-144 (Diisopropyl oxide).

$^1$H-NMR (CDCl$_3$): δ 2.51, s, 3H, 4-SC$\underline{H}$3; 2.54, s, 3H, 4'-SC$\underline{H}$3; 7.18, d, 2H, H$^3$H$^5$, J=6.7 Hz; 7.29, d, 2H, H$^2$H$^6$; 7.30, d, 2H, H$^{3'}$H$^{5'}$, J=8.4 Hz; 7.80, d, 2H, H$^2$H$^6$; 8.41, s, 1H, $\underline{H}$C=N.

MS (ESI) m/z (%): 274[M+H]$^+$

IR (KBr, cm$^{-1}$): 1552.53 (ν C=N).

3. Synthesis of the Acid Chloride of Phthaloylglycine

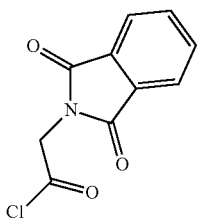 [SMILES: O=C(Cl)CN1C(=O)c2ccccc2C1=O]

Dissolve 2 g (9.75 mM) of N-phthaloylglycine in 20 mL of thionyl chloride, and reflux for 3 hours. At the end of that time, the thionyl chloride is evaporated under reduced pressure with the rotary evaporator. The product obtained is taken up three times in 50 mL of toluene, and subjected each time to evaporation under reduced pressure. At the end of the third evaporation, the product obtained is kept under vacuum for 30 minutes, then is taken up again in 20 mL of dry dichloroethane and stored as such until use.

4. Synthesis of trans-1,4-di-(4-methylthiophenyl)-3-N-phthaloyl-azetidine-2-one (Compound IA=Also Called Hereinafter JM-00.266 or M6)

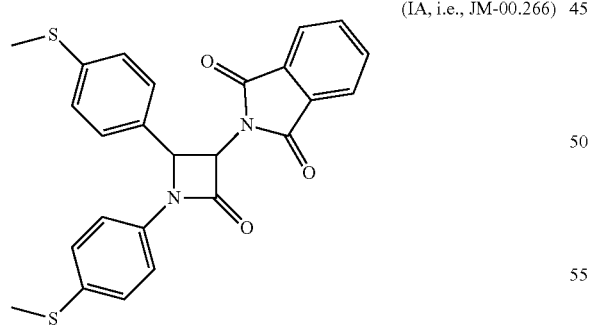

(IA, i.e., JM-00.266)

In a 250-mL round-bottom flask, dissolve 2.73 g (10.0 mM) of imine (IV) in 50 mL of dry dichloromethane. Add 5 mL of triethylamine and place the whole under stirring. Next, slowly introduce a solution of acid chloride of phthaloylglycine (9.75 mM) while keeping the mixture at a temperature below 10° C. Once the addition is finished, allow the mixture to return to room temperature, and keep it as such while monitoring the reaction's progress by TLC. At the end of 3 hours, the reaction progresses no further; pour the reaction mixture into 100 mL of water, and collect the organic phase with a separating funnel. Wash it again with an identical amount of water, then dry it over anhydrous sodium sulphate, filter and evaporate the solvent to dryness. The residue obtained is then chromatographed on silica column by eluting with dichloromethane, which makes it possible to obtain 2.39 g of compound (IA) (Y=53%).

Chemical Features:

MP° C.=118-120 (Diethyl ether)

$^1$H-NMR (CDCl$_3$): δ 2.44, s, 3H, C$\underline{H}$3; 2.49, s, 3H, C$\underline{H}$3; 5.26, d, 1H, H$_a$; 5.33, d, 1H, H$_b$ (JH$_a$H$_b$=2.4 Hz); 7.18, d, 2 arom.H, (J=8.4 Hz); 7.25-7.30, m, 4 arom.H; 7.78, m, 2H, H4"-H5"; 7.88, m, 2H, H3"-H6".

$^{13}$C-NMR (100.6 MHz, CDCl) 16.45(CH$_3$); 16.50(CH$_3$); 60.99(Cb); 62.77(Ca); 118.15(2C); 123.85(C3"-C6"); 126.63(2C); 127.00(2C); 127.91(2C); 131.65(C2"-C7"); 132.10(C1); 134.14(C4-C1'); 134.61(C4"-C5"); 140.11 (C4'); 161.75(C1"-C8"); 166.65(Cc).

MS (ESI) m/z (%): 461.6 [M+H]$^+$

IR (KBr, cm$^{-1}$): 3064, ν CH$_{ar}$; 2974, 2922, 2835, ν CH$_{aliph}$; 1759, 1714, ν C=O.

5. Other Compounds Tested

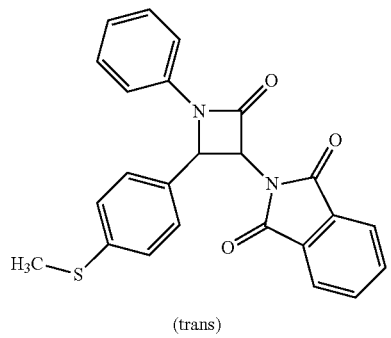

JM-00.242

(trans)

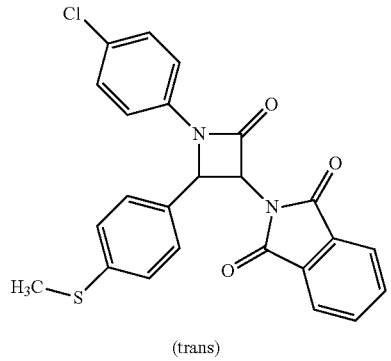

JM-00.246

(trans)

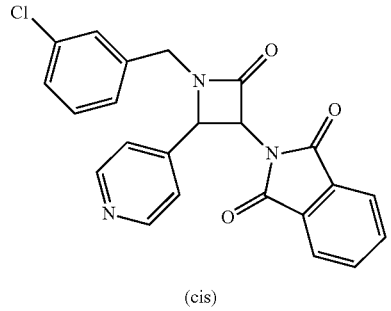

JM-01.006

(cis)

-continued

JM-02.003

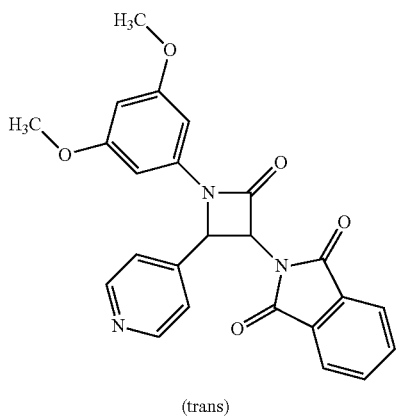

(trans)

SR141716

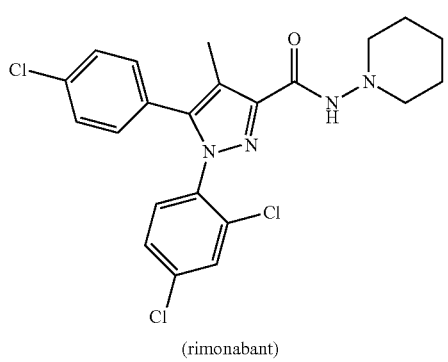

(rimonabant)

6. Alternative Synthetic Pathway for trans-1,4-di-(4-methylthiophenyl)-3-N-phthaloyl-azetidine-2-one (Compound IA=Also Called Hereinafter JM-00.266 or M6)

Another synthetic pathway for compound JM-00.266 was developed. It consists in contacting the imine (compound IV) with N-phthaloylglycine, and generating the ketene in situ by means of a coupling agent, phenyl dichlorophosphate, in the presence of triethylamine as proton acceptor. The advantage of this method is to avoid the use of thionyl chloride, the handling and removal of which can be tricky.

According to one procedure, 1.38 g of imine (compound IV) (5 mM) is dissolved in 20 mL of dichloromethane, under stirring; 3 mL of triethylamine then 1.128 g of N-phthaloylglycine are added. 1.5 mL (2.11 g, i.e. 10 mM) of phenyl dichlorophosphate is then introduced dropwise into the mixture, and the reaction is left at room temperature for 3 h. At the end of that time, the reaction mixture is washed with water, the organic phase is collected, dried and concentrated under reduced pressure. The residue obtained is chromatographed on silica gel column by eluting with dichloromethane. 1.51 g of compound IA (JM-00.266 trans; the cis isomer is not present in the reaction mixture) is thus collected with a 66% yield.

7. Deprotection of the Amine Function Starting with trans-1,4-di-(4-methylthiophenyl)-3-N-phthaloyl-azetidine-2-one (Compound IA=Also Called Hereinafter JM-00.266 or M6)

In addition, deprotection of the phthaloylated amine function on compound JM-00.266 was carried out. Release of the amine function was concluded successfully by action of methylhydrazine in methylene chloride.

According to one procedure, 0.1 mL (2.18 mM) of methylhydrazine is added to 0.44 g of compound IA JM-00.266 (0.955 mM) in solution in 20 mL of dichloromethane (DCM); the mixture is left under stirring first at room temperature then while slowly raising the temperature to reflux of DCM and while monitoring the reaction's progress by TLC. When the reaction is completed (4 h), the reaction mixture is washed with water then dried and concentrated by evaporation to dryness. The residue obtained is chromatographed on silica gel by means of a short column (diameter=30 mm; length=70 mm) and by eluting with ethyl acetate. 221 mg of the desired amine is thus collected (compound IF, also called hereinafter HR-0131 trans) with a yield ranging from 70 to 81% with an optimized synthesis and purification process.

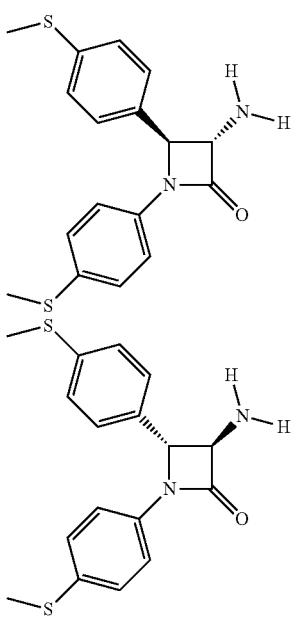

Structures of the Two Enantiomers of Compound HR-0131 Trans

Physicochemical Features of Compound HR-0131:

Empirical formula: $C_{17}H_{18}N_2S_2O$; molecular mass: 330.47; M=134° C. (AcOEt).

IR (KBr, cm$^{-1}$): 3350-3061 (vCH$_{ar}$); 2981-2835 (vCH$_{aliph}$); 1728 (vC=O).

$^1$H-NMR, δ(ppm), DMSO-d6: 2.43, s, 3H, SCH$_3$(benzald); 2.49, s, 3H, SCH$_3$(anil); 3.66, 2H, NH$_2$; 3.92, d, 1H, (NCHlact); 4.73, d, 1H, (COCHlact), J=2.0 Hz; 7.18-7.34, m, 8 Har.

$^{13}$C-NMR, δ(ppm), DMSO-d6: 14.73; 15.54; 65.41; 70.82; 117.75; 124.31; 126.41; 126.91; 127.52; 128.91; 132.41; 132.51; 133.08; 134.30; 135.01; 138.14; 168.80.

MS (ESI) m/z (%): 331 [M+H]$^+$

8. Synthesis of Derivatives Starting with Amine HR-0131

Starting with the amine prepared previously, it was envisaged to synthesize a superior homologous derivative (HR-0133) of compound JM-00266. This derivative results from the condensation of phthaloylglycine on HR-0131 and represents a structure into which a space has been introduced between the lactam ring and the phthaloyl substituent.

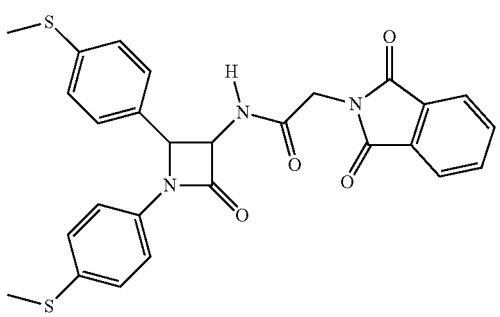 [SMILES: CSc1ccc(C2C(NC(=O)CN3C(=O)c4ccccc4C3=O)C(=O)N2c2ccc(SC)cc2)cc1]

Structure of Compound HR-0133 Trans

According to one procedure, 144 mg (0.7 mM) of N-phthaloylglycine and 1 mL of triethylamine are added to a solution of 183 mg (0.55 mM) of HR-0131 in 15 mL of dichloromethane. 169 mg (0.8 mM) of phenyl dichlorophosphate is then added dropwise and the mixture is left under stirring for 3 h. At the end of that time, the solvent is evaporated and the residue obtained is chromatographed on silica column by eluting with ethyl ether. 61 mg of the desired product (HR-0133 trans) is obtained (Y=21%, a yield which can be improved by optimizing the synthesis and purification process).

Physicochemical Features of Compound HR-0133:

Empirical formula: $C_{27}H_{23}N_3S_2O_4$; molecular mass: 517.63; M=190-192° C. (iPrOiPr).

IR (KBr, cm$^1$): 3348 (vCH$_{ar}$); 2998-2918 (vCH$_{aliph}$); 1728, 1693 (vC=O).

$^1$H-NMR, δ(ppm), DMSO-d6: 2.43, s, 3H, SC$\underline{H}_3$(benzald); 2.49, s, 3H,S C$\underline{H}_3$(anil); 4.37, s, 2H, C$\underline{H}_2$; 4.72, dd, 1H, (COC$\underline{H}$lact), J=2.4 Hz, J=7.6 Hz; 5.05, d, 1H, (NC$\underline{H}$lact), J=2.4 Hz; 7.18, d, 2H, H$_2$H$_6$benzald, J=8.8 Hz; 7.23, d, 2H, H$_3$H$_5$benzald, J=8.8 Hz; 7.29, d, 2H, H$_3$H$_5$anil, J=8.4 Hz; 7.40, d, 2H, H$_2$H$_6$anil, J=8.4 Hz; 7.90-7.98, m, 4H, Ft$_{ar}$H, 9.20, d, 1H, N$\underline{H}$, J=7.6 Hz.

$^{13}$C-NMR, δ(ppm), DMSO-d6: 14.62; 15.39; 40.33; 61.49; 65.08; 117.86(2C); 123.44(2C); 126.34(2C); 127.35 (2C); 127.39; 131.88; 133.09(2C); 133.19(2C); 134.40; 134.80(2C); 141.00; 163.98; 166.98; 167.59(2C).

MS (ESI) m/z (%): 518 [M+H]$^+$.

II. Biological Activity of the Synthesized Compounds
1. Materials and Methods
1.1. In Vitro Studies
1.1.1. Liver Explant Culture The liver of the mice was perfused in situ, under sodium pentobarbital anaesthesia (50 mg/kg), with Hank's medium (pH 7.4) saturated with oxygen. Next, the liver was sectioned using a Brendel/Vitron slicer (Tucson, Ariz., USA) in the same medium. The liver sections (about 200 µm) were then incubated 21 h in William's medium E (WME) oxygenated and supplemented with deactivated foetal calf serum (10%) and antibiotic/antifungal cocktail (1%) under controlled atmosphere (5% CO2), to which is added either the antagonist to be tested or vehicle.

1.1.2. Gene Expression

Total messenger RNA (mRNA) extraction was carried out with Tri Reagent (Euromedex, France) and consecutive synthesis of complementary DNA (cDNA) was carried out from 1 µg of mRNA with the Bio-Rad iScripttm Reverse Transcription super mix kit (Bio-Rad, France).

Gene expression was evaluated by semi-quantitative real-time reverse transcription-polymerase chain reaction (RT-PCR). The primers used were designed using the Primer3Plus software (http://www.bioinformatics.nl/cgi-bin/primer3plus/primer3plus.cgi) and were synthesized by MWG-Biotech (TATA box-binding protein: Sense acggcacaggacttactcca, antisense gctgtctttgttgctcttccaa; CB1R: Sense ccgcaaagatagtcccaatg, antisense aaccccacccagtttgaac). Semi-quantification of gene expression was obtained by taking into account the efficacy of each PCR and after standardization with the reporter gene, TATA box-binding protein.

1.1.3. GloSensor cAMP Assay

HEK293T/17 (ATCC) cells were cultured in DMEM 10% FCS, then seeded at 30000 cells/well in 96-well plates. After 24 h, the cells were subjected to transient transfection by FuGENE HD (Promega) by pcDNA3.1-mCB1 (50 ng) and pGlo (100 ng) plasmids with or without pertussis toxin (PTX). For the control assays, the cells were transfected with empty pcDNA3 (EV) and pGlo vectors with or without PTX. At 48 h (24 h post-transfection), the cells were loaded for 2 h with 2% GloReagent in CO2-independent medium with 10% FCS (80 µL/well).

The cells were then treated by adding, at t=0, 10 µL/well of Forskolin (FSK) 1 µM final, in order to increase the basal cAMP concentration. The kinetics of appearance of cAMP was monitored for 10 minutes. At t=10, the molecules to be tested were added and the cAMP variations measured for 20 minutes. The light signal was measured in RLU and is expressed as % response relative to the signal read at t=10 min (FSK1 µM). Sigmoidal curves were obtained by measurement at t=10 min after addition of the molecule to be tested (thus t=20 min total) of the percentage of light signal as a function of molecule concentration. The 4PL regression was carried out using the Sigma Plot software and made it possible to obtain an EC50 (1 experiment, n=3).

1.2. Short-term In Vivo Studies: Acute Tests.
1.2.1. Gastrointestinal Transit

Transit through the stomach and the intestine was measured via oral administration of vegetable charcoal suspended in gum arabic used herein as nonabsorbable marker. Briefly, following a short fast, C57BL/6 mice were injected intraperitoneally (i.p.) with anandamide (10 mg/kg) in the presence or absence of the molecule of interest JM-00.266 (i.e., compound IA) (10 mg/kg) before oral charcoal administration. 25 minutes later, the animals were sacrificed by cervical dislocation in order to entirely remove the intestine. The distance between the beginning of the pylorus and the location of the charcoal bolus was measured.

1.2.2. Oral Glucose Tolerance Test (OGTT)

In order to evaluate the short-term effects of the rimonabant-like molecules, as well as their selectivity for CB1R, wild-type C57BL/6 mice and CB1R −/− mice underwent an oral glucose tolerance test (OGTT at 2 g/kg) 10 min after i.p. injection of vehicle or of JM-02.003 or JM-00.266 (i.e., compound IA) (10 mg/kg). Blood glucose was measured at times t=0, t=15 min, t=30 min, t=45 min, t=60 min, t=90 min, and t=120 min post-oral. glucose administration using a Contour®TS blood glucose monitor (ref. 81574201, Bayer HealthCare) and reactive strips (ref. 81574274, Bayer HealthCare).

1.2.3. Insulin Tolerance Test (ITT)

The short-term effect of molecule JM-00.266 (i.e., compound IA) on insulin sensitivity was measured during an insulin tolerance test. To that end, wild-type C57BL/6 mice were injected intraperitoneally with fast-acting insulin (0.5 IU/kg; ref. YT60088, Actrapid®) 10 min after i.p. injection of vehicle or of JM-00.266 (i.e., compound IA) (10 mg/kg). Blood glucose was measured at times t=0, t=15 min, t=30 min, t=45 min, t=60 min, t=90 min, and t=120 min post-i.p. insulin injection using a blood glucose monitor.

1.2.4. Plasma Insulin

Assay of plasma insulin was carried out using the ALPCO™ Mouse Insulin ELISA Kit (ref. AKRIN-011T, ALPCO Diagnostics) according to the supplier's instructions. Blood samples were collected during an OGTT at t=0, t=30, t=60, t=120 min post-administration of the oral bolus of glucose (2 g/kg).

1.3. Long-term In Vivo Studies: Chronic Administration 1.3.1. Diet, Food Intake and Body Composition of the Animals In order to determine the long-term effects of the molecules of interest, C57BL/6 mice made obese by means of a high-sucrose, high-fat diet (HSHF: 30% crude fat, 33.5% carbohydrates; ref. E15126-34; ref. E15126-34, SSNIFF, Soest, Germany) for 20 weeks. These mice then received daily an i.p. injection of rimonabant, JM-00.266 (i.e., compound IA) or vehicle for a period of 30 days. In parallel, weight and food intake were monitored every two days following the beginning of the treatment.

The long-term effect of the treatment on body composition was measured using an EchoMRI™ scanner allowing non-invasive analysis of fat mass, lean mass and body fluid composition by nuclear magnetic resonance (NMR) on the live animal without anaesthesia.

1.3.2. Behavioural Study: Open-field Test

Locomotor activity of the mice was measured at the conclusion of the chronic treatment with rimonabant or molecule JM-00.266 (i.e., compound IA) by an infrared monitoring system. To that end, the animals were placed individually in 43×43 cm plexiglass boxes (MED associates) for 20 min. Two series of 16 pulsed infrared beams were spaced 2.5 cm apart on opposite walls to record ambulatory X-Y movements at 100 ms resolution. The centre was defined as a central 32×32 cm square. In addition to locomotor activity information, this test makes it possible to predict anxiolytic activity in response to novelty or to an anxiogenic environment. The variables measured in the open field are total ambulatory activity (in cm), the number of entries and the time spent in the central area as well as the distance traversed in the centre divided by the total distance traversed.

1.3.3. Plasma Assays

Total cholesterol, triglycerides and hepatic markers were assayed by a Dimension Vista Intelligent Lab System (Siemens, Saint-Denis, France) using suitable reagents.

1.3.4. Oral Glucose Tolerance Test and Insulin Tolerance Test

In order to evaluate the long-term effects of the treatment on blood glucose control, glucose tolerance (OGTT) and insulin sensitivity (ITT) were evaluated pre- and post-treatment. Thus, for the OGTT the mice were force-fed glucose (2 g/kg), and for the ITT the mice received an i.p. injection of insulin (0.5 IU/kg). In both cases, blood glucose was measured at times t=0, t=15 min, t=30 min, t=45 min, t=60 min, t=90 min, and t=120 min post-glucose ingestion using a Contour®TS blood glucose monitor (ref. 81574201, Bayer HealthCare) and reactive strips (ref. 81574274, Bayer HealthCare).

1.4 Long-term In Vivo Study: Administration of Compound IA in Combination with a Reduced Energy Supply in Obese Mice 1.4.1 High-fat Diet, Food Intake Associated with a Low-fat Diet and Body Mass of the Animals In order to determine the long-term effects of compound of interest JM-00.266 (i.e., compound IA), C57BL/6 mice were made obese by means of a high-fat diet (30% crude fat, 33.5% carbohydrates; ref. E15126-34, SSNIFF, Soest, Germany) for 15 weeks. The mice were then subjected to a low-fat diet (5% lipids; Standard Diet AO4; UAR, Epinay-sur-Orge, France) and received daily, in the middle of the day, an oral dose of JM-00.266 (i.e., compound IA) or of vehicle over a period of 43 days. The weight of the animals was measured every two days from the beginning of the treatment.

1.4.2 Glucose Tolerance Test

In order to evaluate the long-term effects of the treatment on blood glucose control, glucose tolerance was evaluated at the end of the treatment period. The mice received an intraperitoneal injection of glucose (2 g/kg) then blood glucose was measured at times t=0, t=15 min, t=30 min, t=45 min, t=60 min, t=90 min, and t=120 min post-glucose injection using a My Life Pura blood glucose monitor (Ypsomed, Paris, France).

1.5 Long-term In Vivo Study: Administration of Compound IA Simultaneously with Food Intake in Obese Mice Maintained on a High-fat Diet The choice of this approach is justified by the fact that previous results show that when the administration of M6 precedes a glucose load, sugar tolerance is very clearly improved.

1.5.1 High-fat Diet, Administration of the Compound Simultaneously with Food Intake and Body Mass of the Animals C57BL/6 mice were made obese by means of a high-fat diet (35% crude fat, 25.3% carbohydrates; ref. E15742-34, SSNIFF, Soest, Germany) for 15 weeks. The mice maintained on the same diet then received daily an oral dose of JM-00.266 (i.e., compound IA) or of vehicle incorporated in the feed over a period of 43 days. The weight of the animals was measured every two days from the beginning of the treatment.

1.5.2 Glucose Tolerance Test

In order to evaluate the long-term effects of the treatment on blood glucose control, glucose tolerance was evaluated at the end of the treatment period. The mice received an intraperitoneal injection of glucose (2 g/kg) then blood glucose was measured at times t=0, t=15 min, t=30 min, t=45 min, t=60 min, t=90 min, and t=120 min post-glucose injection using a My Life Pura blood glucose monitor (Ypsomed, Paris, France).

1.5.3 Gene Expression

Total messenger RNA (mRNA) extraction was carried out with Tri-Reagent (Euromedex, France) and consecutive synthesis of complementary DNA (cDNA) was carried out from 1 µg of mRNA with the Bio-Rad iScripttm Reverse Transcription super mix kit (Bio-Rad, France). Gene expression was evaluated by semi-quantitative real-time reverse transcription-polymerase chain reaction (RT-PCR). The primers used, described below, were selected using the Primer3Plus software (http://www.bioinformatics.nl/cgi-25 bin/primer3plus/primer3plus.cgi) and synthesized by MWG-Biotech. Semi-quantification of gene expression was obtained by taking into account the efficacy of each PCR and standardization with the reporter gene TATA box-binding protein (TBP).

Primers Used:

| Gene | SEQ ID NO | 5'-sense primer-3' | SEQ ID NO | 5'-antisense primer-3' |
|---|---|---|---|---|
| TPB | 1 | acggcacaggacttactcca | 2 | gctgtctttgttgctcttccaa |
| CB1R | 3 | ccgcaaagatagtcccaatg | 4 | aaccccacccagtttgaac |
| CB2R | 5 | caaaggaggaagtgcttggt | 6 | tggagagatcggcttatgttg |
| F4/80 | 7 | tgacaaccagacggcttgtg | 8 | gcaggcgaggaaaagatagtgt |
| FAAH | 9 | ggaccttgctcccctttct | 10 | cctgctgggctgtcacata |
| FAS | 11 | ggctgcagtgaatgaatttg | 12 | ttcgtacctccttggcaaac |
| G6P | 13 | tggcctggcttattgtacct | 14 | gtgctaagaggaagacccga |
| GLUT2 | 15 | ctcttcaccaactggccct | 16 | cagcagataggccaagtagga |
| GLUT4 | 17 | gatgccgtcgggtttccagca | 18 | tgttccagtcactcgctgccg |
| DGAT2 | 19 | agccctccaagacatcttctct | 20 | tgcagctgtttttccacct |
| NAPE-PLD | 21 | ctcgatatctgcgtggaaca | 22 | ctgaattctggcgctttctc |
| SCD1 | 23 | ccggagacccttagatcga | 24 | tagcctgtaaaagatttctgcaaacc |
| TNF-a | 25 | cggggtgatcggtccccaaag | 26 | tggtttgctacgacgtgggct |

The impact of the treatment on endocannabinoid system activity is evaluated by measuring the gene expression 1) of receptors CB1R and CB2R 2) of the endocannabinoid synthesis enzyme, N-acyl phosphatidylethanolamine phospholipase D (NAPE-PLD) and 3) of the endocannabinoid degradation enzyme, fatty acid amide hydrolase (FAAH).

Fatty acid synthase (FAS), stearoyl-CoA desaturase 1 (SCD-1) and glycerol-phosphate acyl-transferase (GPAT2) are enzymes whose expression variations reflect lipogenic activity.

Glucose-6-phosphatase (G6P) and the glucose transporters GLUT2 and GLUT4 in the liver are used herein as neoglucogenesis markers.

F4/80 is a mature macrophage marker.

Tumour necrosis factor-alpha (TNF-a) is a proinflammatory cytokine affecting the regulation of numerous biological processes such as immune functions, cell differentiation and energy metabolism.

2. Results 2.1. Short-term In Vitro and In Vivo Experiments (Acute Injections) on Compounds JM-00.246, JM-02.003, JM-01.1006, JM-00.242 and JM-00.266 (i.e., Compound IA).

2.1.1. Effects of Candidate Molecules JM-00.246, JM-02.003, JM-01.006, JM-00.266 (i.e., Compound IA) and JM-00.242 on Hepatic Expression of CB1R in Ob/Ob Mice Studies previously carried out in the laboratory indicated that it was possible to modulate CB1R expression in liver explants cultured in the presence of agonists or of antagonists (Jourdan et al. 2012). For example, CB1R expression in liver explants is reduced following treatment with SR141716 (i.e., rimonabant). Consequently, this in vitro model was used herein to preselect candidate molecules on the basis of their capacity to modify CB1R expression.

Based on these previous results obtained with SR141716 (i.e., rimonabant), the capacity of each compound to decrease CB1R expression was tested in the same liver explant model.

Only molecules JM-02.003, JM-01.006 and JM-00.266 (i.e., compound IA) caused a significant decrease in hepatic CB1R expression, i.e., an effect comparable to that observed in the previous study with SR141716 (i.e., rimonabant) (FIG. 1). Molecules JM-00.246 and JM-00.242 were not selected for the remainder of the study.

2.1.2. Effects of Preselected Molecules JM-02.003, JM-01.1006 and JM-00.266 on CB1 Receptor Activity The capacities of JM-02.003, JM-01.006 and JM-00.266 (i.e., compound IA) to antagonize CB1R were tested in a CB1R-transfected cell model by measuring cAMP variations (GloSensor cAMP assay).

Figure 2A:
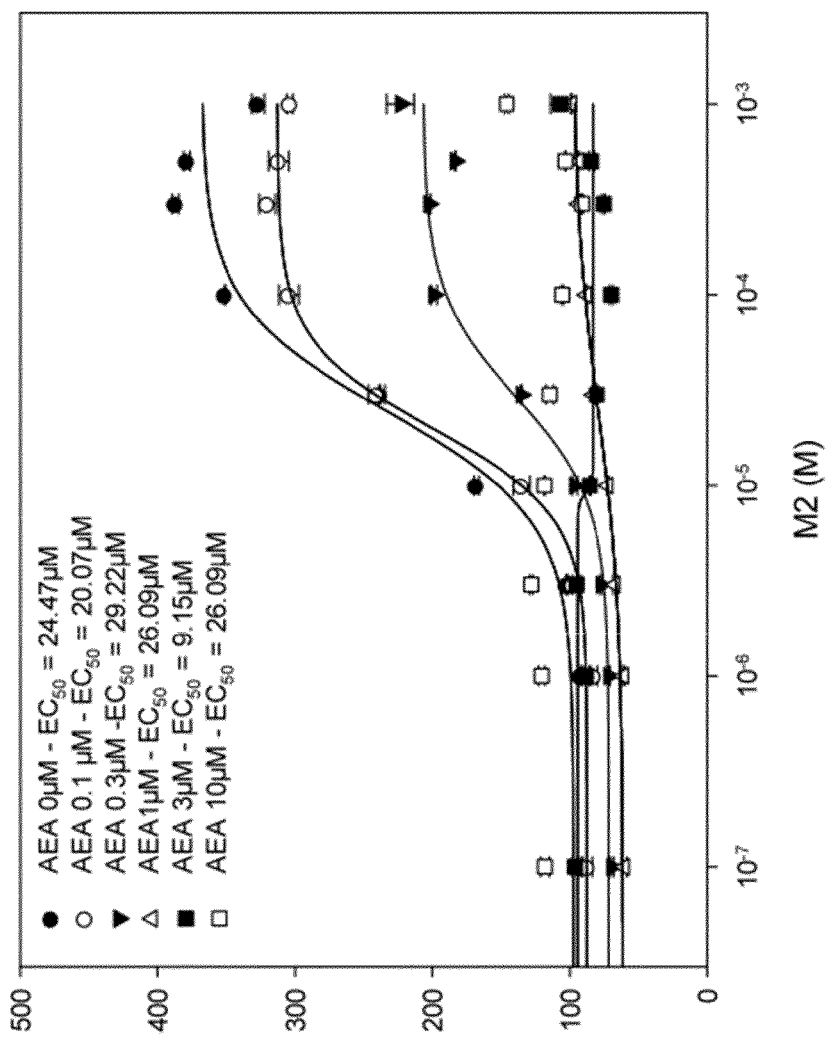
FIG. 2. cAMP variations in HEK293T/17 cells transfected by the plasmids pcDNA3.1-mCB1 (50 ng) and pGlo (100 ng) and subjected to increasing concentrations of JM-02.003 (2A), JM-01.1006 (2B) and JM-00.266 (2C) in the presence or absence of AEA.
Figure 2B:
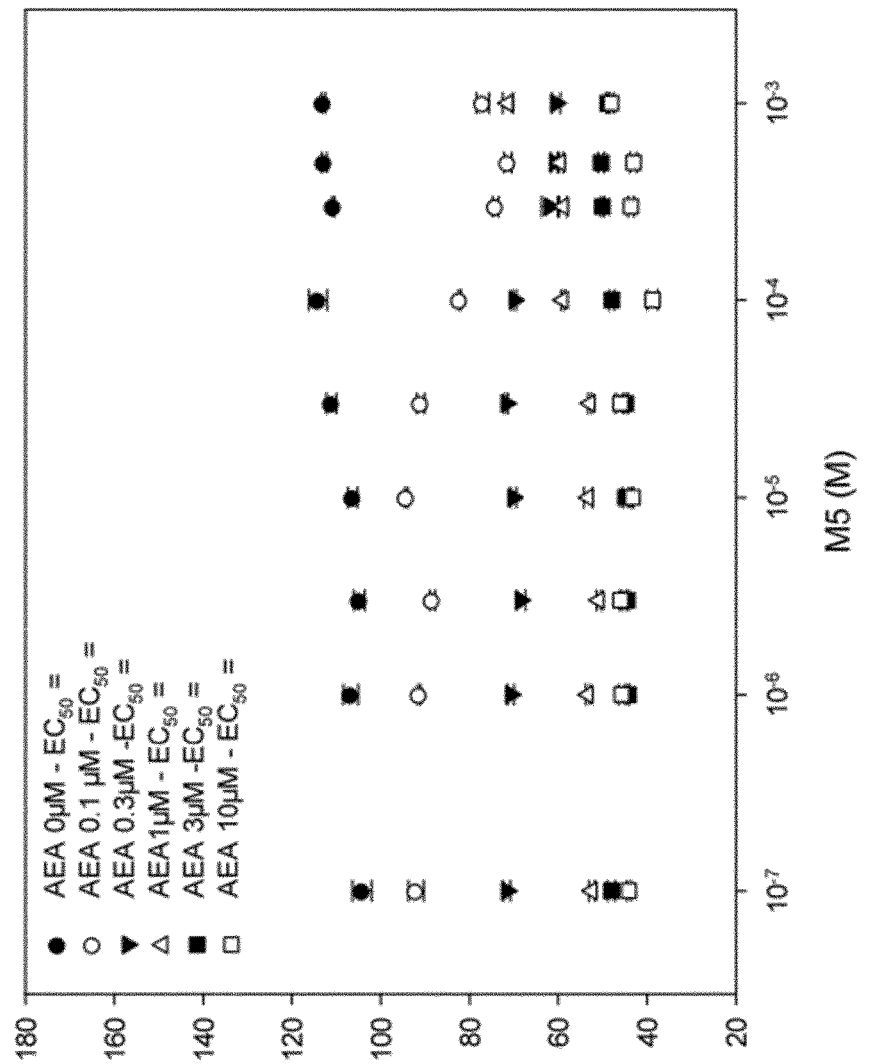
Figure 2C:
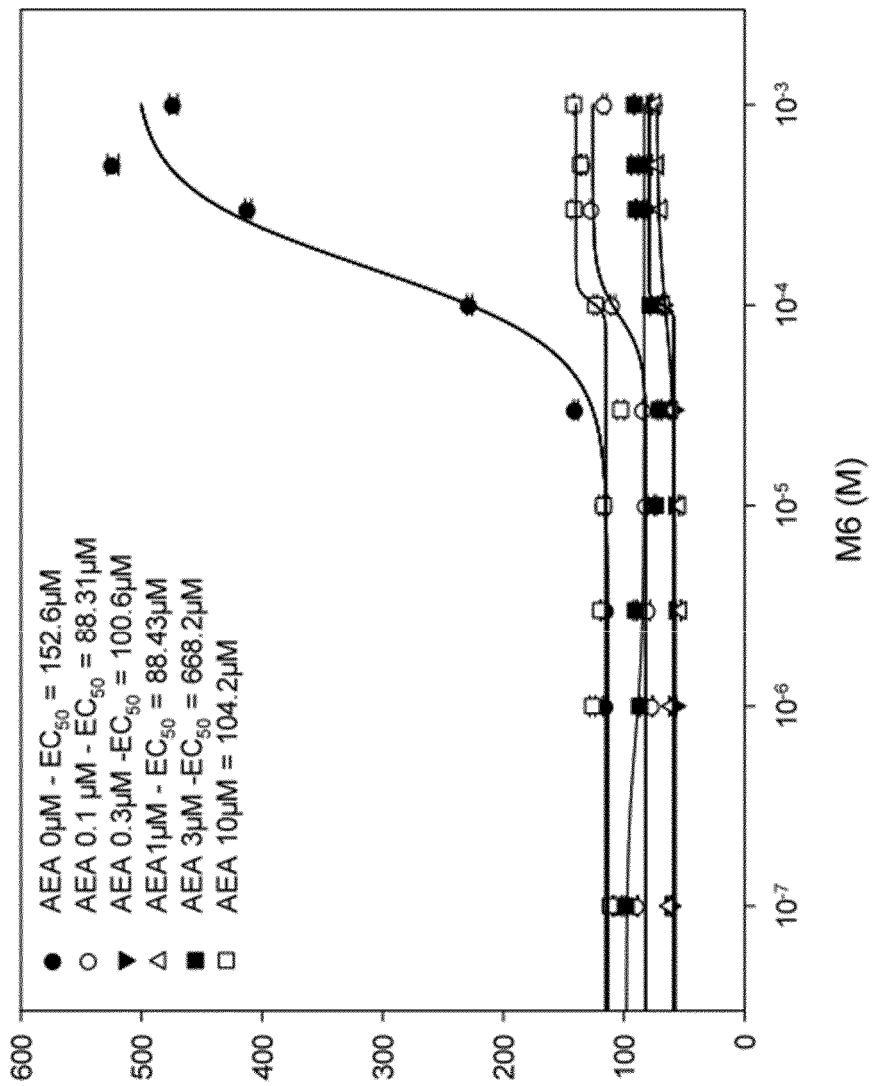

First, it was verified by using this in vitro model that activation of the receptors by an agonist, in this case AEA, lead indeed to a reduction in the intracellular cAMP concentration (data not shown). The results indicate that cAMP concentrations are increased in the absence of agonist (AEA) in cells treated with JM-02.003 and JM-00.266 (i.e., compound IA) whereas JM-01.006 has no effect (FIG. 2). These data confirm that only molecules JM-02.003 and JM-00.266 (i.e., compound IA) are CB1R ligands and exert an inverse agonist effect on the receptor. Molecule JM-01.1006 was thus not selected for the remainder of the study.

2.1.3. Effects of Acute Treatment with Molecules JM-02.003 and JM-00.266 (i.e., Compound IA) on Glucose Tolerance in Wild-type C57Bl/6J Mice.

In order to evaluate the in vivo effects of the selected molecules, the Inventors sought to determine if a single i.p. injection could modulate carbohydrate metabolism in mice. Indeed, recent work showed that CB1R activation in response to a single i.p. injection of AEA (CB1R agonist) alters glucose tolerance and insulin resistance (Liu et al., 2012).

To that end, wild-type C57Bl/6J mice received a 10 mg/kg i.p. injection of antagonist JM-02.003 or JM-00.266 (i.e., compound IA) 10 min before a 2 g/kg oral glucose load. These results show that i.p. injection of these two molecules improves glucose tolerance compared with mice having received vehicle (FIGS. 3A and B).

Figure 3:
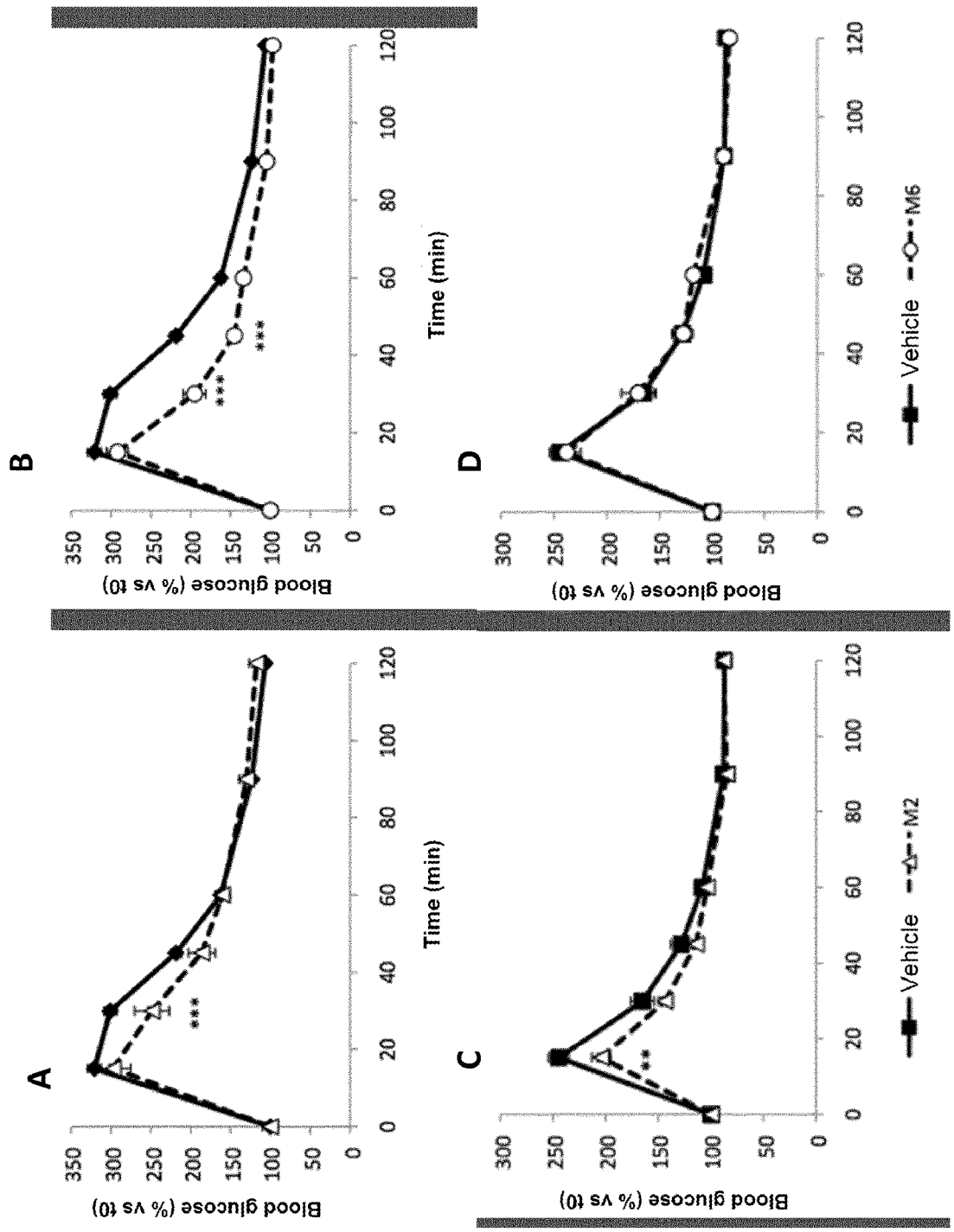
FIG. 3. Effect of a 10 mg/kg i.p. injection of JM-02.003 (M2) or JM-00.266 (M6) on glucose tolerance in wild-type (3A and 3B, respectively) or CB1R KO mice (3C and 3D, respectively).

When these experiments are repeated in CB1R KO mice, it is observed that the improvement in glucose tolerance is abolished in mice treated with JM-00.266 (i.e., compound IA) whereas it persists with JM-02.003 (FIGS. 3C and D). This confirms that only molecule JM-00.266 (i.e., compound IA) exerts a specific CB1R inverse agonist effect. Molecule JM-02.003 was thus not selected for the remainder of the study.

2.1.4. Effects of Acute Treatment with JM-00.266 (i.e., Compound IA) on Insulin Sensitivity and Production in Wild-type C57Bl/6J Mice.

In order to know if the improvement in blood glucose control observed in response to i.p. injection of JM-00.266 (i.e., compound IA) is potentially due to an increase in insulin secretion and/or to a better insulin sensitivity, a plasma insulin assay was carried out following oral administration of the glucose bolus as well as an insulin tolerance test (ITT).

Figure 4A:
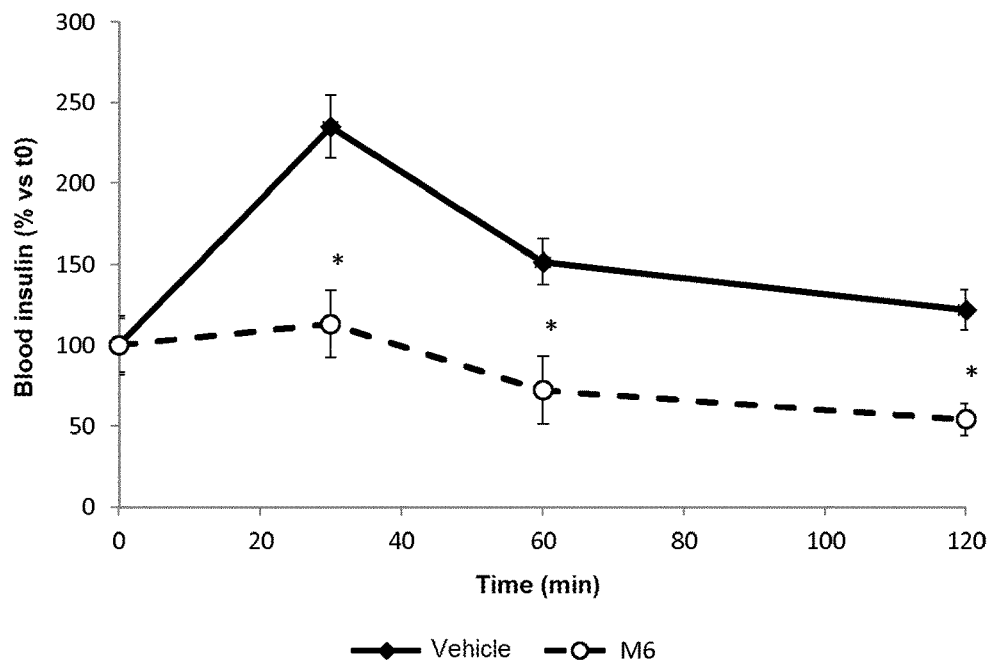
FIG. 4. Effect of a 10 mg/kg i.p. injection of vehicle or of JM-00.266 (M6) on plasma insulin concentration during an OGTT (4A) and on insulin tolerance (ITT; 4B) in wild-type mice.
Figure 4B:
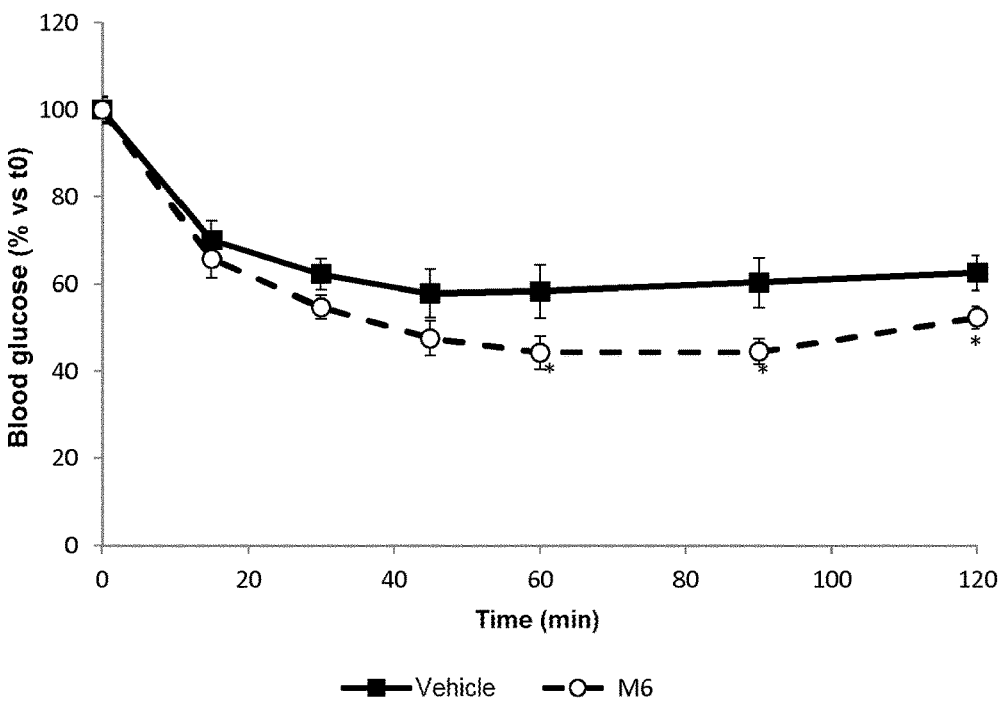

The results show that insulin production induced by glucose administration is not stimulated by JM-00.266 (FIG. 4A). On the contrary, blood insulin at t=30 min is lower in mice treated with JM-00.266 (i.e., compound IA) suggesting an improvement in the capacities to utilize glucose. The ITT also reveals that insulin exerts a more powerful effect on plasma glucose clearance in animals first treated with JM-00.266 (i.e., compound IA) compared with the control animals (FIG. 4B).

These data suggest that molecule JM-00.266 (i.e., compound IA) improves glucose tolerance by increasing insulin sensitivity.

2.1.5. Effects of Acute Treatment with JM-00.266 (i.e., Compound IA) on Gastrointestinal Transit in Wild-type C57Bl/6J Mice.

Figure 5:
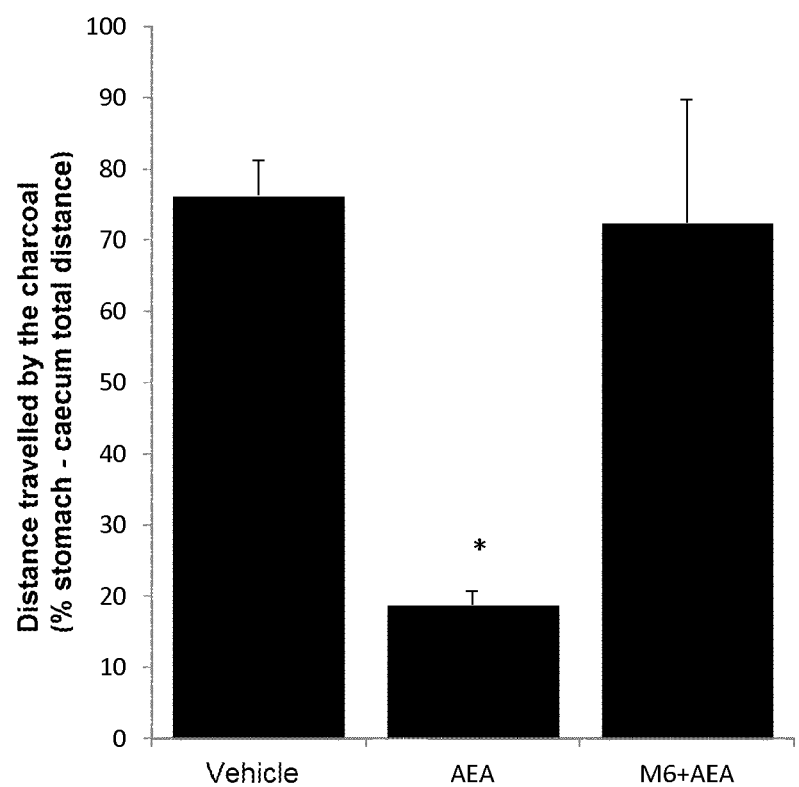
FIG. 5. Effect of a 10 mg/kg i.p. injection of vehicle, of anandamide (AEA) or of AEA+JM-00.266 (M6) on gastro-intestinal transit in wild-type mice.

It is clearly shown in the literature that CB1R activation strongly inhibits gastrointestinal motility (Di Marzo et al., 2008). On this basis, the Inventors sought to know if molecule JM-00.266 (i.e., compound IA) was capable of improving gastroparesis induced by a CB1R agonist (AEA) by measuring in vivo progression along the digestive tract of a bolus of nonabsorbable charcoal administered by force-feeding. In the experimental model tested, transit is, as expected, strongly inhibited by AEA. Interestingly, injection of JM-00.266 (i.e., compound IA) beforehand completely abolishes the effect of the agonist and normalizes gastrointestinal transit (FIG. 5). These data indicate, first, that the digestive tract is a target of JM-00.266 (i.e., compound IA) and, second, that this molecule is capable of cancelling the effects of an agonist on CB1R, i.e., of exerting an antagonistic effect on the receptor.

2.2. Long-term In Vivo Experiments (Chronic Injections) in Obese Mice with Compound JM-00.266.

In order to determine the long-term effects of compound JM-00.266 (i.e., compound IA), C57BL/6 mice were made obese by means of a high-sucrose, high-fat diet administered for 20 weeks. These mice then received daily an i.p. injection of SR141716 (i.e., rimonabant) (10 mg/kg), JM-00.266 (i.e., compound IA) (10 mg/kg) or of vehicle for a period of 30 days.

2.2.1. Effects of Chronic Treatment with Compound JM-00.266 (i.e., Compound IA) on Markers of Liver Damage The liver enzymes alanine aminotransferase (ALT), aspartate aminotransferase (AST), intestinal alkaline phosphatase (ALPI), gamma GT and total bilirubin are markers of cell damage. These markers were measured in the plasma in order to detect possible liver toxicity of compound JM-00.266 (i.e., compound IA).

TABLE 1

Plasma concentration of liver markers at the conclusion of 30-day chronic treatment with SR141716 (rimonabant) or compound JM-00.266 (compound IA, also called M6) in comparison with vehicle (Control).

|  | Control | SR141716 | JM-00.266 |
| --- | --- | --- | --- |
| Gamma GT (U/L) | <3 | <3 | <3 |
| ALT (U/L) | 62.0 ± 24.9 | 21.6 ± 2.3* | 34.3 ± 10.5 |
| AST (U/L) | 131.2 ± 47.0 | 46.4 ± 3.1* | 60.8 ± 13.4 |
| ALPI | 52.7 ± 7.8 | 37.4 ± 2.4 | 47.3 ± 3.6 |
| Total bilirubin (µmol/L) | <2 | <2 | <2 |

ALT: alanine aminotransferase; AST: aspartate aminotransferase, ALPI: intestinal alkaline phosphatase.

The results presented in Table 1 show that a 30-day chronic treatment with SR141716 (i.e., rimonabant) or JM-00.266 (i.e., compound IA) does not cause an increase in liver damage markers compared with the control. On the contrary, the ALT and AST concentrations detected in the plasma of obese mice are significantly decreased by SR141716 (i.e., rimonabant) while the same trend is observed with JM-00.266 (i.e., compound IA).

In conclusion, the results suggest not only that chronic administration of compound JM-00.266 (i.e., compound IA) causes no liver toxicity but also that it reduces the cell damage caused by obesity.

2.2.2. Effects of Chronic Treatment with Compound JM-00.266 (i.e., Compound IA) on Certain Behavioural Parameters Related to Activation of Central CB1R.

The open-field test consists in measuring, by a system of infrared beams, the animal's movements in a lighted enclosure representing a stressful environment. The variables measured in the open field are total ambulatory activity and number of entries and time spent in the central area. This test makes it possible, in addition to measuring locomotor activity, to learn about the animal's anxiety state.

Figure 6:
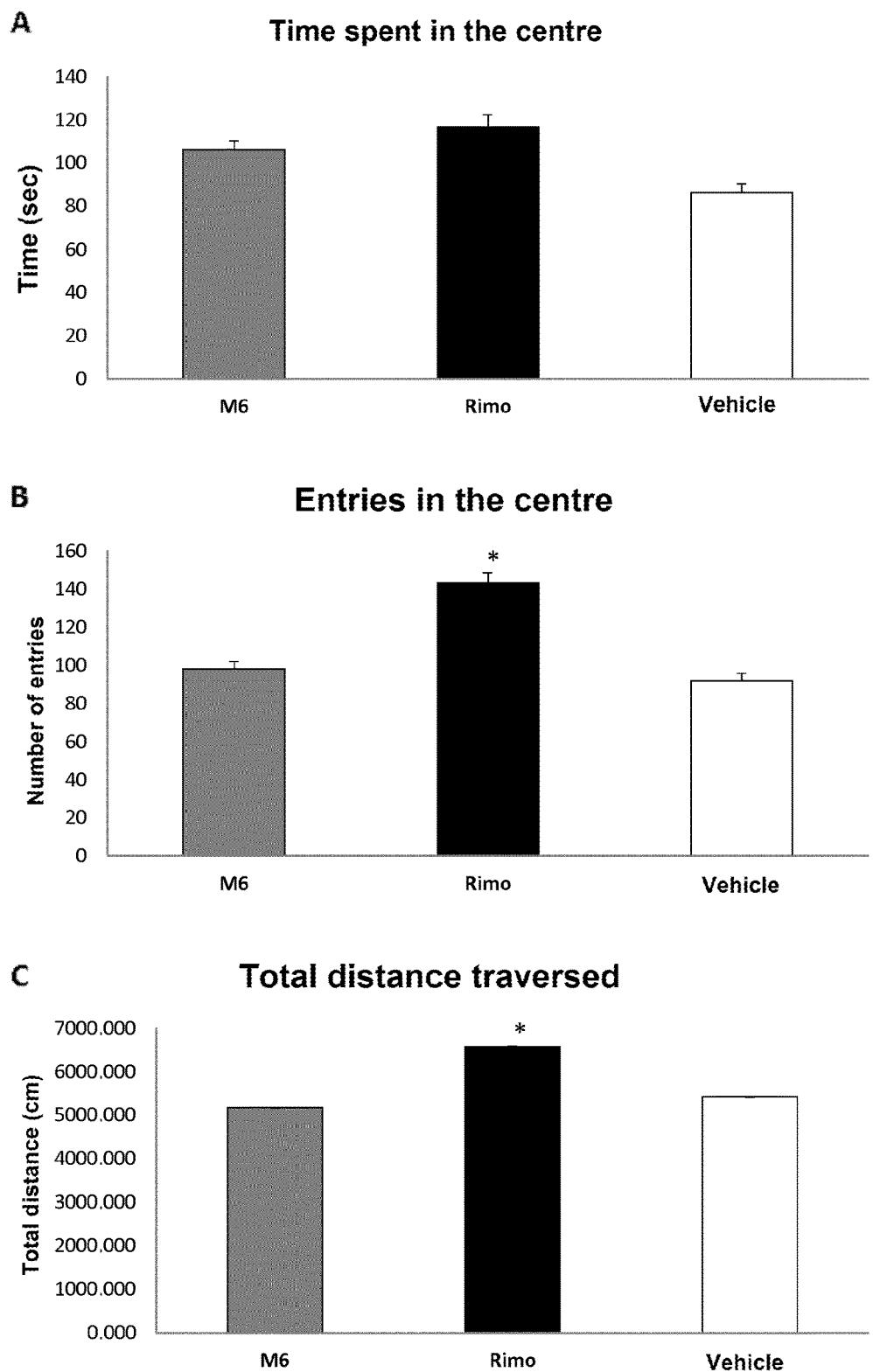
FIG. 6. Effect of a 30-day chronic treatment with SR141716 (i.e., rimonabant), compound JM-00.266 (M6) or vehicle on anxiety and motor activity in obese mice determined by the open-field test 6A: time spent in the centre (in seconds); 6B: number of entries into the centre; 6C: total distance traversed (in cm).

The test results indicate, on the one hand, that neither administration of SR141716 (i.e., rimonabant) nor that of JM-00.266 (i.e., compound IA) has a significant effect on time spent in the centre of the arena (the most anxiogenic area), suggesting that the anxiety state of obese mice was not altered at the end of the 30-day treatment (FIG. 6). On the other hand, it should be noted that SR141716 (i.e., rimonabant) increases motor activity whereas compound JM-00.266 (i.e., compound IA) has no effect on this parameter, suggesting that JM-00.266 (i.e., compound IA) exerts no central action.

2.2.3. Effects of Chronic Treatment with Compound JM-00.266 (i.e., Compound IA) on Food Intake, Weight and Body Composition.

Figure 7:
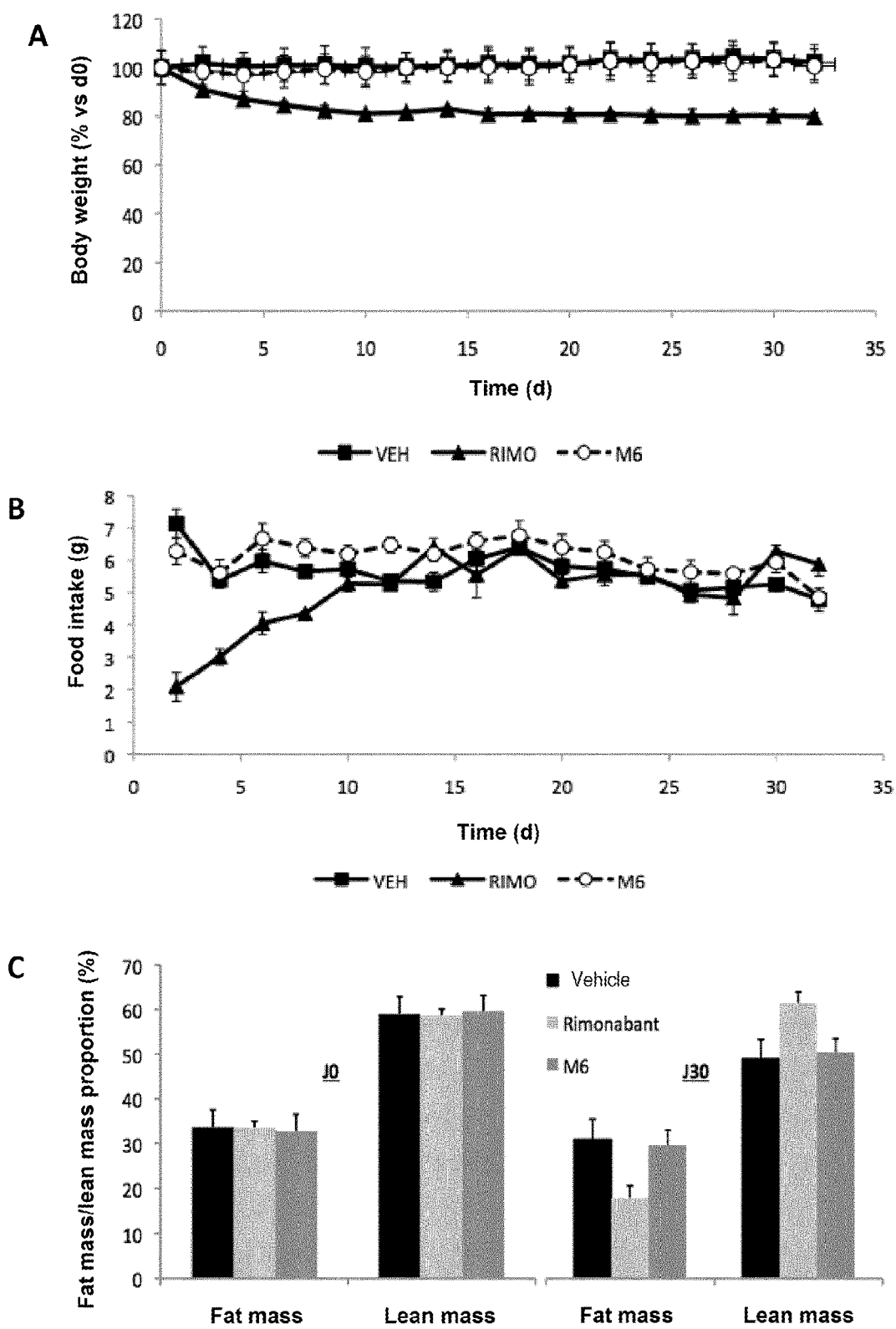
FIG. 7. Change in food intake (7A) and in body weight (7B) during a 30-day chronic treatment with compound JM-00.266 (M6) in comparison with SR141716 (rimonabant) and with vehicle. (7C) Change in body composition (EchoMRI) before (D0) and at the conclusion of the treatments (D30).

Throughout the treatment, food intake and body weight were measured every two days. FIG. 7A shows that the food intake of treated animals is not altered by treatment with JM-00.266 (i.e., compound IA) compared with that of control mice having received vehicle. Only the mice having received SR141716 (i.e., rimonabant) transiently decrease their food intake.

Parallel to food intake, change in body weight in response to the treatments was monitored every two days (FIG. 7B). The results show that the mice treated with SR141716 (i.e., rimonabant) lost weight, which is consistent with the reduced food intake observed. The body weight of the animals treated with JM-00.266 (i.e., compound IA) does not decrease relative to the control mice.

At the end of the treatment, the body composition (fat mass, lean mass) of the mice was analysed by NMR. FIG. 7C shows that only the mice treated with SR141716 (i.e., rimonabant) have a lower fat mass and a higher lean mass than those of the control mice.

The effect of SR141716 (i.e., rimonabant) observed in this study has already been described in the literature and is explained by the central action of SR141716 on CB1R leading to a rapid (but transient) reduction in food intake followed by a loss of body mass (Ravinet Trillou et al., 2003). The fact that compound JM-00.266 (i.e., compound IA) has no effect on food intake or on weight, on the timescale tested, confirms that the action of the compound is indeed limited to the peripheral CB1 receptors.

Figure 8:
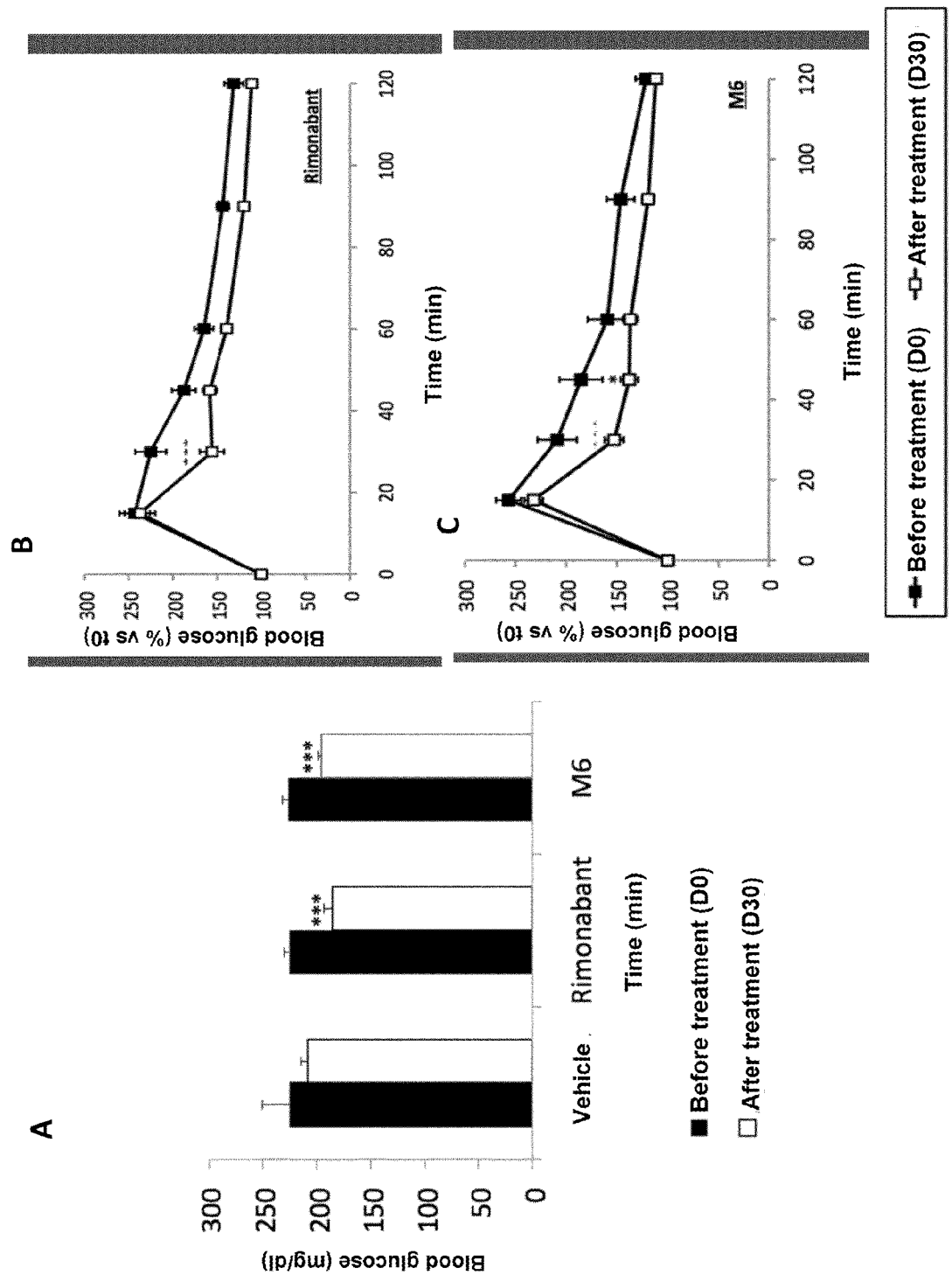
FIG. 8. Effect of a 10 mg/kg chronic treatment with SR141716 (rimonabant) or JM-00.266 (M6) on basal blood glucose (8A) and glucose tolerance in obese mice (OGTT 2 g/kg) (8B: with rimonabant and 8C: with M6).

2.2.4. Effects of Chronic Treatment with Compound JM-00.266 (i.e., Compound IA) on Blood Glucose and Glucose Tolerance To evaluate the long-term effects of compound JM-00.266 (i.e., compound IA) on carbohydrate metabolism, glucose tolerance tests (OGTT 2 g/kg) were carried out before and at the end of the treatments. The results indicate a significant improvement in basal blood glucose (FIG. 8A) and glucose tolerance in obese mice after 30 days of treatment with JM-00.266 and SR141716 (i.e., rimonabant) (FIG. 8B).

Figure 9:
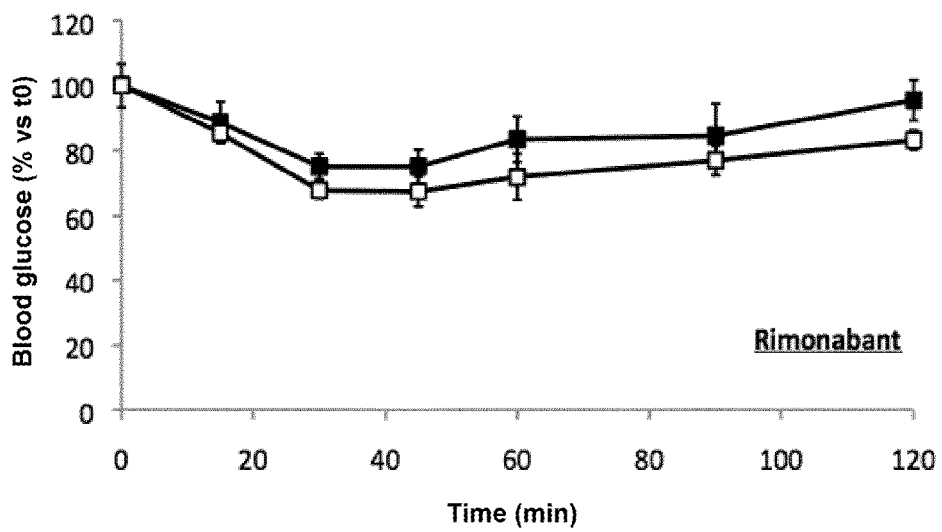
FIG. 9. Effect of a 10 mg/kg chronic treatment with SR141716 (rimonabant) (9A) or JM-00.266 (M6) (9B) on insulin tolerance (ITT) in obese mice.
Figure 9:
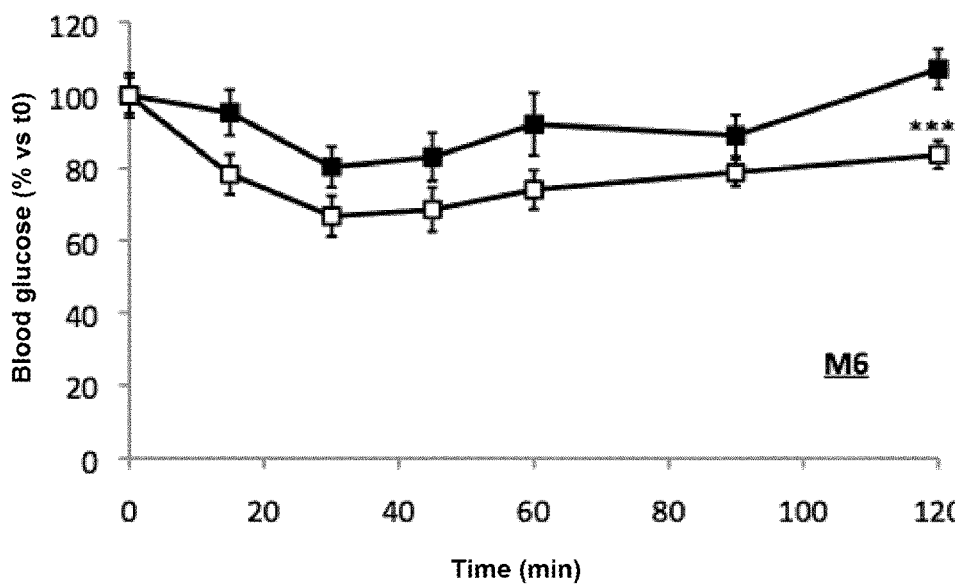

2.2.5. Effects of Chronic Treatment with Compound JM-00.266 (i.e., Compound IA) on Blood Insulin and Insulin Sensitivity In order to know if the improvement in blood glucose control induced by chronic administration of compound JM-00.266 (i.e., compound IA) can be associated with an improvement in insulin resistance, ITTs were used to measure the effect of the treatment on insulin sensitivity. This test shows that the insulin resistance of obese mice detected before the beginning of the treatment is improved after administration of SR141716 (i.e., rimonabant) and JM-00.266 (i.e., compound IA) for 30 days (FIG. 9). It should be noted that the reduction in blood glucose induced by insulin injection is more marked in mice treated with JM-00.266 (i.e., compound IA) than in those treated with SR141716 (i.e., rimonabant).

Figure 10:
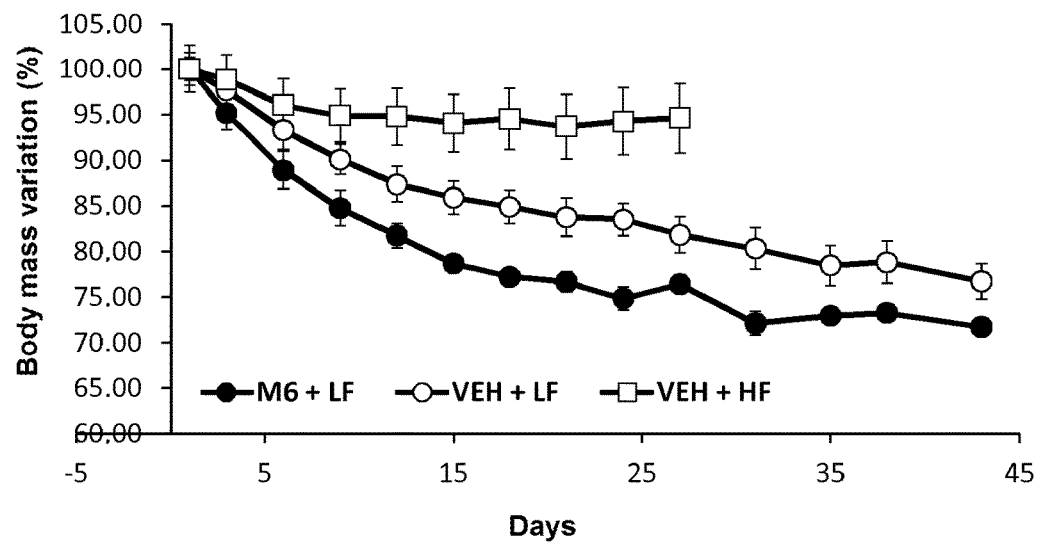
FIG. 10. Variation in the body mass of obese mice subjected to a low-fat (LF) diet and treated for 43 days with compound JM-00.266 (M6) (M6+LF), in comparison with vehicle in the low-fat diet condition (VEH+LF) or with vehicle in the high-fat (HF) condition (VEH+HF).

2.3. In Vivo Effect of Long-term Administration of Compound IA (Also Called M6 or JM-00.266) in Combination with a Reduced Energy Supply in Obese Mice 2.3.1. Effect on Body Mass As the results presented in the graph in FIG. 10 show:
 when obese mice (46.21±1.18 g) are maintained on the high-fat diet (30% crude fat, 33.5% carbohydrates) (VEH+HF), their body mass remains stable;
 when obese mice (46.01±0.84 g) are fed a low-fat diet (5% lipids) (VEH+LF) instead of a high-fat diet with 30% crude fat, they lose weight;
 when obese mice (45.83±0.82 g) are fed a low-fat diet with 5% lipids and receive compound M6 (M6+LF), their weight decreases significantly more.

Consequently, it was observed that administration of compound M6 as an adjunct to a low-fat diet enhances the weight loss induced by caloric restriction in mice first made obese by a high-fat diet.

2.3.2. Effect on Glucose Tolerance

Figure 11:
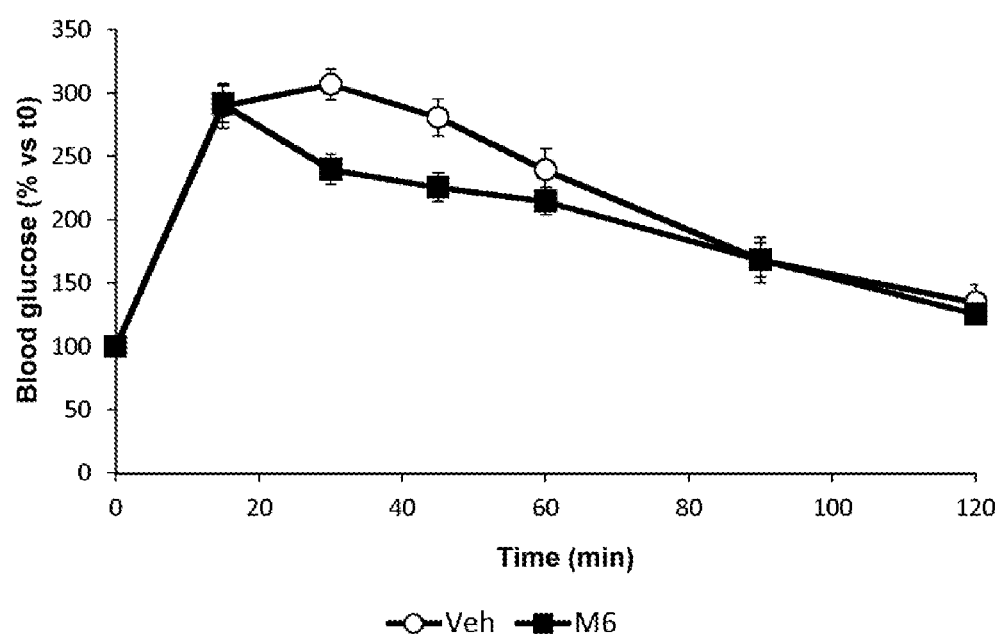
FIG. 11. Effect of a 43-day treatment with compound JM-00.266 (M6) on obese mice subjected to a low-fat diet (M6+LF) in comparison with vehicle (VEH+LF), on glucose tolerance.

As the results presented on the graph in FIG. 11 show: after 43 days of treatment with compound M6 (JM-00.266) administered orally (10 mg/kg) once per day or with vehicle, mice subjected to the low-fat diet (M6+LF) exhibit better glucose tolerance compared with the respective controls, vehicle and low-fat diet (VEH+LF) and vehicle and high-fat diet (VEH+HF).

Figure 12:
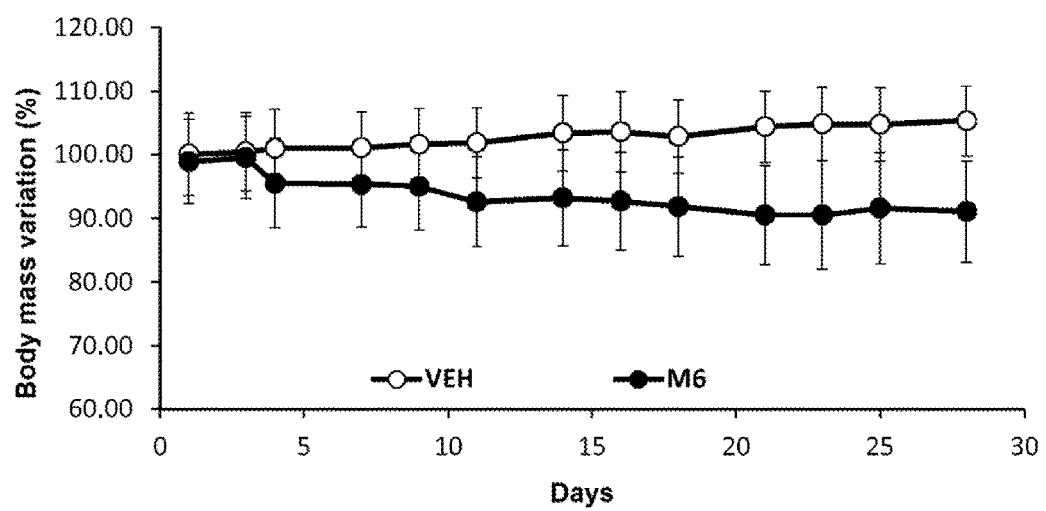
FIG. 12. Variation of the body mass of obese mice treated for 28 days with compound JM-00.266 (M6) administered orally (10 mg/kg) simultaneously with food, in comparison with vehicle.

2.4. In Vivo Effect of Long-term Administration of Compound IA (Also Called M6 or JM-00.266) Simultaneously with Food in Obese Mice 2.4.1 Effect on Body Mass As the results presented on the graph in FIG. 12 show: when obese mice (46.81±3.02 g) subjected to a high-fat diet (35% crude fat) are treated with compound M6 at a rate of one administration daily during the meal (M6), they lose more weight than the mice treated with vehicle (VEH).

Consequently, administration of compound M6 during the meal promotes weight loss in mice made obese by a high-fat diet and subjected to this same diet during the treatment. Similar results are expected with administration of compound M6 right before the meal, taking into account the effects of compound M6 observed on blood glucose control when it is administered acutely 10 minutes before administration of glucose (see section 2.1.3 above).

2.4.2 Effect on Glucose Tolerance

Figure 13:
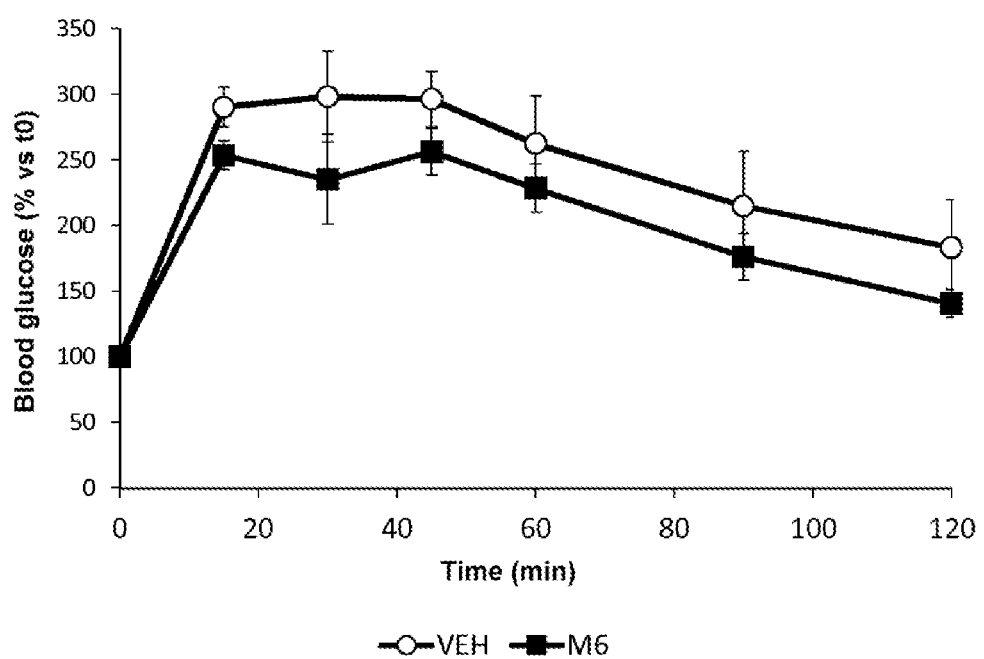
FIG. 13. Effect of a 28-day treatment with compound JM-00.266 (M6) administered orally simultaneously with food on obese mice, in comparison with vehicle, on glucose tolerance.
Figure 14:
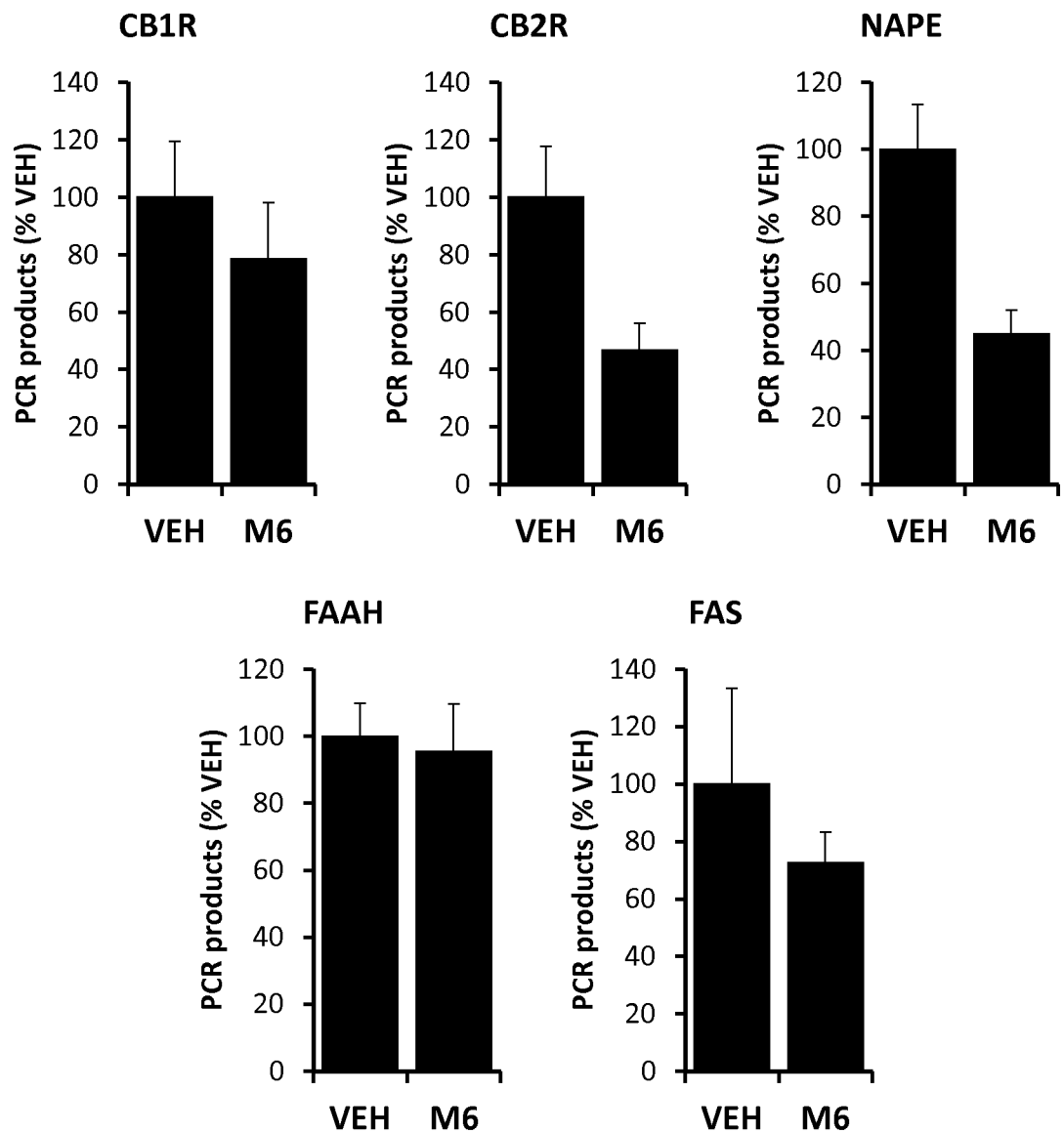
FIG. 14. Expression of receptors CB1R, CB2R, of the endocannabinoid synthesis enzyme (NAPE), of the endocannabinoid degradation enzyme (FAAH), of fatty acid synthase (FAS) in the liver of obese mice treated for 28d with compound JM-00.266 (M6) administered orally simultaneously with food, in comparison with vehicle (VEH).
Figure 15:
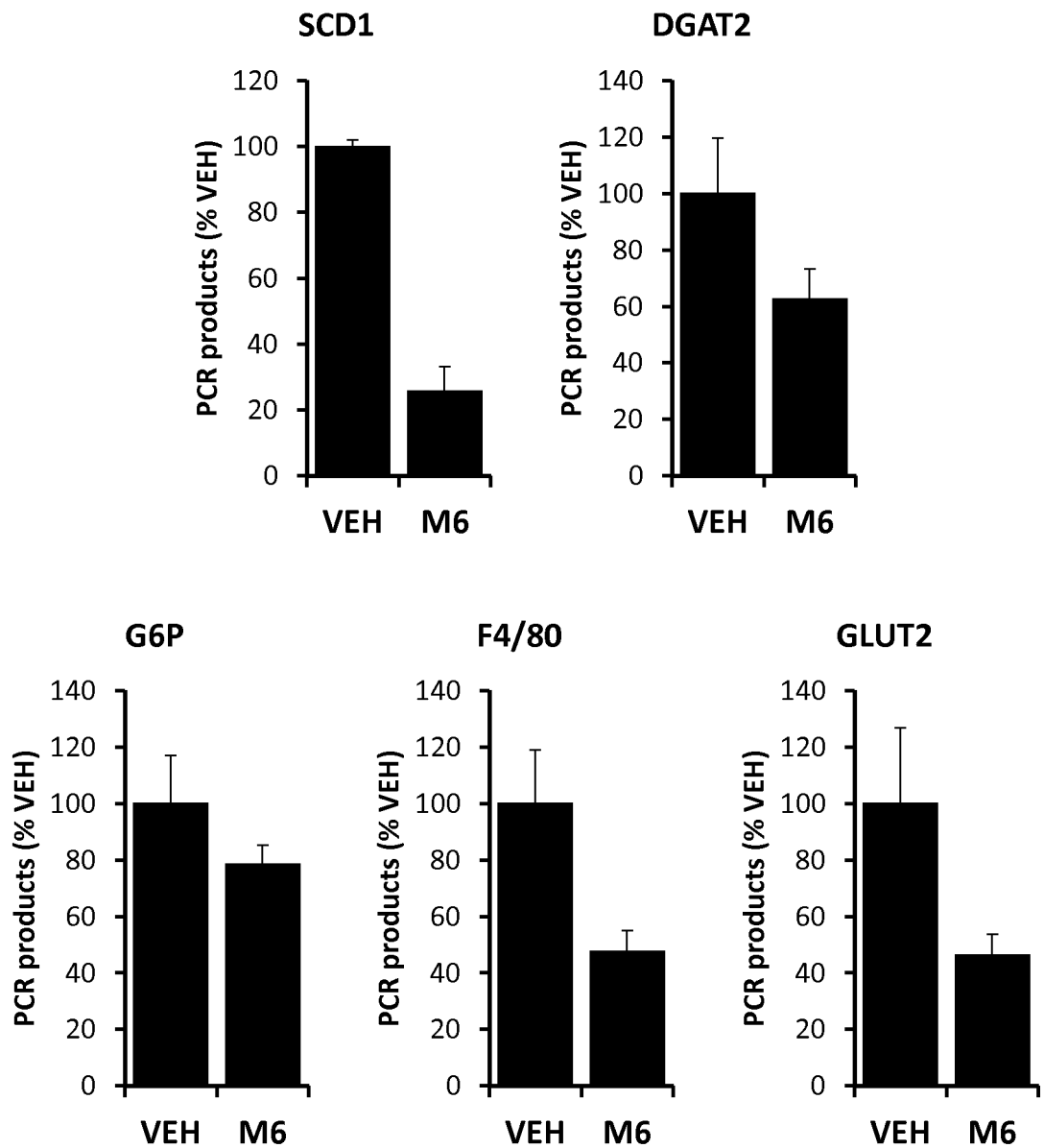
FIG. 15. Expression of stearoyl-CoA desaturase 1 (SCD-1), of acyl-coenzyme A:diacylglycerol acyltransferase 2 (DGAT2), of glucose-6-phosphatase (G6P), of the mature macrophage marker F4/80, and the glucose transporter GLUT2, in the liver of obese mice treated for 28d with compound JM-00.266 (M6) administered orally simultaneously with food, in comparison with vehicle (VEH).
Figure 16:
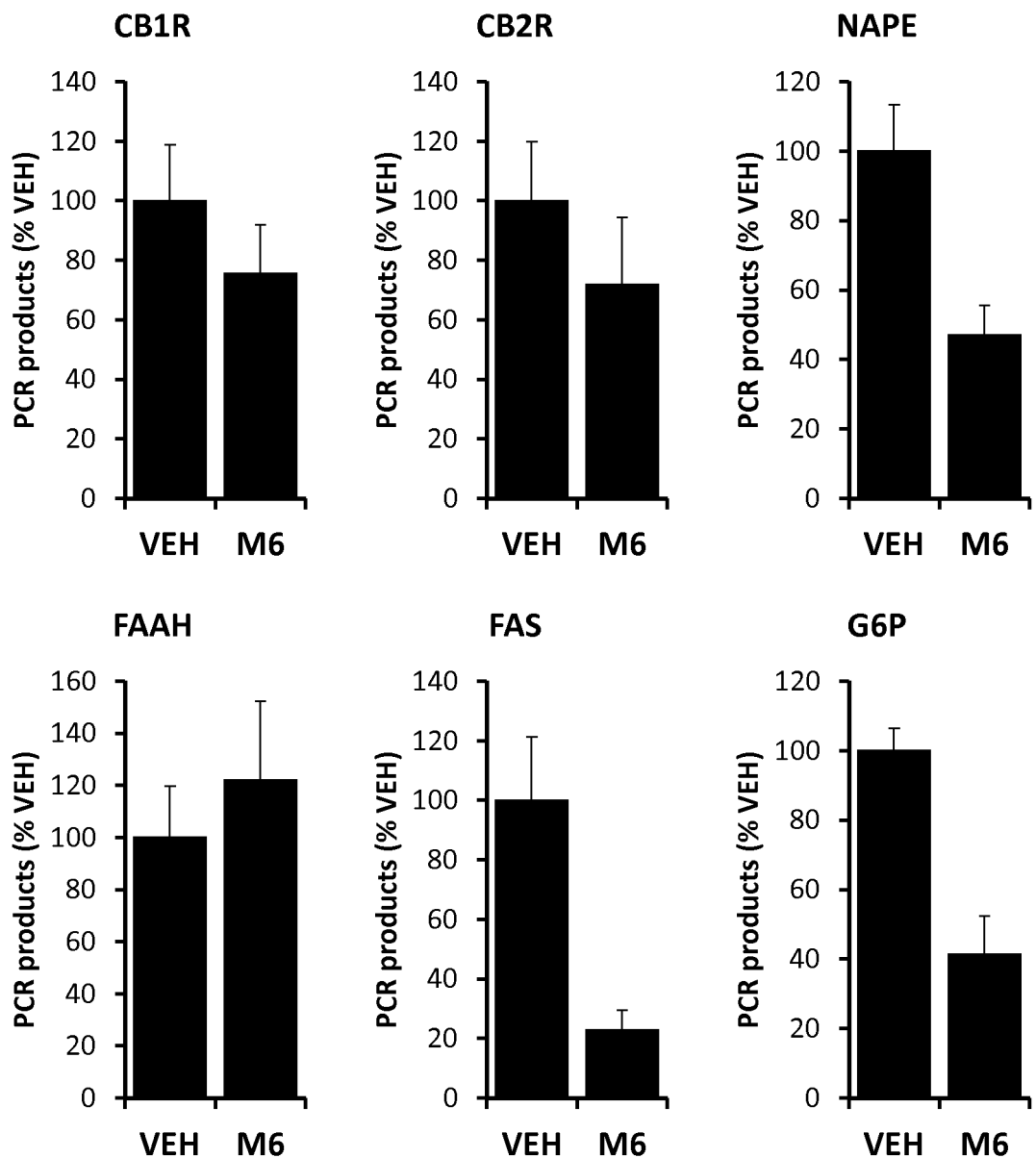
FIG. 16. Expression of receptors CB1R, CB2R, of the endocannabinoid synthesis enzyme (NAPE), of the endocannabinoid degradation enzyme (FAAH), of fatty acid synthase (FAS), of glucose-6-phosphatase (G6P) in the subcutaneous adipose tissue of obese mice treated for 28d with compound JM-00.266 (M6) administered orally simultaneously with food, in comparison with vehicle (VEH).
Figure 17:
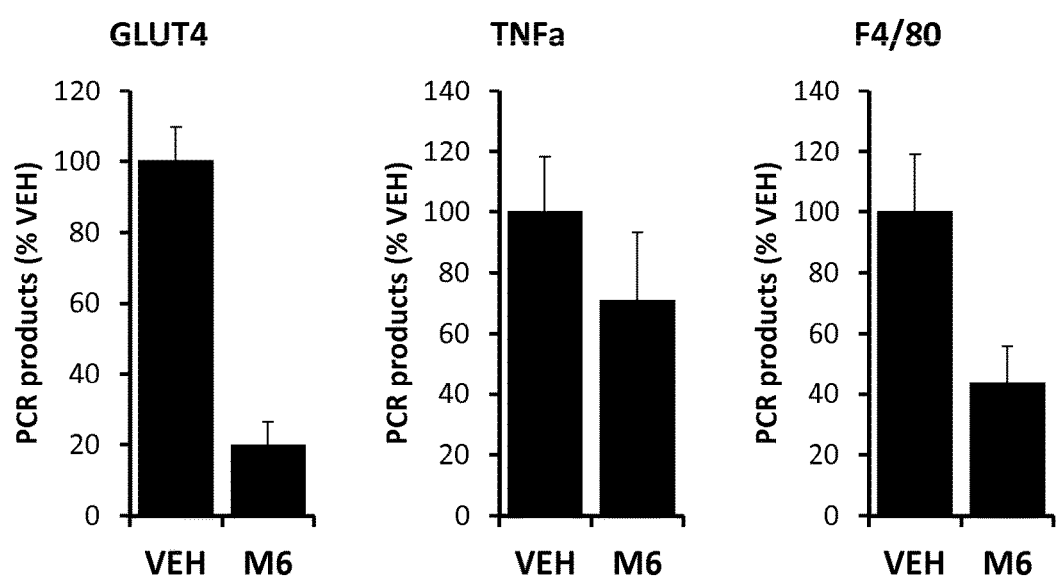
FIG. 17. Expression of the glucose transporter GLUT4, of tumour necrosis factor-alpha (TNF-α), and of the mature macrophage marker F4/80, in subcutaneous adipose tissue explants of obese mice treated for 28d with compound JM-00.266 (M6) administered orally simultaneously with food, in comparison with vehicle (VEH).
Figure 18:
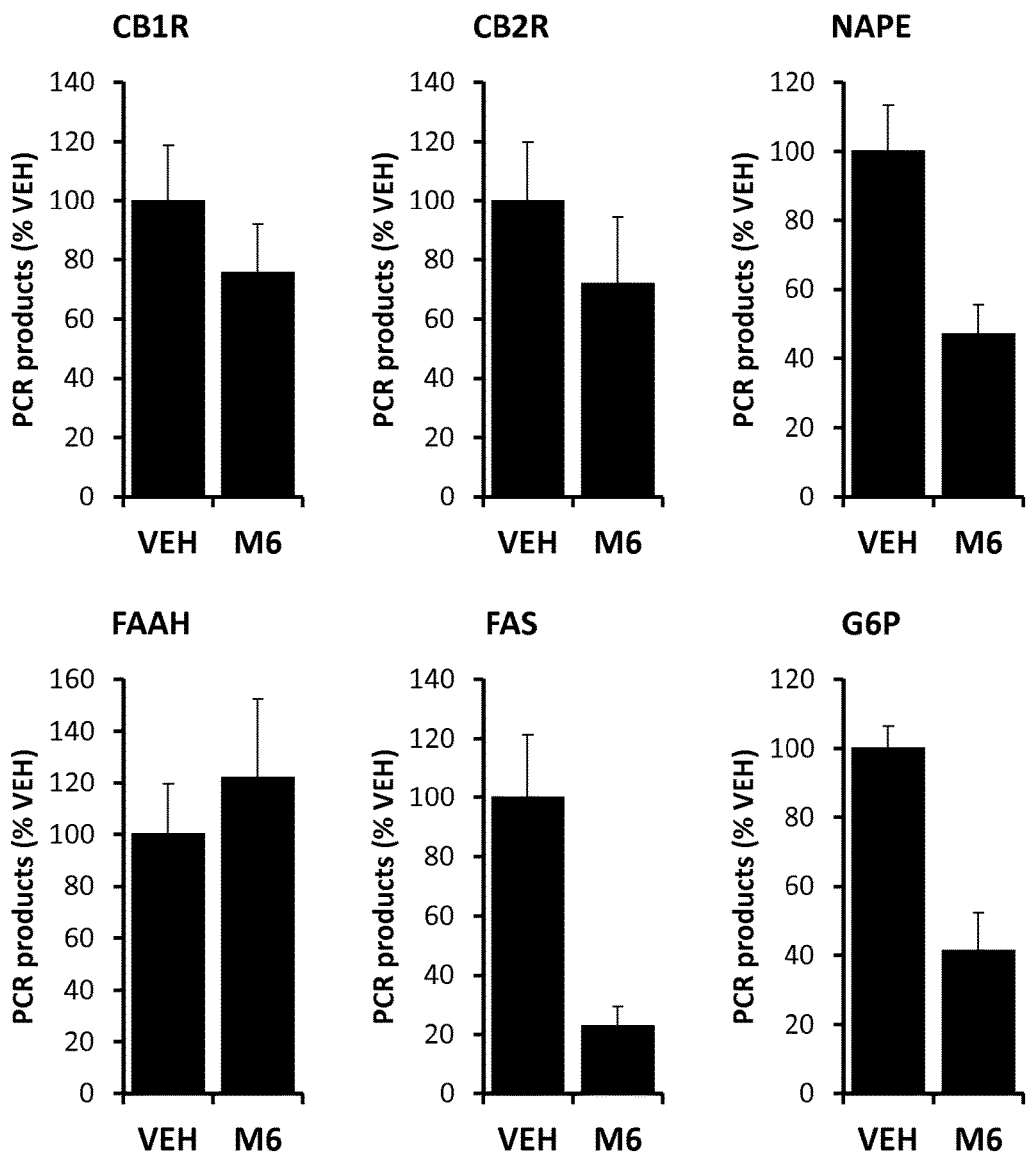
FIG. 18. Expression of receptors CB1R, CB2R, of the endocannabinoid synthesis enzyme (NAPE), of the endocannabinoid degradation enzyme (FAAH), of fatty acid synthase (FAS) and of glucose-6-phosphatase in explants of visceral adipose tissue of obese mice treated for 28d with compound JM-00.266 (M6) administered orally simultaneously with food, in comparison with vehicle (VEH).
Figure 19:
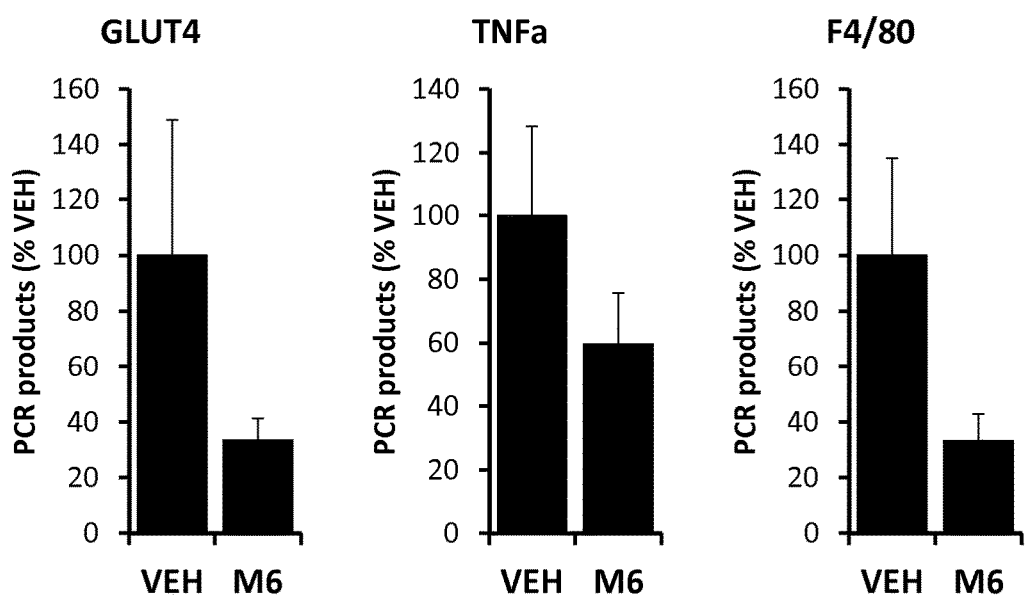
FIG. 19. Expression of the glucose transporter GLUT4, of tumour necrosis factor-alpha (TNF-α), and of the mature macrophage marker F4/80, in explants of visceral adipose tissue of obese mice treated for 28d with compound JM-00.266 (M6) administered orally simultaneously with food, in comparison with vehicle (VEH).

As the results presented on the graph in FIG. 13 show: after 28 days of treatment with compound M6, administered at the same time as the meal, the mice exhibit better glucose tolerance than the mice treated with administration of vehicle at the same time as the meal.

2.4.3 Effect on Gene Expression of Markers

Treatment with M6 led to a reduction in the expression of NAPE-PLD in the tissues tested, suggesting a reduction in endocannabinoid tone.

Expression of CB R and of the endocannabinoid degradation enzyme (fatty acid amide hydrolase, FAAH) is not modified by the treatment in any of the tissues tested. CB2R expression is also lower in tissues of animals treated with M6. CB2R being expressed mainly in immune cells, it is possible that this result reflects a lower macrophage infiltration.

Fatty acid synthase (FAS), stearoyl-CoA desaturase 1 (SCD-1) and glycerol-phosphate acyl-transferase (GPAT2) are enzymes whose expression variations reflect lipogenic activity. Thus, the reduction in expression of SCD-1 and GPAT in the liver and of FAS in the adipose tissue of animals treated with M6 suggests lower lipid synthesis in these tissues.

Glucose-6-phosphatase (G6P) and the glucose transporters GLUT2 and GLUT4 in the liver are used herein as neoglucogenesis markers. The results suggest that treatment with M6 may be associated with lower glucose production by the liver.

The reduction in G6P and GLUT4 expression in the adipose tissue of mice treated with M6 may reflect a reduction in the use of the glucose engaged in the lipogenesis pathway.

F4/80 is a mature macrophage marker. F4/80 expression appears clearly decreased in the liver and the adipose tissues, suggesting a lower macrophage infiltration.

Tumour necrosis factor-alpha (TNF-a) is a proinflammatory cytokine affecting the regulation of numerous biological processes such as immune functions, cell differentiation and energy metabolism. It is accepted that the macrophages having infiltrated the adipose tissue of obese mice are responsible for an increase in TNF-a production. In the present study, a trend towards the reduction of TNF-a expression in adipose tissue is observed, in combination with the reduction in F4/80 expression by M6. These results seem consistent with the reduction in CB2R expression which is located essentially on the immune cells.

III. Conclusion

Obesity is associated with endocannabinoid 1 receptor (CB1R)-dependant hyperactivation of the endocannabinoid system (ECS). Thus, CB1R inactivation constitutes a treatment strategy for fighting obesity-related metabolic disorders. SR141716 (rimonabant), CB1R inverse agonist, was the first anti-obesity agent marketed but nevertheless was quickly withdrawn from the market because of neuropsychiatric side effects resulting from the blocking of central CB1R. However, an action targeting the peripheral CB1R may constitute a therapeutic solution in its own right for treating obesity and certain obesity-related diseases. Indeed, even if the reduction in food intake seems to be the principal cause of weight loss and of improvement in metabolic parameters, several studies in animals and in man indicate that the peripheral CB1R may also be involved in the regulation of lipid and glucose metabolism (Nogueiras et al., 2008; Osei-Hyiaman et al., 2008). Consequently, it has been suggested that the long-term beneficial effects of endocannabinoid system inactivation are due to both the central effects on food intake and the peripheral effects on adipose tissue, liver, skeletal muscle and pancreas. The role of peripheral CB1R has been clearly shown by the work of Tam et al. in 2010 indicating that the blocking of these receptors by a peripheral antagonist decreases cardiometabolic risk in obese mice. Two recent studies are also in agreement with this notion. The first suggests that a reduction in endocannabinoid system activity in visceral adipose tissue is associated with normalization of adipocyte metabolism favourable to reversal of hepatic steatosis observed in obese mice (Jourdan et al., 2010). The second shows by an in vitro approach that inactivation of hepatic CB1R leads to a stimulation of fatty acid beta-oxidation (Jourdan et al., 2012). The use of compounds acting as endocannabinoid CB1 receptor (CB1R) antagonists is thus of unquestionable interest in controlling regulation of food intake and of carbohydrate and lipid metabolism in diseases such as metabolic syndrome having a significant public health impact. Furthermore, the development of compounds retaining activity on peripheral CB1R, but not crossing the blood-brain barrier, would make it possible to circumvent the difficulties of clinical use of rimonabant-generation molecules.

These results, based on three approaches, "in vitro", "short-term in vivo" and "long-term in vivo", show that, among five novel molecules tested, only compound JM-00.266 has:

(1) inverse agonist properties with respect to CB1 receptors, (2) limited peripheral action and is thus unlikely to produce deleterious psychotropic side effects as was the case with compounds arising from past attempts at development, (3) beneficial effects on carbohydrate-lipid metabolism, within the context of obesity, by improving in particular glucose tolerance and insulin sensitivity, and by decreasing blood triglycerides, and (4) a capacity to prevent the inhibitory action of anandamide (natural CB1R agonist) on gastrointestinal motility, which shows a powerful antagonistic effect of the compound in vivo, as well as its utility in the treatment of gastroparesis.

The effect of compound JM-00.266 in vivo on body mass and certain biological parameters in obese mice as a function of the mode of administration also made it possible to bring to light the following:

this compound, administered as an adjunct to a low-fat diet, enhances the weight loss induced by caloric restriction in mice first made obese by a high-fat diet and improves glucose tolerance. These results make it possible to envisage treatments combining this type of compound with normocaloric diets and/or with compounds known to negatively regulate food intake;

this compound, administered during the meal, promotes weight loss in mice made obese by a high-fat diet and subjected to this same diet during the treatment, and improves glucose tolerance. These results make it possible to envisage protocols for administering the compound of interest preferably right before and/or during the meal(s);

the in vivo effect of this compound on various markers of endocannabinoid system activity, of lipogenic activity, and of macrophage infiltration, especially suggests a reduction in endocannabonoid tone, lower lipid synthesis in tissues, a reduction in the use of the glucose engaged in the lipogenesis pathway and a lower macrophage infiltration.

Furthermore, the structure of this novel compound and the possibilities of pharmacomodulation thereof thus make it possible to access molecules diffusing little or not at all in the central nervous system, which are represented by the compounds of formula (I) described above.

Taking into account the properties observed within the context of this work, the compound of formula (I) according to the invention is without question of therapeutic interest not only with respect to obesity-related diseases, but also for diseases for which CB1R involvement in various peripheral tissues has been shown. Thus, peripheral CB1R inactivation by the compound according to the invention can make it possible to treat insulin resistance (Song et al., 2011; Eckardt et al., 2009), type II diabetes (Matias et al. 2006; Jensen, 2006), non-alcoholic hepatic steatosis (Osei-Hyiamann et al., 2005; Osei-Hyiaman et al. 2008; Jeong et al. 2008), liver fibrosis (Teixeira-Clerc et al. 2006), nephropathy (Jourdan et al., 2012), renal fibrosis (Lecru et al., 2015), cardiomyopathies (Montecucco and Di Marzo, 2012; Rajesh et al., 2012; Slavic et al., 2013; Schaich et al., 2014; Pacher and Kunos, 2013), gastroparesis (Izzo and Sharkey, 2010), bone growth and cartilage development (Tam et al., 2008; Wasserman et al., 2015), muscle development (Iannotti et al., 2014), fertility, especially sperm motility and viability in men (Amoako et al., 2014) and oocyte implantation in women (Wang et al., 2006).

REFERENCES

Amoako A A et al. (2014). *Fertil. Steril.;* 102:1260-1267.
Beaumont H, Jensen J et al. (2009). *Br J Pharmacol;* 156(1):153-62.
Blüher M, Engeli et al. (2006). *Diabetes;* 55(11):3053-60.
Buckley N E, Hansson S et al. (1998). *Neuroscience;* 82(4):1131-1149.
Cota D, Marsicano G et al. (2003). *J clin Invest;* 112(3): 423-431.
Côté M, Matias I, et al. (2007). *Int J Obes* (Lond); 31(4): 692-9.
Das S K, Paria B C et al. (1995). *Proc Natl Acad Sci USA;* 92(10):4332-4336.
Despres J P and Lemieux I (2006). *Nature;* 444(7121):881-887.
Di Carlo G and Izzo A A (2003). *Expert Opin Investig Drugs;* 12(1):39-49.
Di Marzo V and Matias I (2005). *Nat Neurosci;* 8(5):585-9.
Di Marzo V (2008). *Nature Reviews Drug Discovery;* 7:438-455.
Di Marzo V et al. (2008). *British Journal of Pharmacology;* 153:1272-1280.
Eckardt K et al. (2009). *Diabetologia;* 52:664-674.

Gye M C, Kim C et al. (2001). *Arch Androl;* 46(1): 51-55.
Hoehe M R, Carnazzo L et al. (2001). *Novel biol;* 3(9): 880-885.
Iannotti F A et al. (2014). *Proc. Natl. Acad. Sci. U.S.A;* 117:2472-2481.
Izzo A A, Mascolo N et al. (1999). *Arch Pharmacol.;* 360(2):221-3.
Izzo A A, Fezza F et al. (2001). *Br J Pharmacol;* 134(3): 563-70.
Izzo A A and Sharkey K A (2010). *Pharmacol Ther;* 126 (1):21-38.
Jensen M. (2006). *The American Journal of Medicine* (2007); Vol 120 (9A), S25-S32.
Jeong W I et al. (2008). *Cell Metab.;* 7:227-235.
Jourdan T. et al. (2010). *Diabetes;* 59:926-934.
Jourdan T. et al. (2012). *Hepatology;* 55:790-799.
Jourdan T, Szanda G et al. (2014). *Proc Natl Acad Sci USA;* 111(50):E5420-E5428.
Lehmann A, Blackshaw L A et al. (2002). *Gastroenterology;* 123(4):1129-34.
Lecru L. et al. (2015). *Kidney Int.;* 88(1):72-84
Liu J, Batkai S et al. (2003). *J Biol Chem;* 278(45):45034-45039.
Liu J. et al. (2012). *Gastroenterolog;* 142(5):1218-1228.
Matias I et al. (2006). *J. Clin. Endocrinol. Metab;* 91:3171-3180.
Maccarrone M, Bab I et al. (2015). *Trends Pharmacol Sci.;* 36(5):277-296.
Massa F, Marsicano G et al. (2004). *J Clin Invest;* 113(8): 1202-9.
Nogueiras R et al. (2008). *Diabetes;* 57, 2977-2991.
Osei-Hyiaman D et al. (2005). *J. Clin. Invest;* 115(5): 1298-1305.
Osei-Hyiaman D et al. (2008). *J. Clin. Invest;* 118:3160-3169.
Pacher P and Kunos G (2013). *FEBS J;* 280(9):1918-43.
Pertwee R G (2001). *Prog. Neurobiol;* 63(5):569-611.
Rajesh M et al. (2012). *Diabetes;* 61:716-727.
Rinaldi-Carmona M et al. (1996). *J Pharmacol Exp Ther;* 278(2):871-8.
Ravinet Trillou C et al. (2003). *Am J Physiol Regul Integr Comp Physiol;* 284(2): R345-R353.
Schaich C L et al. (2014). *Physiol. Rep;* 2(8):e12108.
Tam J et al. (2008). *FASEB J.;* 22:285-294.
Tam J, Vemuri V K et al. (2010). *J Clin Invest;* 120(8): 2953-66.
Tam J, Cinar R et al. (2012). *Cell Metab;* 16(2):167-79.
Teixeira-Clere F et al. (2006). *Nature Medicine;* 12(6):671-676.
Slavic S. et al. (2013). *J. Mol. Med.;* 91:811-823.
Song D. et al. (2011). *Diabetologia;* 54:1181-1189.
Wang H. et al. (2006). *Endocr. Rev.* 27:427-448

---

The invention claimed is:

1. A compound of following formula (I):

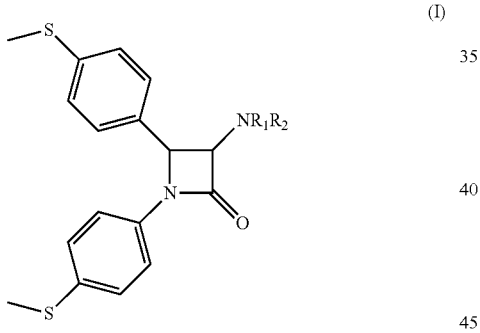

wherein:

R$_1$ and R$_2$, which can be identical or different, represent a hydrogen atom or a COR$_3$, SO$_2$R$_4$ or CONR$_5$R$_6$ group; or form together with the nitrogen atom that bears them a 5- or 6-member heterocycle comprising at least one additional heteroatom, C=O group, aryl group or heteroaryl group;

R$_3$, R$_4$, R$_5$ and R$_6$ independently represent a hydrogen atom, or an aryl or heteroaryl group, said group being optionally substituted by one or more groups selected from a halogen atom, OR$_7$, NR$_8$R$_9$, SR$_{10}$, S(O)R$_{11}$, SO$_2$R$_{12}$, SO$_2$NR$_{13}$R$_{14}$, OCOR$_{15}$, NR$_{16}$COR$_{17}$, NR$_{18}$C(O)OR$_{19}$, CO$_2$R$_{20}$, CONR$_{21}$R$_{22}$, OCO$_2$R$_{23}$, OCONR$_{24}$R$_{25}$, COR$_{26}$, nitro (NO$_2$), cyano (CN), oxo (=O) and CF$_3$; and R$_7$ to R$_{26}$ independently represent a hydrogen atom or a (C$_1$-C$_6$)alkyl, aryl or aryl-(C$_1$-C$_6$)alkyl group, or a pharmaceutically acceptable salt thereof.

2. The compound according to claim 1, wherein R$_1$ and R$_2$ form together with the nitrogen atom that bears them a heterocycle of following formula (II) or (III):

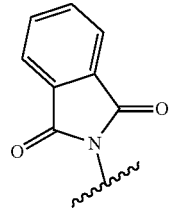

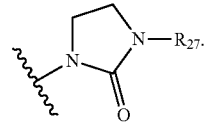

wherein R$_{27}$ represents a hydrogen atom or a COR$_3$ or SO$_2$R$_4$ group, R$_3$ and R$_4$ being as defined in claim 1, in particular R$_{27}$ represents a hydrogen atom.

3. The compound according to claim 1, wherein:

R$_1$ and R$_2$, which can be identical or different, represent a hydrogen atom or a COR$_3$, SO$_2$R$_4$ or CONR$_5$R$_6$ group;

R$_3$, R$_4$ and R$_5$ independently represent an aryl group, optionally substituted by a group selected from a halogen atom, CF$_3$ and SO$_2$R$_{12}$, with R$_{12}$ representing a (C$_1$C$_6$)alkyl group, preferably a methyl; and R$_6$ represents a hydrogen atom.

4. The compound according to claim 1, wherein R$_1$ is a hydrogen atom and R$_2$ represents a COR$_3$, SO$_2$R$_4$ or CONR$_5$R$_6$ group, with R$_3$, R$_4$, R$_5$ and R$_6$ being as defined in claim 1.

5. The compound according to claim 1, wherein it is selected from the following compounds:

Compound (IA)
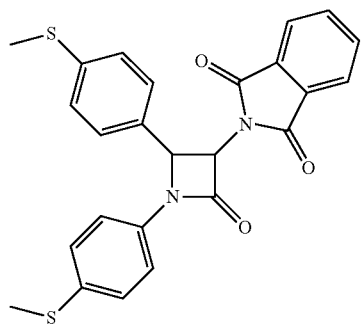

Compound (IB)
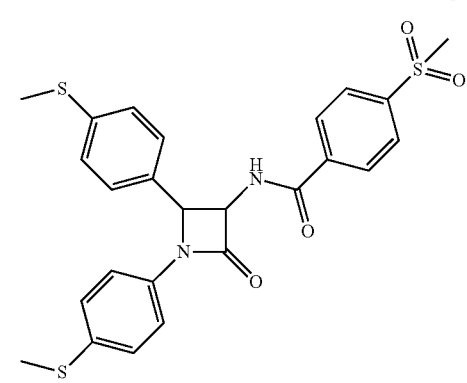

Compound (IC)
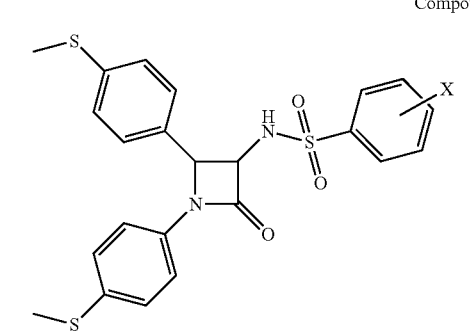

Compound (ID)
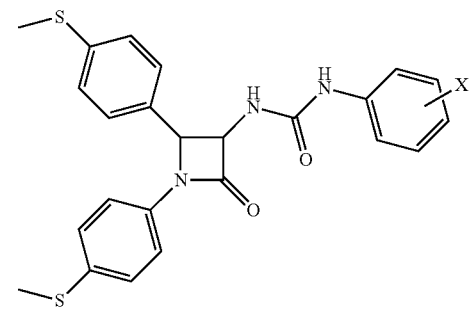

Compound (IE)
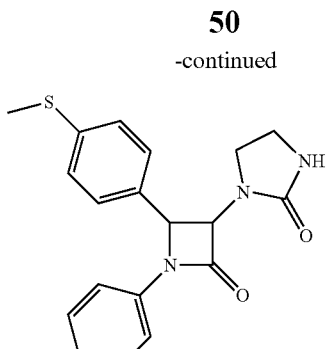

Compound (IF)
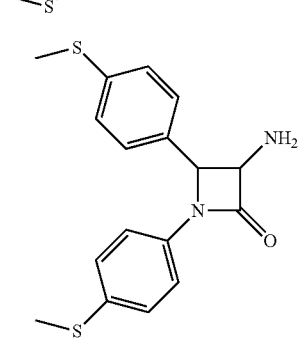

or a pharmaceutically acceptable salt thereof,
wherein X represents a hydrogen atom, a halogen or $CF_3$.

6. A process for preparing a compound of formula (I) as defined according to claim 1, comprising the following steps:

(i) condensation of 4-methylthiobenzaldehyde with 4-methylthioaniline to obtain the composition of following formula (IV):

(IV)
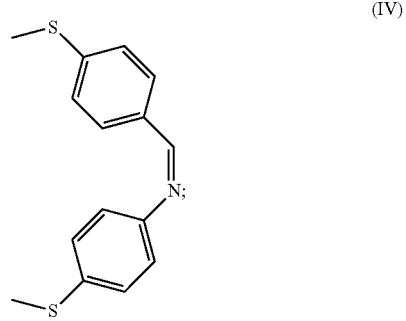 [SMILES: CSc1ccc(/C=N\c2ccc(SC)cc2)cc1]

(ii) Staudinger cycloaddition between the composition of formula (IV) obtained and a ketene of following formula (V):

(V)
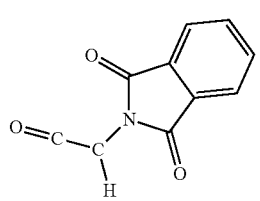

to obtain the composition of following formula (IA):

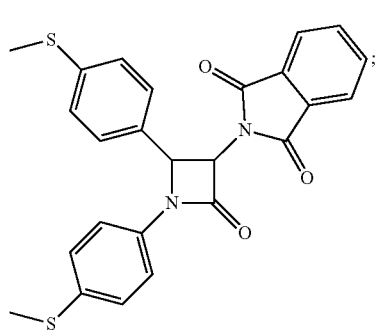
(IA)

(iii) optionally, deprotection of the phthaloylated amine function of the compound of formula (IA), preferably by action of methylhydrazine, to obtain the composition of following formula (IF):

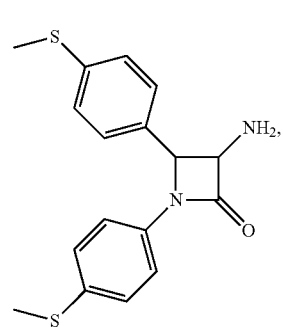
(IF)

then, optionally, coupling of the compound of formula (IF) thus obtained with a compound of formula $R_1$—X and/or $R_2$—X', wherein $R_1$—X and $R_2$—X' are activated forms, such as acyl chlorides, sulphonyl chlorides and aryl isocyanates, of groups $R_1$ and $R_2$ as defined in claim 1; and (iv) collection of the compound obtained in step (ii) or in step (iii).

7. A method comprising the in vitro use of at least one compound of formula (I) as defined in claim 1, as inverse agonist of the peripheral endocannabinoid CB1 receptors, said method comprising the step of contacting in vitro said peripheral endocannabinoid CB1 receptor with at least one compound of formula (I).

8. A pharmaceutical composition comprising as active ingredient at least one compound of formula (I) as defined in claim 1, and at least one pharmaceutically acceptable excipient.

9. A nontherapeutic composition, comprising at least one compound of formula (I) as defined in claim 1, and at least one acceptable excipient.

10. A method for treating diseases associated with hyperactivity of the endocannabinoid system comprising the administration of an effective amount of a compound as defined by the following formula (I):

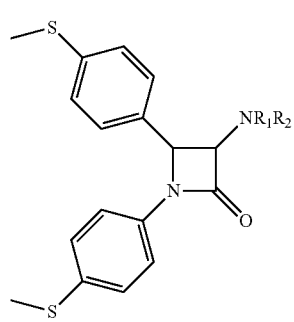
(I)

wherein:

$R_1$ and $R_2$, which can be identical or different, represent a hydrogen atom or a $COR_3$, $SO_2R_4$ or $CONR_5R_6$ group; or form together with the nitrogen atom that bears them a 5- or 6-member heterocycle comprising at least one additional heteroatom, C=O group, aryl group or heteroaryl group;

$R_3$, $R_4$, $R_5$ and $R_6$ independently represent a hydrogen atom, or an aryl or heteroaryl group, said group being optionally substituted by one or more groups selected from a halogen atom, $OR_7$, $NR_8R_9$, $SR_{10}$, $S(O)R_{11}$, $SO_2R_{12}$, $SO_2NR_{13}R_{14}$, $OCOR_{15}$, $NR_{16}COR_{17}$, $NR_{18}C(O)OR_{19}$, $CO_2R_{20}$, $CONR_{21}R_{22}$, $OCO_2R_{23}$, $OCONR_{24}R_{25}$, $COR_{26}$, nitro ($NO_2$), cyano (CN), oxo (=O) and $CF_3$; and R7 to R26 independently represent a hydrogen atom or a (C1-C6)alkyl, aryl or aryl-(C1-$C_6$)alkyl group, or a pharmaceutically acceptable salt and/or solvate thereof, or the pharmaceutical composition as defined in claim 8, in a subject in need thereof.

11. The method according to claim 10, wherein said diseases are selected from obesity and obesity—related metabolic disorders, insulin resistance, diabetes and associated complications, hepatic steatosis, liver fibrosis, cirrhosis, renal fibrosis, nephropathy, cardiomyopathies, gastroparesis, bone and/or cartilage loss, muscle loss, and fertility problems.

12. The method according to claim 10, wherein subject is put on a balanced normocaloric diet.

13. The method according to claim 10, wherein compound or said composition is administered to said subject before and/or during the subject's meal(s).

14. A method for treating a disease associated with hyperactivity of the endocannabinoid system comprising the administration of an effective amount of the compound of formula (I) as defined in claim 1, and therapeutic agent, as combined preparation for simultaneous, separate, or sequential administration, in a subject in need thereof.

15. A nontherapeutic method for promoting and/or accelerating weight gain or for slowing and/or reducing weight gain in a subject, comprising administering an effective amount of a compound of formula (I) as defined by the following formula (I):

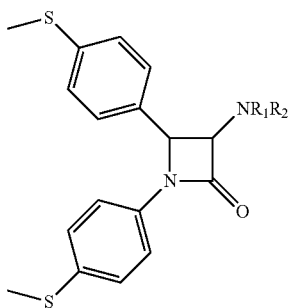 (I)

wherein:

R1 and R2, which can be identical or different, represent a hydrogen atom or a COR3, SO2R4 or CONR5R6 group; or form together with the nitrogen atom that bears them a 5- or 6-member heterocycle comprising at least one additional heteroatom, C═O group, aryl group or heteroaryl group;

R3, R4, R5 and R6 independently represent a hydrogen atom, or an aryl or heteroaryl group, said group being optionally substituted by one or more groups selected from a halogen atom, OR7, NR8R9, SR10, S(O)R11, SO2R12, SO2NR13R14, OCOR15, NR16COR17, NR18C(O)OR19, CO2R20, CONR21R22, OCO2R23, OCONR24R25, COR26, nitro (NO2), cyano (CN), oxo (═O) and CF3; and R7 to R26 independently represent a hydrogen atom or a (C1-C6)alkyl, aryl or aryl-(C1-C6)alkyl group, or a pharmaceutically acceptable salt and/or solvate thereof, or of a composition as defined according to claim 9.

16. The nontherapeutic method according to claim 15, wherein said subject is put on a balanced normocaloric diet.

17. The nontherapeutic method according to claim 15, wherein said compound or said composition is administered to said subject before and/or during the subject's meal(s).

* * * * *

SEQUENCE LISTING

```
<160> NUMBER OF SEQ ID NOS: 26

<210> SEQ ID NO 1
<211> LENGTH: 20
<212> TYPE: DNA
<213> ORGANISM: artificial
<220> FEATURE:
<223> OTHER INFORMATION: TATABox Binding Protein amorce sens

<400> SEQUENCE: 1
acggcacagg acttactcca                                              20

<210> SEQ ID NO 2
<211> LENGTH: 22
<212> TYPE: DNA
<213> ORGANISM: artificial
<220> FEATURE:
<223> OTHER INFORMATION: TATABox Binding Protein amorce antisens

<400> SEQUENCE: 2
gctgtctttg ttgctcttcc aa                                           22

<210> SEQ ID NO 3
<211> LENGTH: 20
<212> TYPE: DNA
<213> ORGANISM: artificial
<220> FEATURE:
<223> OTHER INFORMATION: CB1R amorce sens

<400> SEQUENCE: 3
ccgcaaagat agtcccaatg                                              20

<210> SEQ ID NO 4
<211> LENGTH: 19
<212> TYPE: DNA
<213> ORGANISM: artificial
<220> FEATURE:
<223> OTHER INFORMATION: CB1R amorce antisens
```

```
<400> SEQUENCE: 4
aaccccaccc agtttgaac                                              19

<210> SEQ ID NO 5
<211> LENGTH: 20
<212> TYPE: DNA
<213> ORGANISM: artificial
<220> FEATURE:
<223> OTHER INFORMATION: CB2R amorce sens

<400> SEQUENCE: 5
caaaggagga agtgcttggt                                             20

<210> SEQ ID NO 6
<211> LENGTH: 21
<212> TYPE: DNA
<213> ORGANISM: artificial
<220> FEATURE:
<223> OTHER INFORMATION: CB2R amorce antisens

<400> SEQUENCE: 6
tggagagatc ggcttatgtt g                                           21

<210> SEQ ID NO 7
<211> LENGTH: 20
<212> TYPE: DNA
<213> ORGANISM: artificial
<220> FEATURE:
<223> OTHER INFORMATION: F4/80 amorce sens

<400> SEQUENCE: 7
tgacaaccag acggcttgtg                                             20

<210> SEQ ID NO 8
<211> LENGTH: 22
<212> TYPE: DNA
<213> ORGANISM: artificial
<220> FEATURE:
<223> OTHER INFORMATION: F4/80 amorce antisens

<400> SEQUENCE: 8
gcaggcgagg aaaagatagt gt                                          22

<210> SEQ ID NO 9
<211> LENGTH: 19
<212> TYPE: DNA
<213> ORGANISM: artificial
<220> FEATURE:
<223> OTHER INFORMATION: FAAH amorce sens

<400> SEQUENCE: 9
ggaccttgct cccctttct                                              19

<210> SEQ ID NO 10
<211> LENGTH: 19
<212> TYPE: DNA
<213> ORGANISM: artificial
<220> FEATURE:
<223> OTHER INFORMATION: FAAH amorce antisens

<400> SEQUENCE: 10
cctgctgggc tgtcacata                                              19

<210> SEQ ID NO 11
<211> LENGTH: 20
```

```
<212> TYPE: DNA
<213> ORGANISM: artificial
<220> FEATURE:
<223> OTHER INFORMATION: FAS amorce sens

<400> SEQUENCE: 11
ggctgcagtg aatgaatttg                                               20

<210> SEQ ID NO 12
<211> LENGTH: 20
<212> TYPE: DNA
<213> ORGANISM: artificial
<220> FEATURE:
<223> OTHER INFORMATION: FAS amorce antisens

<400> SEQUENCE: 12
ttcgtacctc cttggcaaac                                               20

<210> SEQ ID NO 13
<211> LENGTH: 20
<212> TYPE: DNA
<213> ORGANISM: artificial
<220> FEATURE:
<223> OTHER INFORMATION: G6P amorce sens

<400> SEQUENCE: 13
tggcctggct tattgtacct                                               20

<210> SEQ ID NO 14
<211> LENGTH: 20
<212> TYPE: DNA
<213> ORGANISM: artificial
<220> FEATURE:
<223> OTHER INFORMATION: G6P amorce antisens

<400> SEQUENCE: 14
gtgctaagag gaagacccga                                               20

<210> SEQ ID NO 15
<211> LENGTH: 19
<212> TYPE: DNA
<213> ORGANISM: artificial
<220> FEATURE:
<223> OTHER INFORMATION: GLUT2 amorce sens

<400> SEQUENCE: 15
ctcttcacca actggccct                                                19

<210> SEQ ID NO 16
<211> LENGTH: 21
<212> TYPE: DNA
<213> ORGANISM: artificial
<220> FEATURE:
<223> OTHER INFORMATION: GLUT2 amorce antisens

<400> SEQUENCE: 16
cagcagatag gccaagtagg a                                             21

<210> SEQ ID NO 17
<211> LENGTH: 21
<212> TYPE: DNA
<213> ORGANISM: artificial
<220> FEATURE:
<223> OTHER INFORMATION: GLUT4 amorce sens

<400> SEQUENCE: 17
```
gatgccgtcg ggtttccagc a                                              21

<210> SEQ ID NO 18
<211> LENGTH: 21
<212> TYPE: DNA
<213> ORGANISM: artificial
<220> FEATURE:
<223> OTHER INFORMATION: GLUT4 amorce antisens

<400> SEQUENCE: 18
tgttccagtc actcgctgcc g                                              21

<210> SEQ ID NO 19
<211> LENGTH: 22
<212> TYPE: DNA
<213> ORGANISM: artificial
<220> FEATURE:
<223> OTHER INFORMATION: DGAT2 amorce sens

<400> SEQUENCE: 19
agccctccaa gacatcttct ct                                             22

<210> SEQ ID NO 20
<211> LENGTH: 19
<212> TYPE: DNA
<213> ORGANISM: artificial
<220> FEATURE:
<223> OTHER INFORMATION: DGAT2 amorce antisens

<400> SEQUENCE: 20
tgcagctgtt tttccacct                                                 19

<210> SEQ ID NO 21
<211> LENGTH: 20
<212> TYPE: DNA
<213> ORGANISM: artificial
<220> FEATURE:
<223> OTHER INFORMATION: NAPE-PLD amorce sens

<400> SEQUENCE: 21
ctcgatatct gcgtggaaca                                                20

<210> SEQ ID NO 22
<211> LENGTH: 20
<212> TYPE: DNA
<213> ORGANISM: artificial
<220> FEATURE:
<223> OTHER INFORMATION: NAPE-PLD amorce antisens

<400> SEQUENCE: 22
ctgaattctg gcgctttctc                                                20

<210> SEQ ID NO 23
<211> LENGTH: 20
<212> TYPE: DNA
<213> ORGANISM: artificial
<220> FEATURE:
<223> OTHER INFORMATION: SCD1 amorce sens

<400> SEQUENCE: 23
ccggagaccc cttagatcga                                                20

<210> SEQ ID NO 24
<211> LENGTH: 26
<212> TYPE: DNA
<213> ORGANISM: artificial

```
<220> FEATURE:
<223> OTHER INFORMATION: SCD1 amorce antisens

<400> SEQUENCE: 24
tagcctgtaa aagatttctg caaacc                                            26

<210> SEQ ID NO 25
<211> LENGTH: 21
<212> TYPE: DNA
<213> ORGANISM: artificial
<220> FEATURE:
<223> OTHER INFORMATION: TNF-a amorce sens

<400> SEQUENCE: 25
cggggtgatc ggtccccaaa g                                                 21

<210> SEQ ID NO 26
<211> LENGTH: 21
<212> TYPE: DNA
<213> ORGANISM: artificial
<220> FEATURE:
<223> OTHER INFORMATION: TNF-a amorce antisens

<400> SEQUENCE: 26
tggtttgcta cgacgtgggc t                                                 21
```